(12) United States Patent
Abdela et al.

(10) Patent No.: US 8,883,488 B2
(45) Date of Patent: Nov. 11, 2014

(54) DETECTION OF FOOD THREAT AGENTS AND FOOD-BORNE PATHOGENS

(75) Inventors: Woubit Salah Abdela, Auburn, AL (US); Temesgen Samuel-Tulore, Auburn, AL (US); Teshome Yehualaeshet, Auburn, AL (US)

(73) Assignee: Tuskegee University, Tuskegee, AL (US)

( * ) Notice: Subject to any disclaimer, the term of this patent is extended or adjusted under 35 U.S.C. 154(b) by 281 days.

(21) Appl. No.: 13/297,003

(22) Filed: Nov. 15, 2011

(65) Prior Publication Data

US 2013/0123119 A1    May 16, 2013

(51) Int. Cl.
*C12M 1/34*    (2006.01)
*C07H 21/04*    (2006.01)
*C12Q 1/68*    (2006.01)

(52) U.S. Cl.
CPC ............ *C12Q 1/689* (2013.01); *C12Q 2600/16* (2013.01)
USPC ...................................... 435/287.2; 536/24.3

(58) Field of Classification Search
None
See application file for complete search history.

(56) References Cited

U.S. PATENT DOCUMENTS

| 6,391,546 | B1 * | 5/2002 | Karube et al. | 435/6.12 |
| 2004/0248148 | A1 * | 12/2004 | Horgen et al. | 435/6 |

OTHER PUBLICATIONS

Kugeler et al. Real-time PCR for *Francisella tularensis* types A and B. Emerging Infectious Diseases (2006) vol. 12, No. 11, pp. 1799-1801.*
Ludu et al. The *Francisella* pathogenicity island protein PdpD is required for full virulence and associates with homologues of the type VI secretion system. J. Bacteriology (2008) vol. 190, No. 13, pp. 4584-4595.*
Taniguchi et al. Cloning and characterization of a gene encoding a new thermostable hemolysin from *Vibrio parahaemolyticus*. FEMS Microbiology Letters (1990) 67:339-346.*
Ward et al. Detection of *Vibrio parahaemolyticus* in shellfish by use of multiplexed real-time PCR with TaqMan fluorescent probes. Applied Enviromental Microbiology (2006) vol. 72, No. 3, pp. 2031-2042.*
Hiroshi Fukushima et al., "Simultaneous Screening of 24 Target Genes of Foodborne Pathogens in 35 Foodborne Outbreaks Using Multiplex Real-Time SYBR Green PCR Analysis," Hindawi Publishing Corporation, International Journal of Microbiology, vol. 2010, pp. 1-18.
Narayanan Jothikumart et al., "Rapid Detection of *Escherichia coli* O157:H7 with Multiplex Real-Time PCR Assays," Applied and Environmental Microbiology, Jun. 2002, vol. 68, No. 6, pp. 3169-3171.

* cited by examiner

*Primary Examiner* — Kenneth R. Horlick
*Assistant Examiner* — David Thomas
(74) *Attorney, Agent, or Firm* — Hogan Lovells US LLP

(57) ABSTRACT

Disclosed are novel primers for use in the molecular detection of food-threat agents and food-borne pathogens. The primers may be used in combination for the rapid, high-throughput screening PCR-based techniques to simultaneously detect multiple food safety biothreat agents. The multiplex-detection methods have improved sensitivity and specificity for the detection of multiple high-impact food-borne pathogens simultaneously. Real-time PCR assaying techniques using such primers include microarrays and multiplex single-tube arrays, the latter optionally simultaneously with TaqMan probes.

15 Claims, 44 Drawing Sheets
(20 of 44 Drawing Sheet(s) Filed in Color)

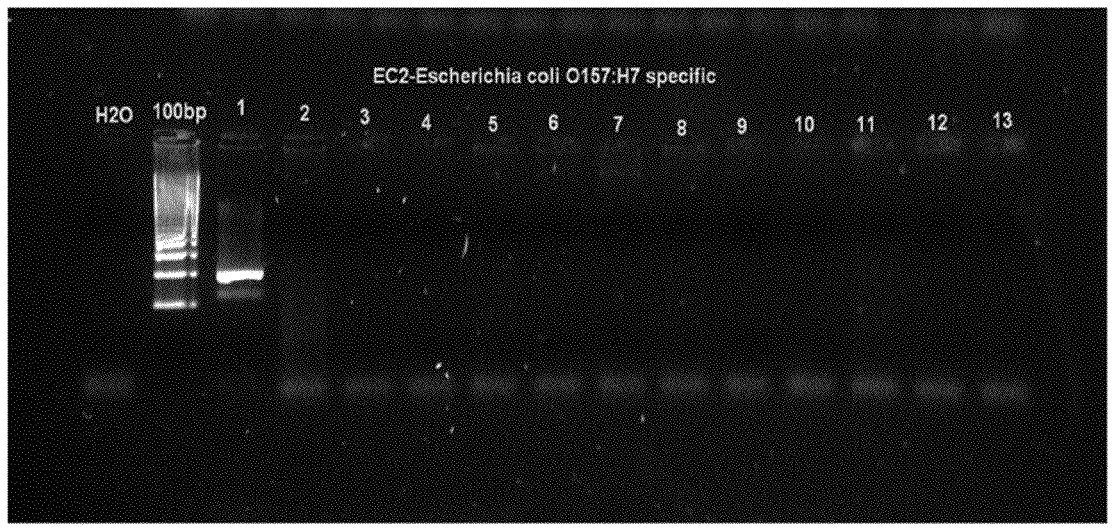
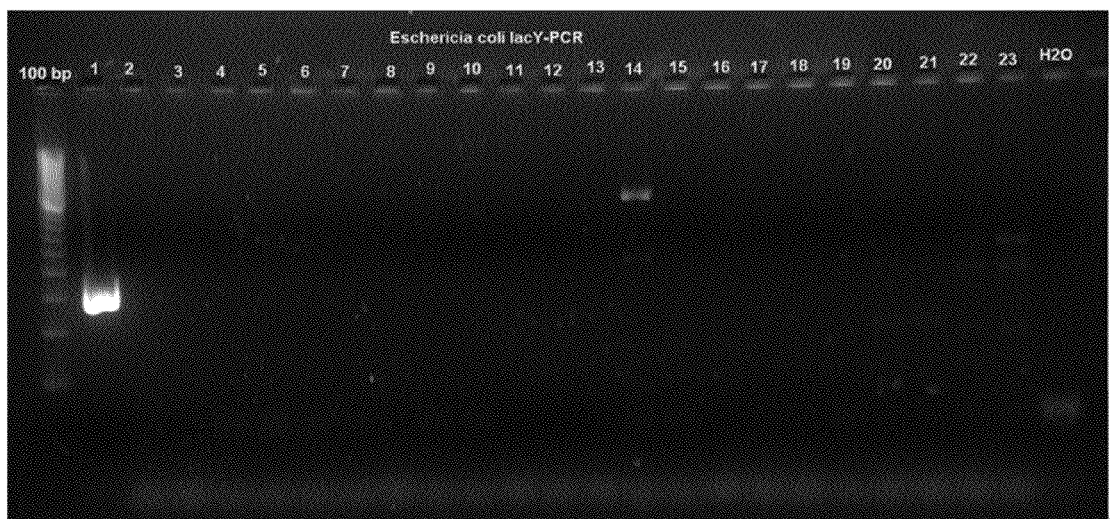
FIG. 2A

F. tularensis subsp. tularensis

All Francisella species

FIG. 2B

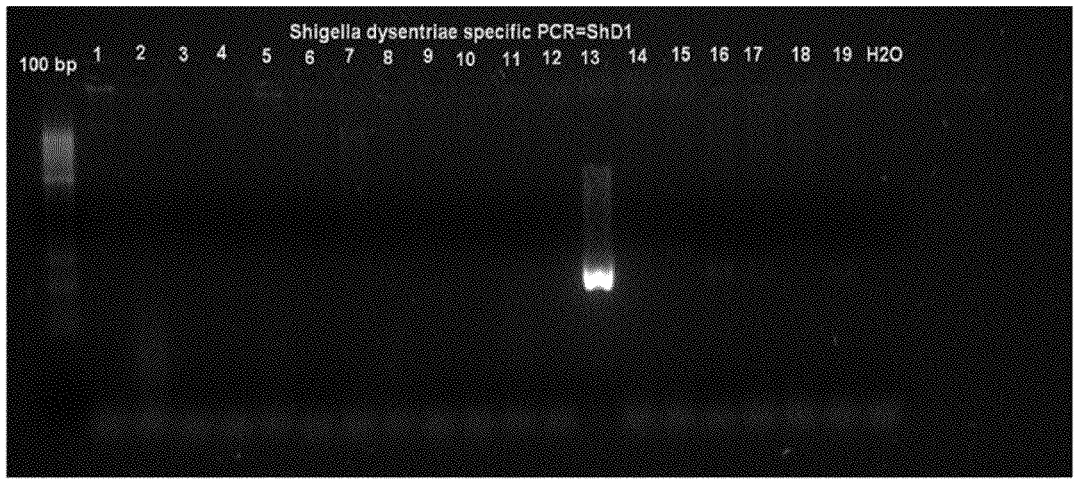
*Shigella dysentriae*
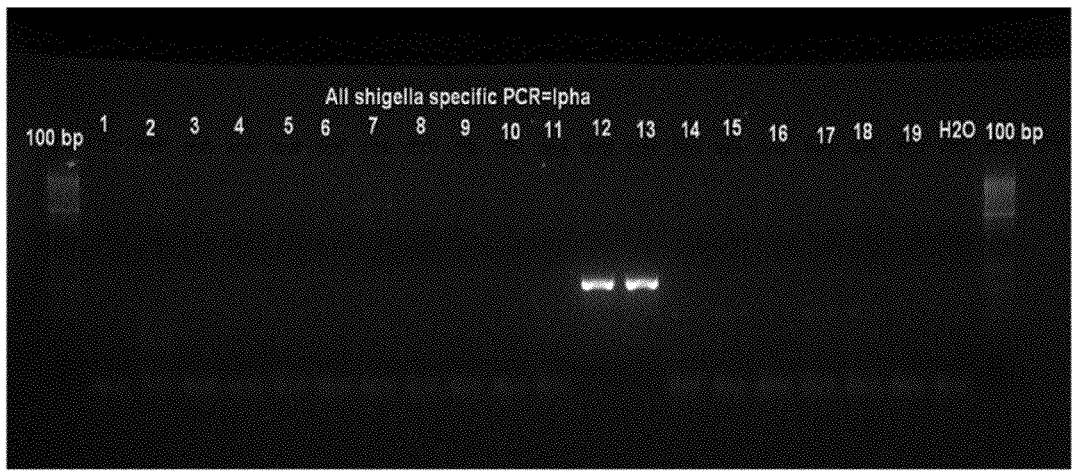
All *Shigella* species
FIG. 2C

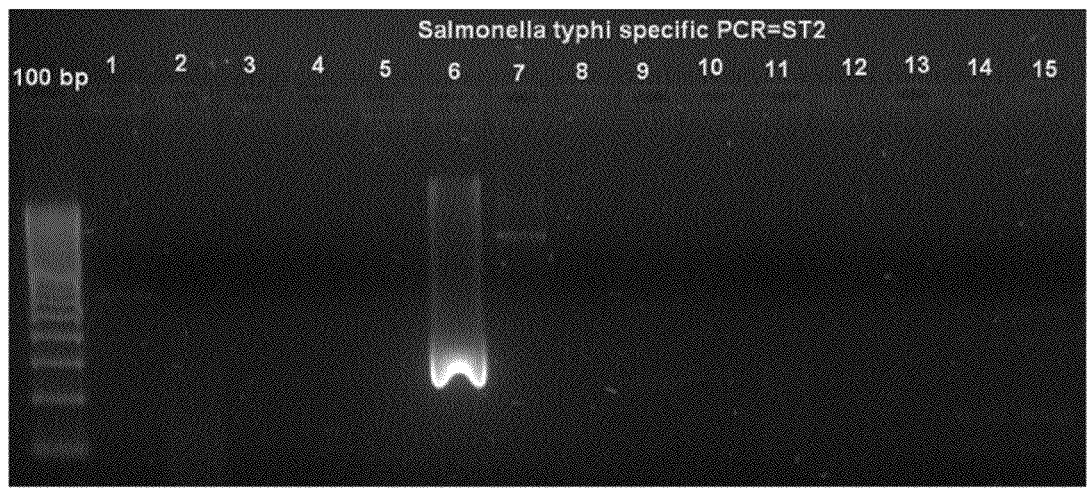
*Salmonella typhi*
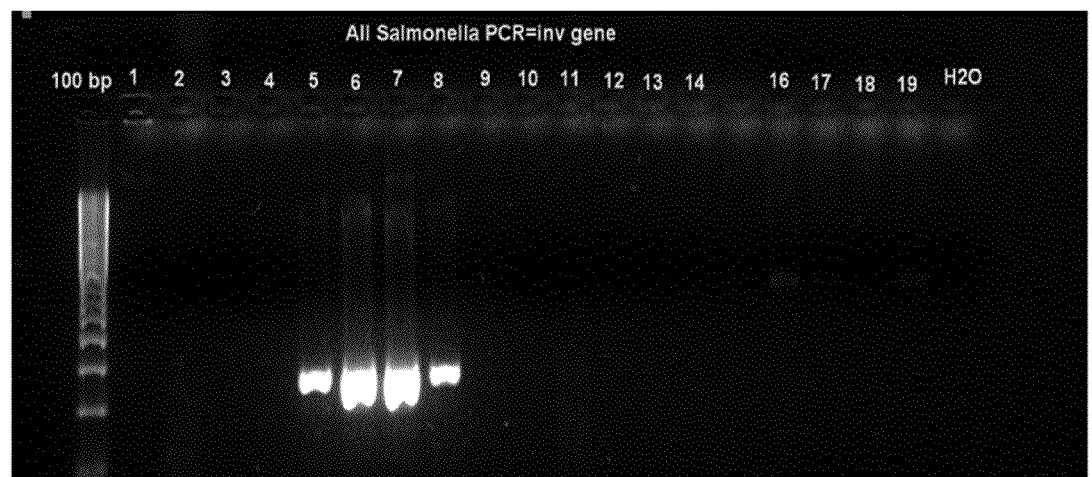
All *Salmonella* species
FIG. 2D

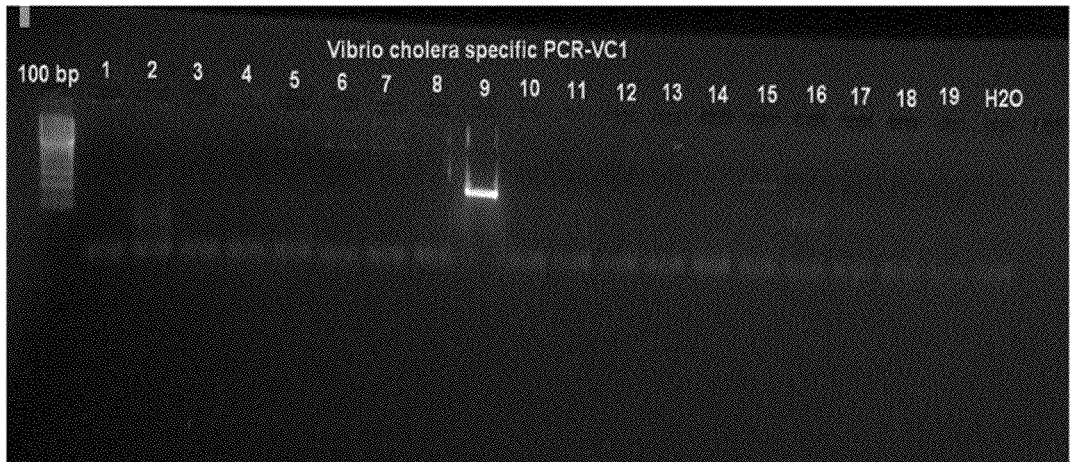
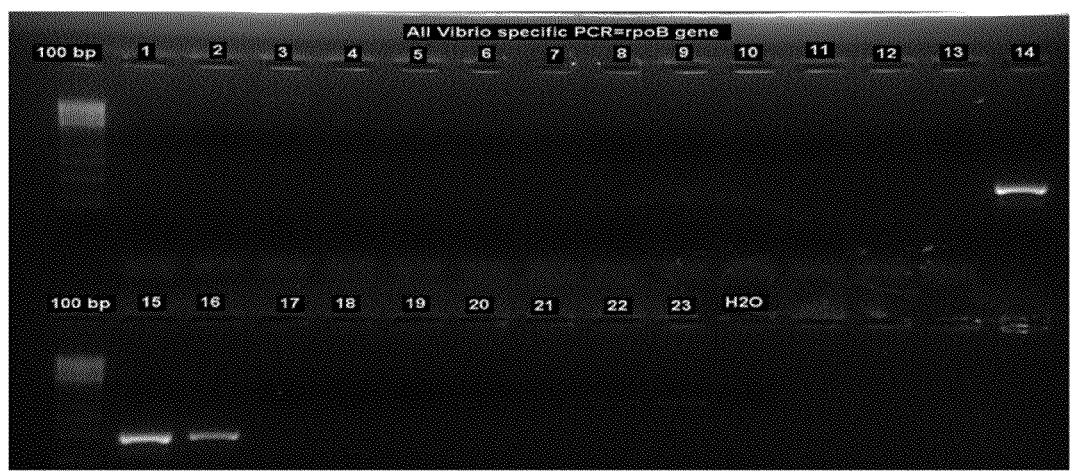
FIG. 2E

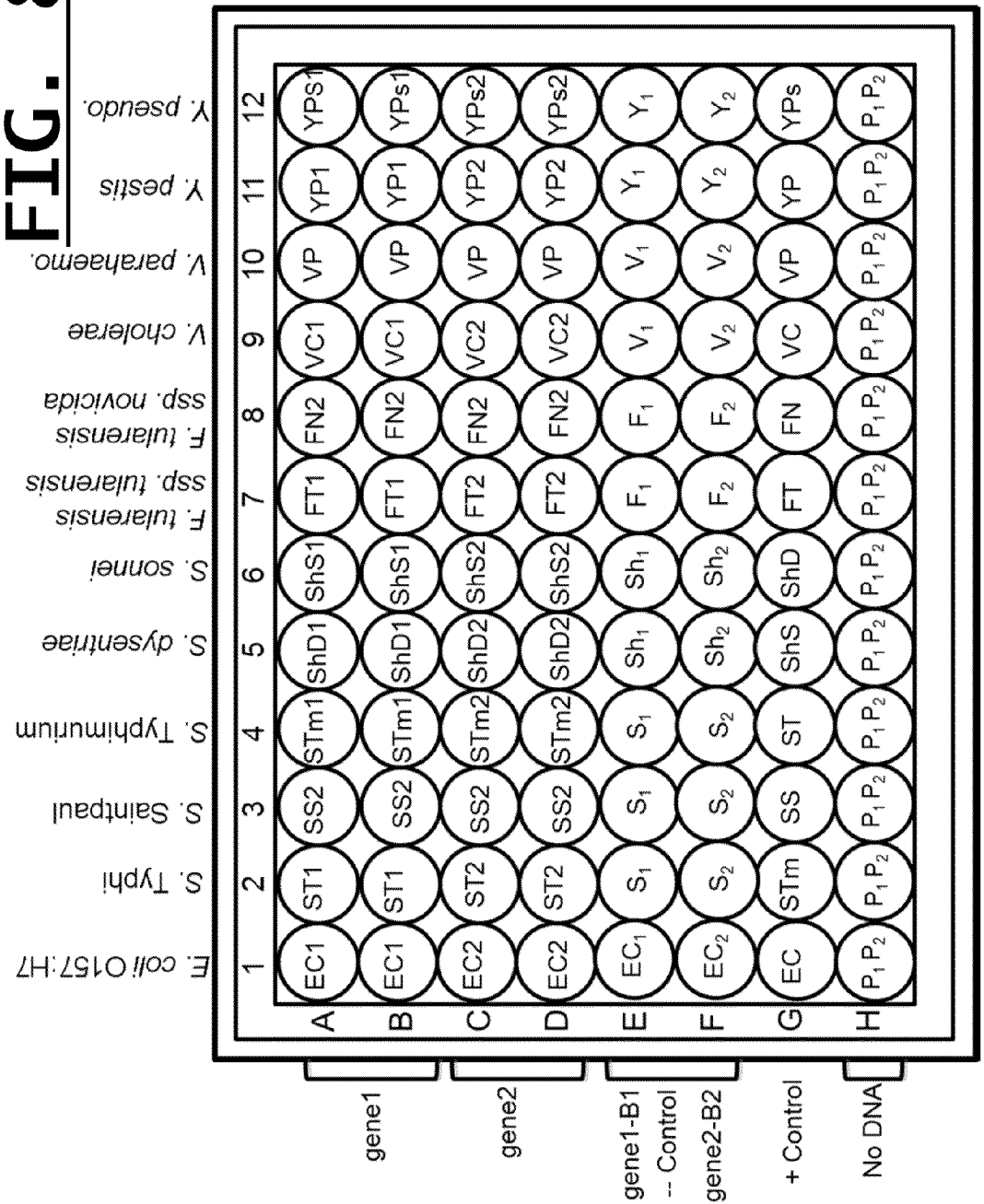

DETECTION OF FOOD THREAT AGENTS AND FOOD-BORNE PATHOGENS

STATEMENT REGARDING FEDERALLY SPONSORED RESEARCH OR DEVELOPMENT

This invention was made with government support under grant award number 2007-ST-061-000003 awarded by the Department of Homeland Security and G12RR003059 awarded by the National Center for Food Protection and Defense. The government has certain rights in the invention.

FIELD OF THE INVENTION

The present invention relates to the molecular detection of food-threat and frequently encountered food-borne pathogens. More particularly, the present invention relates to methods, kits, and assays for the rapid and accurate detection of bioagents of particular public health interest that may be carried in food using novel primers for use in PCR and other genetic screening methodologies.

BACKGROUND OF THE INVENTION

Gastroenteritis is used in the medical field to refer to patient infection or irritation of the digestive tract, particularly the stomach and intestine. Commonly, it may be referred to as "stomach flu" even though it is not related to influenza, or as "food poisoning." Major symptoms include nausea and vomiting, diarrhea, and abdominal cramps, which can be accompanied by fever and overall weakness. While gastroenteritis does not normally pose significant threats to otherwise-healthy adults, children, the elderly, and persons with certain existing diseases are more vulnerable to dehydration and other complications.

Acute cases of gastroenteritis affect millions of persons per year in the U.S., and an estimated 22% to 30% of these cases are thought to be caused by food-borne disease or pathogens (i.e., "food poisoning"). For example, it has been reported that globally 1.3 billion cases of salmonellosis, food poisoning resulting from exposure to *Salmonella enterica*, occur annually, resulting in approximately 3 million deaths. While most otherwise healthy adults recover from such food poisoning within a few days of exposure, the symptoms can be at least temporarily debilitating. Because of the debilitating potential of acute gastroenteritis, bioterrorism through deliberate adulteration of a food supply using common, or, alternatively, more rare and deadly, pathogens poses a significant potential threat to national security. Given the wide variety of potential chemical and biological agents, contaminating food is perhaps one of the easiest means to intentionally introduce adulterants at many vulnerable points along the food supply continuum. Although all the diverse possibilities for food-borne bioterrorism cannot be specifically prevented, strategic preparations for surveillance, diagnosis, outbreak investigation, and medical response could mitigate foodborne threats of any origin.

A deliberate attack on the food supply is plausible and potentially catastrophic both economically as well as in loss of life. The major steps in meeting food defense goals include increasing preparedness, developing response plans and ensuring that we have tools to facilitate recovery. Principal among these tools would be a rapid, high-throughput screening technique to simultaneously detect and identify multiple food safety threat agents. Preferably, such tools should be capable of at least detecting selected bacterial agents having the potential for catastrophic public and economic consequences. Further, such tools should be able to provide reliable detection techniques to identify high-impact pathogenic agents in human food supply systems, before the agents reach the consumer.

Organisms listed in the national notifiable disease surveillance system and/or food-borne disease active surveillance system that have potential for use in bioterrorism include, for example, *Escherichia coli* O157:H7, *Shigella dysenteriae*, *Salmonella enterica* ssp. enterica (including serovars *Typhi*, Typhimurium, and Saintpaul) *Francisella tularensis* ssp. tularensis, *Francisella tularensis* ssp. *novicida*, *Vibrio cholerae*, *Vibrio parahaemolyticus*, *Shigella sonnei*, *Yersinia pestis*, and *Yersinia pseudotuberculosis*. The food threat agents *Escherichia coli* O157:H7, *Salmonella*, *Shigella*, *Yersinia*, and *Vibrio cholerae* have each been designated by the Centers for Disease Control and Prevention as high-impact food safety threat agents. Further, *Francisella tularensis* (henceforth, "*F. tularensis*") is one of the most infectious pathogenic bacteria known, requiring inoculation or inhalation of as few as 10 organisms to cause extreme infectivity and having substantial capacity to cause illness and death. This feature and the capacity of the organism to survive outside of a mammalian host for weeks gives *F. tularensis* dangerous potential for use as a biological weapon (Kaufmann, Meltzer, Schmid, 1997; WHO, 2007).

Presently, there are no commercially viable mechanisms for wide and accurate screening and/or monitoring of the food supply for biothreat agents and food-borne pathogens. No single molecular diagnostic test is so far available to detect multiple food threats at once. Any viable mechanism would need not only to identify the presence of a potential agent with a high degree of sensitivity and accuracy, but also need to be able to identify exactly what agents are present. Preferably, any mechanism should be capable of identifying bio-threat agents from their closely related variants for the purpose of classifying and tracing the origin of contamination.

For example, because of their close evolutionary relationship, differentiation of *Escherichia* from *Shigella* species poses a big challenge (Jin et al., 2002; Pupo et al., 2000). Further, distinguishing within a genus, species, or subspecies can be just as challenging, such as in the case of distinguishing among *Shigella sonnei* from other members of its genus. In addition, certain organisms posing the potential to be food-borne bio-threat agents share extreme genome similarity with less threatening organisms, such as is the case with the highly virulent *F. tularensis* ssp. tularensis in comparison to the genetically similar, but less threatening to humans, *F. tularensis* ssp. mediastatica. In other instances, a complete genome sequence database is unavailable, making it difficult to localize specific regions within the genome, such as in the case of *Salmonella enterica* ssp. enterica serovar Saintpaul. The genomes of different strains of this serovar are not well characterized making it hard to develop molecular detection tools. Thus, the most common and/or concerning food threat bioorganisms are not presently easily detected and identified.

Additionally, any screening and monitoring mechanism must be simple to operate, and preferably should be able to detect and identify multiple target agents simultaneously. While research has considered multiplexed or simultaneous PCR-based molecular detection assays for food screening, heretofore there has not been successful adaptation of PCR technologies to food screening. One of the known challenges in multiplexed or simultaneous PCR-based molecular detections is the need for optimization of the reactions conditions such as annealing temperatures optimal for all primer sets, avoiding primer dimers, generation of compatible amplicon sizes, and adjustment for different amplification efficiencies (Edwards and Gibbs, 1994). Simply, adjusting the PCR for detecting one agent will oftentimes make it incompatible for simultaneous detection of another agent. This is especially complicated when the sample tested for contamination is a food product.

In particular, food matrices provide a critical challenge in amplification-based pathogen detection approaches. Because of potential spoilage, pre-analytical sample processing techniques are needed to reduce the time needed to arrive at diagnosis and decision-making (Benoit and Donahue, 2003; Dwivedi and Jaykus, 2011). Further, certain genetically-based detection mechanisms will not discriminate between live and dead organisms, with sterilized products containing non-viable bacteria or their DNA yield positive results on screening tests. Previous attempts have been made to develop multiplexed PCR assays that can simultaneously detect multiple food-borne pathogens (Fukushima et al., 2010; Jothikumar and Griffiths, 2002; Skottman et al., 2007; Wilson et al., 2005). None of those attempts were able to produce an assay that can detect and identify the primary food threat agents of bioterrorism potential, and none identified highly specific targets capable of discriminating a broad range of pathogens or related bacteria. Highly specific primer sequences are not available for all biothreat organisms of interest which primers are highly specific when tested against a wide array of organisms while also being suitable for simultaneous or multiplex detection of those organisms.

Thus, there remains a need in the art for methods, kits, and assays for the simultaneous, rapid and accurate detection and identification of multiple bio-threat agents that may be present in food.

SUMMARY OF THE INVENTION

In light of the above needs, it is an object of one or more embodiments of the present invention to identify primers that may be used to identify certain bio-threat agents that may be present in food.

Furthermore, it is an object of one or more embodiments of the present invention to provide methods for molecularly detecting certain pathogens in food.

Additionally, it is an object of one or more embodiments of the present invention to provide simultaneous detection and identification of multiple high importance bio-threat agents that may be present in a sample, such as a food product sample, such as through molecular detection via multiplex PCR or PCR-micorplate array tests.

The various embodiments of the present invention achieve these and other objects via the discovery of novel primers for use in the molecular detection of bio-threat agents, where the primers may be used in combination for the rapid, high-throughput screening PCR-based techniques to simultaneously detect multiple food safety biothreat agents. The multiplex-detection methods performed in embodiments of the present invention have improved sensitivity and specificity for the detection of multiple high-impact food-borne pathogens simultaneously. Primers are provided herein that detect with high specificity and sensitivity certain bacterial agents that pose potential catastrophic public health and economic consequences, and thus those primers may be used reliable detection techniques as described herein to identify high-impact pathogenic agents in human food supply systems before the agents reach the consumer. Various embodiments of the present invention utilize amplifiable PCR product sizes, allowing the methods to also be useful in the identification of agents and their closely related variants for the purpose of classifying and tracing the origin of contamination.

The organisms for which primers have been identified in embodiments of the present invention include six primary food threat agents, namely the particular bio-threat relevant species, subspecies, serovars, and/or strains of *Escherichia*, *Shigella*, *Francisella*, *Salmonella*, *Vibrio* and *Yersinia*. Applicants have also identified PCR conditions that are suitable for the amplification of 203 bp to 345 bp fragments from all the six pathogens under the same reaction conditions, thus making the primers thus identified suitable for combined use under those reaction conditions in multiple simultaneous PCR to detect and identify those food threat agents.

The novel primers described herein were developed through extensive genomic data mining and multiple layer validation of the organisms, by which the Applicants identified new target sequences which are believed to provide the detection methods and platforms herein with improved specificity. While some of these targets have putative functions, others have hitherto unknown functions. For each of the organisms selected, Applicants obtained genome sequences for the organisms from the National Center for Biotechnology Information, associated with the U.S. National Institutes of Health, and a BLAST search was used in selecting target regions. Specific new and novel primers were then designed from regions uniquely found in the specific agents of interest, including regions corresponding to either hypothetical or putative proteins the functions of which have not been clearly defined. All primers were analyzed in-silico for specific binding across the genome sequence of strains of the targets and similar species using the virtual tool accessible at http://in-silico.ehu.es/PCR/ and the V-NTI Advanced 11 tool (Invitrogen, USA). Virtual PCR results provided an initial indication regarding the specificity of the developed primers for the biothreat agent organisms, and conventional PCR specific amplification from different organisms species was confirmed the in-silico findings.

Further, the specificity of the primers identified by Applicants were tested and validated against a broad array of potential food threat agents and related species or strains, which do not pose the same (or, potentially, any) threat. For example, primers described herein which were developed by Applicants for detecting *Francisella tularensis* (herein abbreviates as "*F. tularensis*") ssp. tularensis, designed from a hypothetical protein gene pdpD2, were tested against 4 other subspecies (holartica, novicida, mediasiatica) and the closely related *Francisella philomiragia*, and showed reactivity only to the *F. tularensis* ssp. *tularensis*. Likewise, primers described herein which were developed by Applicants for detecting *F. tularensis* ssp. novicida based on another gene for hypothetical protein pdpD were found to be specific to that subspecies; it did not detect any of the other three *F. tularensis* subspecies.

Each of the above identified primers and primer pairs were verified first by in-silico PCR and by in-vitro differential identifications under identical PCR conditions against genomic DNA preparations from 23 species representing six food threat agents (*E. coli* O157:H7 strain EDL 933, *Shigella dysenteriae, Salmonella enterica* serovar Typhi, *Francisella tularensis* subspecies tularensis, *Vibrio cholerae*, and *Yersinia pestis*) and six foodborne pathogens (*Salmonella enterica* serovar Typhimurium, *Salmonella enterica* serovar Saintpaul, *Shigella sonnei, Francisella tularensis* ssp. novicida, *Vibrio parahaemolyticus* and *Yersinia pseudotuberculosis*). Each pathogen was specifically identifiable at the genus, species, and subspecies levels, as appropriate, in both conventional and real-time PCR without false positives for other related organisms. Sensitivity assays performed also confirmed usefulness of the primers for detection of small amounts of target DNA. These results evidence that Applicants invention comprises a suitable platform to simultaneously detect small amounts of foodborne pathogen and threat agents specifically and in real-time.

Thus, for the first time Applicants have identified primers for major biothreat agents that may be readily combined into common assays for the rapid and accurate detection of primary food threat agents of bioterrorism potential, which assays are capable of discriminating a broad range of pathogens or related bacteria. The primers are identified fully below.

The various primers identified above may be used alone to detect and identify a selected bio-agent, or may be used in combination and/or tandem to detect and identify whether any of a plurality of bio-threat organisms are present in a sample. When used in tandem or combination, on preferred embodiment of the invention comprises using primer pairs designed for detecting two or more different bio-threat agents in a common PCR-microplate array or, alternatively, in a one-tube multiplex PCR. In such embodiments, the various different primer pairs are selected such that all utilized pairs can operate under the same conditions (e.g., melting temperatures) such that the PCR process can be run in simultaneously on the macroarray or one-tube array. Most preferably, the macroarrays and/or multiplex one-tube arrays contain primer pairs sufficient to detect and identify six or more biothreat agents simultaneously. Further, particularly with respect to multiplex one-tube PCR, such embodiments can optionally use different probes specific to the target gene containing different dyes of different emission capacity to assist in multiplex detection.

One particular preferred embodiment of the invention comprises customized PCR-micorplate arrays of 96, 48 or 63 wells useful for the rapid identification of six select food threat agents, *Escherichia coli* O157:H7, *Francisella tularensis*, *S. enterica* ser. Typhi, *Shigella dysenteriae*, *Yersinia pestis* and *Vibrio cholerae* and closely related six major food borne pathogens *S. enterica* ser. Typhimurium, *S. enterica* ser. Saintpaul, *F. tularensis* ssp. novicida, *Vibrio parahaemolyticus*, *Yersinia pseudotuberculosis*. These PCR-microplate arrays contain suitable primers for the agents and pathogens such that the same PCR conditions may be used to run all the samples of the three different plates for analysis under real-time PCR. Thus, these PCR-microplate arrays constitute a rapid (e.g., less than 1 hr overall testing time), high-throughput screening PCR-macro-array technique to simultaneously detect multiple bio-organisms that pose food safety threats.

Additional embodiments of the invention include handheld devices for point-of-use detection using SPR and impedimetric technologies. Such hand-held devices would be suitable, for example, in use for the detection of common food-borne pathogens at industrial and small scale farming levels.

The various embodiments of the invention having thus been generally described, several illustrative embodiments will hereafter be discussed with particular reference to several attached drawings and in view of various experimental examples.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 2F:
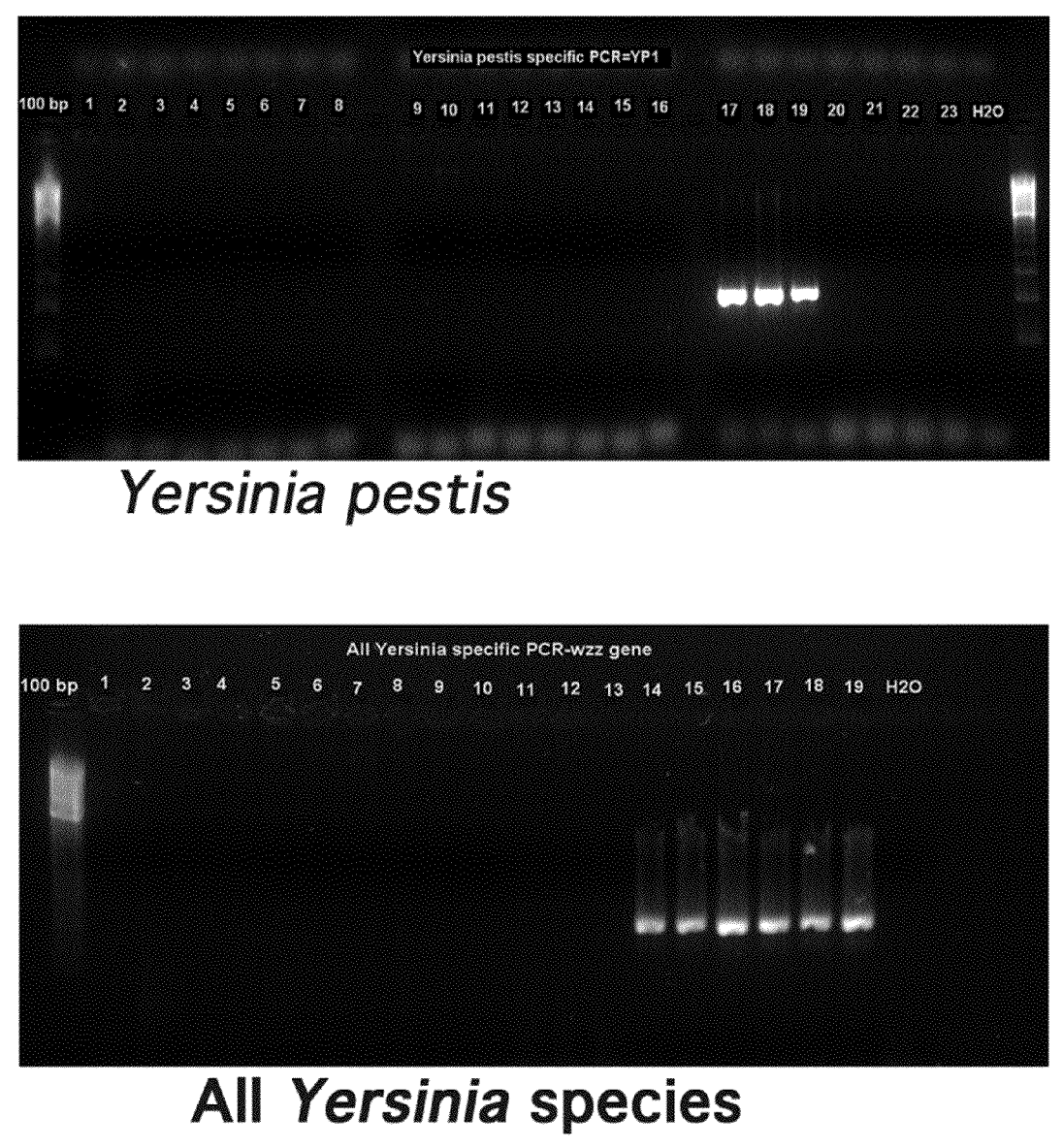

FIG. 2A through 2F are black and white photographs of various gels obtained from conventional PCR under equivalent conditions for various primers according to embodiments of the invention, which photographs illustrate validation of those primers as having a very specific detection profile capable of discriminating its target organism from other organisms having similar genomes.

FIG. 8A is a schematic drawing of a multi-well PCR-microplate array according to one preferred embodiment of the invention, while

FIG. 9A is a schematic drawing of a multi-well PCR-microplate array according to a second preferred embodiment of the invention, while

FIG. 10A is a schematic drawing of a multi-well PCR-microplate array according to a third preferred embodiment of the invention, while

DETAILED DESCRIPTION OF THE PREFERRED EMBODIMENTS

Figure 1A:
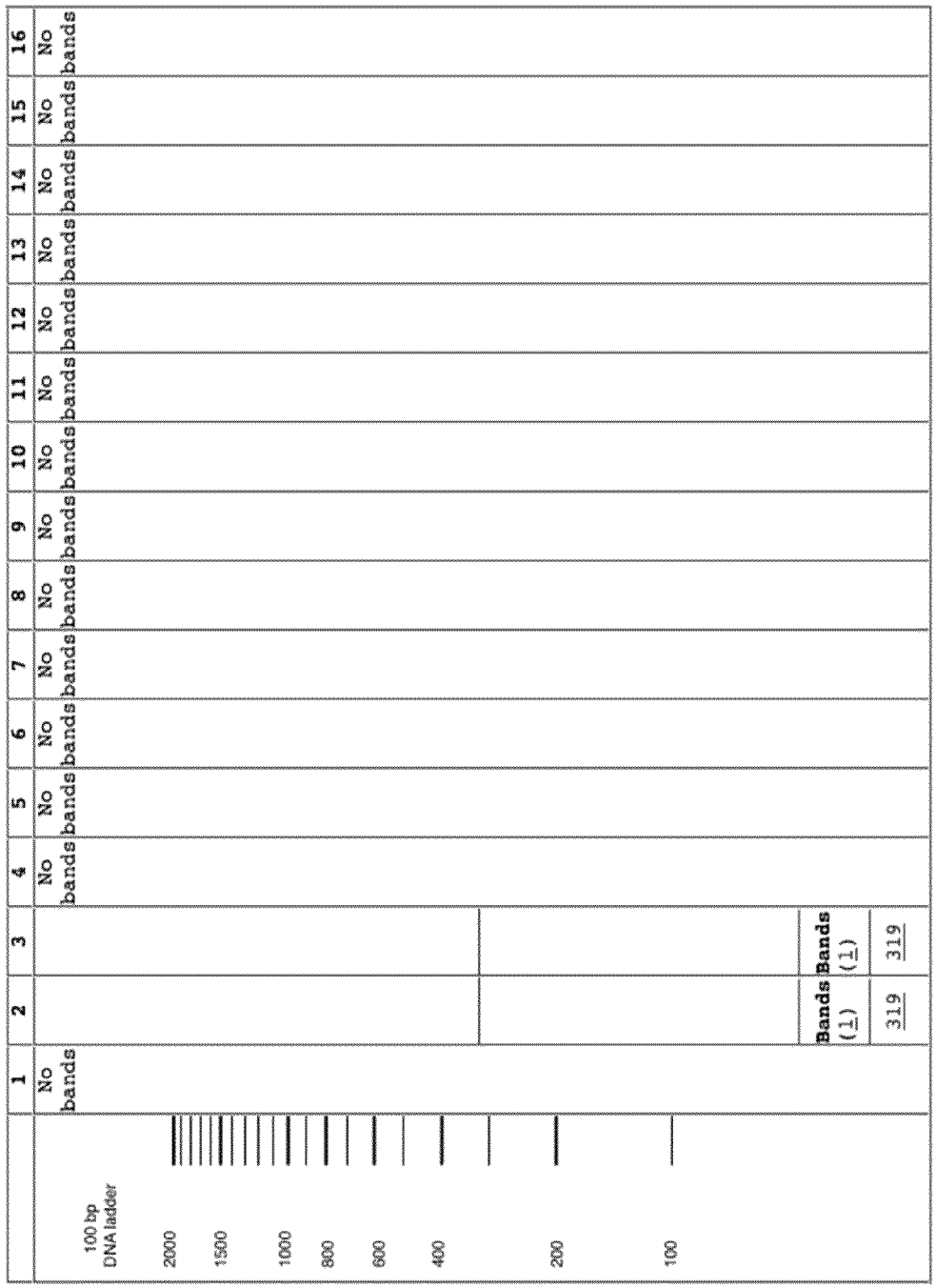
FIG. 1A and FIG. 1B are depictions of in-silico PCR amplification results for primers of the present invention for the target organisms *Salmonella enterica* ssp. enterica *serovar Typhi* and *Francisella tularensis* ssp. tularensis, respectively.

Various bacterial strains used in the experiments herein are listed in Table 1 below. Most of the genomic DNAs of all organisms listed in Table 1, except for *F. tularensis* ssp. novicida and *F. tularensis* ssp. tularensis, were purchased from ATCC collection (Manassas, Va.). The genomic DNA's of two *Francisella* subspecies were kindly provided by Dr. Karl Klose, University of Texas at San Antonio STCEID. Genomic DNAs of strains, *F. tularensis* ssp. novicida KM145, *Y. pestis* ZE 94-2122, *Y. pestis* A1122 BEI, *Y. pestis* KIM+, *Y. pseudotuberculosis* P62, and *Y. enterocolitica* Billups-1803-68 were obtained from Biodefense and Emerging Infections Research Resources Repository (BEI Resources). Laboratory biosafety level 2 organisms included *Shigella dysenteriae, Shigella sonnei*, and *Salmonella enterica* ssp. enterica serovar Saintpaul. The lists of bacterial species or strains included in this study to establish the PCR detection are given in Table 1.

Unless otherwise indicated herein, bioorganism samples utilized here were grown aerobically at 37° C. on tryptic soy agar supplemented with 5% horse blood and tryptic soy broth, with the exception of *Vibrio vulnificus* which, unless otherwise indicated, were grown at 30° C. For DNA extraction, unless otherwise noted herein, one ml of culture was collected by centrifugation at 10,000-x g, and pellet re-suspended in sterile 1×PBS solution. DNA was extracted according to the manufacturers procedure used in bacterial DNA extraction (Wizard genomic DNA purification kit, Promega).

Unless otherwise indicated herein in the various specific laboratory examples, all PCR reactions were set up in an isolated PCR station (AirClean Systems, NC) that was UV-sanitized daily and after each use.

After primers were initially designed, they were analyzed in-silico for specific binding across the genome sequence of strains of the targets in comparison to other similar species using the virtual tool accessible at http://insilico.ehu.es/PCR/ against all available whole genome sequences and partial sequences from prokaryote genome database of the NCBI. Further, primers were analyzed for potential to bind with different locations within the same whole genome sequence using the V-NTI 11 Advanced tool (Invitrogen, USA). Successful virtual PCR and V-NTI 11 primer motif binding

TABLE 1

| Species/Strain | CDC cat. | Origin |
|---|---|---|
| *Francisella* | | |
| *Escherichia coli* O157:H7 EDL933 | B | ATCC |
| *Escherichia coli* 1175 | | ATCC |
| *Francisella* | | |
| *Francisella tularensis* ssp. *tularensis* | A | Dr. Klose |
| *Francisella tularensis* ssp. *novicida* | | Dr. Klose |
| *Francisella tularensis* ssp. *novicida* KM145 | | BEI |
| *Francisella philomiragia* | | ATCC |
| *Salmonella* | | |
| *S. enterica* ssp. *enterica* serovar Braenderup ATCC ( ®BAA-664 ™) | | ATCC |
| *S. enterica* ssp. *enterica* ser. Typhimurium LT2 ATCC ® (700720D-5 ™) | B | ATCC |
| *S. enterica* ssp. *enterica* ser. Typhi Ty2 ATCC ( ®700931 ™) | B | ATCC |
| *S. enterica* ssp. *enterica* serovar Saintpaul 127 ATCC ( ®9712 ™) | B | ATCC |
| *Shigella* | | |
| *Shigella dysenteriae* ATCC ( ®11456a ™) | B | ATCC |
| *Shigella sonnei* ATCC ( ®11060 ™) | B | ATCC |
| *Vibrio* | | |
| *Vibrio cholerae* ATCC ( ®39315 ™) | B | ATCC |
| *Vibrio parahaemolyticus* EB 101 ATCC ( ®17802 ™) | | ATCC |
| *Vibrio vulnificus* Type strain Bio-group 1 ATCC ( ®27562 ™) | | ATCC |
| *Yersinia* | | |
| *Yersinia pestis* A1122 BEI (NR-15) | A | BEI |
| *Yersinia pestis* KIM10+ BEI (NR-642) | A | BEI |
| *Yersinia pestis* ZE 94-2111 | A | ATCC |
| *Yersinia pseudotuberculosis* P62 ATCC (29910) | B | BEI (NR-804) |
| *Yersinia pseudotuberculosis* NCTC 10275 ATCC (29833) | B | ATCC |
| *Yersinia enterocolitica* Billups-1803-68 ATCC (23715) | | BEI (NR-204) |
| *Yersinia enterocolitica* WA ATCC (27729) | | ATCC |

As noted above, primers are not available which are highly sensitive and specific while still being suitable for use in a simultaneous multi-organism array. As such, Applicants designed various primers as disclosed herein that would be suitable for use in simultaneous detection systems. To this end, Applicants used text mining, genomic data mining, sequence analysis and comparison tools to design the various primers listed in Table 2 below. All primers were independently designed based upon direct genomic information without earlier reference to other known primers. During the process of selection and design, the primers were initially validated for unique site recognition and strength of binding by using genomic DNA template of the respective organism. While some of the targets selected for these primers have putative functions, others have hitherto unknown functions. For each of the organisms selected, Applicants obtained genome sequences for the organisms and a BLAST search was used in selecting target regions. During design, Applicants also analyzed oligo-dimer and hair-loop characteristics of potential primer sequences in an effort to standardize primers to have similar melting temperatures, a prerequisite for simultaneous PCR usage.

search results were accepted as providing an initial indication regarding the specificity of the developed primers for target organisms from which they were designed. As noted below in Table 2, twelve of the specific genomic targets identified by Applicants in this effort to design the primers for *F. tularensis* ssp. tularensis, *F. tularensis* ssp. novicida, *S. dysenteriae*, *S. enterica* Typhimurium, *V. cholerae*, *Y. pestis*, and *Y. pseudotuberculosis* were in fact either hypothetical or putative proteins the functions of which have not been clearly defined.

By way of example, FIG. 1A shows the graphical output of an in-silico PCR amplification run using paired primers ST1-F-m-2 and ST1-R-m2 that were designed by Applicants from the genome for *S. enterica* ssp. *enterica* ser. Typhi Ty2. In FIG. 1A, the columns, numbered from left to right, show the in-silico PCR results against the following sixteen unique subspecies, serovars and strains for *S. enterica*: (1) *Salmonella enterica* ssp. enterica ser. Typhimurium LT2; (2) *Salmonella enterica* ssp. *enterica* ser. Typhi; (3) *Salmonella enterica* ssp. enterica ser. Typhi Ty2; (4) *Salmonella enterica* ssp. enterica ser. Paratyphi A str. ATCC 9150; (5) *Salmonella enterica* ssp. enterica ser. Choleraesuis str. SC-B67; (6) *Sal-* monella enterica ssp. enterica ser. Paratyphi B str. SPB7; (7) *Salmonella enterica* ssp. arizonae ser. 62:z4, z23:--; (8) *Salmonella enterica* ssp. enterica ser. Newport str. SL254; (9) *Salmonella enterica* ssp. enterica ser. Heidelberg str. SL476; (10). *Salmonella enterica* ssp. enterica ser. Schwarzengrund str. CVM19633; (11) *Salmonella enterica* ssp. enterica ser. Agona str. SL483; (12) *Salmonella enterica* ssp. enterica ser. Paratyphi A str. AKU_12601; (13) *Salmonella enterica* ssp. enterica ser. Dublin str. CT_02021853; (14) *Salmonella enterica* ssp. enterica ser. Gallinarum str. 287/91; (15) *Salmonella enterica* ssp. enterica ser. Enteritidis str. P125109; and (16) *Salmonella enterica* ssp. enterica ser. Paratyphi C strain RKS4594. As can be seen in FIG. 1A, only columns 2 and 3, corresponding to the serovars Typhi and Typhi Ty2 exhibited a positive in-silico PCR result for primers ST1-F-m-2 and ST1-R-m2. Thus, in-silico PCR indicated that such were strong candidates for use as PCR primers for detecting ser. Typhi strains without detecting other subspecies or serovars.

Figure 1B:
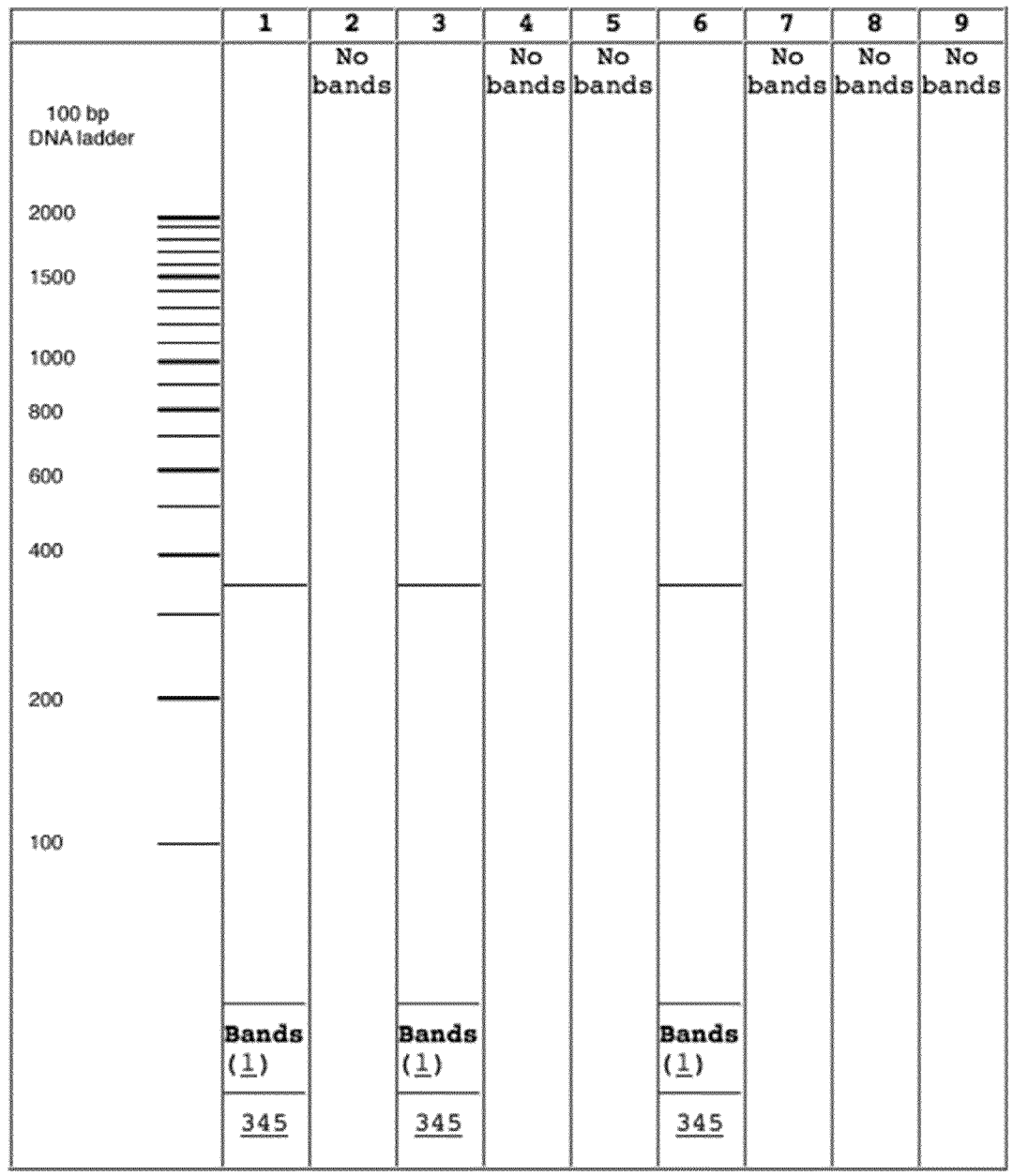

Similarly, FIG. 1B shows the graphical output of an in-silico PCR amplification run using paired primers FT1-F and FT1-R that were designed by Applicants from the genome of *Francisella tularensis* ssp. tularensis Schu4 to target the PdpD2 gene. In FIG. 1B, the columns, numbered from left to right, show the in-silico PCR results against the following nine unique species, subspecies, serovars and strains: (1) *Francisella tularensis* ssp. tularensis Schu4; (2) *Francisella tularensis* ssp. holarctica; (3) *Francisella tularensis* ssp. tularensis FSC 198; (4) *Francisella tularensis* ssp. holarctica OSU18; (5) *Francisella tularensis* ssp. novicida U112; (6) *Francisella tularensis* ssp. tularensis WY96-3418; (7) *Francisella tularensis* ssp. holarctica FTNF002-00; (8) *Francisella philomiragia* ssp. philomiragia ATCC 25017; and (9) *Francisella tularensis* ssp. mediasiatica FSC147. As shown, primers FT1-F and FT1-R showed positive PCR amplification for only columns 1, 3, and 6, which correspond to all of the *F. tularensis* ssp. tularensis strains tested, and a negative result was simulated for the other six tested organisms. Notably, a negative result was obtained for *F. philomiragia* ssp. philomiragia in addition to the different subspecies of *F. tularensis*. Thus, in-silico PCR indicated that primers FT1-F and FT1-R were strong candidates for use as PCR primers for detecting *F. tularensis* ssp. tularensis.

Similar in-silico PCR testing was performed following the design of each new primer pair by Applicants. For each primer pair that successfully passed in-silico PCR testing, Applicants performed conventional PCR amplification to validate the specificity of the primers for respective organisms. For this validation, DNA from 23 species representing major food-threat agents and closely related foodborne pathogens identified in Table 1 was used. Each PCR experiment was designed so that the primers were tested against their template DNA and DNA from the maximum number of closely related species under similar parameters. In parallel, genus inclusive primers were designed and PCR was performed to verify that the target species as well as other members of the genus could be detected. Genus inclusive primers gave an additional quality control to minimize cross reactivity with other genera or species within the genus.

Following this in-silico testing, Applicants primers as identified in Table 2 below were tested further using conventional PCR, in real-time PCR, and in multiplex single-tube PCR. In table 2, any primers having the word "All" built into the name is genus-inclusive (used by Applicants for testing specificity of other primers), while in the "Target Gene" column "H.P." stands a hypothetical protein, "I.M.P." denotes inner membrane protein, and "RloF" is a putative protein of unknown function. The suitability of the various species, subspecies and serovar/strain specific primers designed by Applicants for both highly selective and highly sensitive use was confirmed, as described in the various examples and experiments below.

TABLE 2

| Primer Name | SEQ. ID NO. | Target Bacterial Organism | Target Gene | Amplicon Size |
|---|---|---|---|---|
| EC2-SLT-R-m | 1 | *Escherichia coli* O157:H7 EDL933 | Stx2 | 201 bp |
| EC2-SLT-F-m | 2 | *Escherichia coli* O157:H7 EDL933 | Stx2 | 201 bp |
| EC1-Rm | 3 | *Escherichia coli* O157:H7 str EC4115 | Stx2A | 256 bp |
| EC1-Fm | 4 | *Escherichia coli* O157:H7 str EC4115 | Stx2A | 256 bp |
| lacY-ecoli-F | 5 | *Escherichia coli* CFT073 | lacY | 331 bp |
| lacY-ecoli-R | 6 | *Escherichia coli* CFT073 | lacY | 331 bp |
| FT1-F | 7 | *Francisella tularensis* subsp. tularensis Schu4 | PdpD2 | 345 bp |
| FT1-R | 8 | *Francisella tularensis* subsp. tularensis Schu4 | PdpD2 | 345 bp |
| FT2-mR | 9 | *Francisella tularensis* subsp. tularensis Schu4 | HP | 234 bp |
| FT2-mF | 10 | *Francisella tularensis* subsp. tularensis Schu4 | HP | 234 bp |
| FN2-F-m | 11 | *Francisella tularensis* subsp. novicida U112 | PdpD | 214 bp |
| FN2-R-m | 12 | *Francisella tularensis* subsp. novicida U112 | PdpD | 214 bp |
| All F-R-m | 13 | *Francisella tularensis* subsp. holarctica OSU18 | fusA | 371 bp |
| All F-F-m | 14 | *Francisella tularensis* subsp. holarctica OSU18 | fusA | 371 bp |
| ShD1-F | 15 | *Shigella dysenteriae* Sd197 | Z5694-like protein | 270 bp |
| ShD1-R | 16 | *Shigella dysenteriae* Sd197 | Z5694-like protein | 270 bp |
| ShD2-F-m | 17 | *Shigella dysenteriae* Sd197 | HP | 231 bp |
| ShD2-R-m | 18 | *Shigella dysenteriae* Sd197 | HP | 231 bp |
| rhsA-y-Sonnei-F | 19 | *Shigella sonnei* Ss046 | rhsA | 303 bp |
| rhsA-y-Sonnei-R | 20 | *Shigella sonnei* Ss046 | rhsA | 303 bp |

TABLE 2-continued

| Primer Name | SEQ. ID NO. | Target Bacterial Organism | Target Gene | Amplicon Size |
|---|---|---|---|---|
| ipaH-F | 21 | Shigella sonnei Ss046 | ipaH | 234 bp |
| ipaH-R | 22 | Shigella sonnei Ss046 | ipaH | 234 bp |
| Inv-F | 23 | Salmonella enterica subsp. enterica serovar Typhimurium LT2 | invC | 235 bp |
| Inv-R | 24 | Salmonella enterica subsp. enterica serovar Typhimurium LT2 | invC | 235 bp |
| ST1-F-m-2 | 25 | Salmonella enterica subsp. enterica serovar Typhi Ty2 | cI phage immunity repressor protein | 319 bp |
| ST1-R-m2 | 26 | Salmonella enterica subsp. enterica serovar Typhi Ty2 | cI phage immunity repressor protein | 319 bp |
| STM1-F-M | 27 | Salmonella enterica subsp. enterica serovar Typhimurium LT2 | I.M.P. | 229 bp |
| STM1-R-M | 28 | Salmonella enterica subsp. enterica serovar Typhimurium LT2 | I.M.P. | 229 bp |
| STM2-R-M | 29 | Salmonella enterica subsp. enterica serovar Typhimurium LT2 | DNA repair ATPase | 189 bp |
| STM2-F-M | 30 | Salmonella enterica subsp. enterica serovar Typhimurium LT2 | DNA repair ATPase | 189 bp |
| SS2-F-n | 31 | Salmonella enterica subsp. enterica serovar Saintpaul SARA23 | RloF | 312 bp |
| SS2-R-n | 32 | Salmonella enterica subsp. enterica serovar Saintpaul SARA23 | RloF | 312 bp |
| VC1-pho-F | 33 | Vibrio cholerae M66-2 chromosome I | Phosphor-tyrosine protein phosphatase | 212 bp |
| VC1-pho-R | 34 | Vibrio cholerae M66-2 chromosome I | Phosphor-tyrosine protein phosphatase | 212 bp |
| VC2-B-tox-R | 35 | Vibrio cholerae O1 biovar El Tor str. N16961 | Enterotoxin subunit B | 239 bp |
| VC2-B-tox-F | 36 | Vibrio cholerae O1 biovar El Tor str. N16961 | Enterotoxin subunit B | 239 bp |
| VpH1-F | 37 | Vibrio parahaemolyticus RIMD 2210633 | Thermo-stable hemolysin delta-VPH | 249 bp |
| VpH1-R | 38 | Vibrio parahaemolyticus RIMD 2210633 | Thermo-stable hemolysin delta-VPH | 249 bp |
| VpH2-F | 39 | Vibrio parahaemolyticus RIMD 2210633 | thrA | 105 bp |
| VpH2-R | 40 | Vibrio parahaemolyticus RIMD 2210633 | thrA | 105 bp |
| All-Vibrio-rpoBF | 41 | Vibrio vulnificus YJ016 | rpoB | 203 bp |
| All-Vibrio-rpoBR | 42 | Vibrio vulnificus YJ016 | rpoB | 203 bp |
| YP1-F-m2 | 43 | Yersinia pestis strain CO92 | Putative phage-related membrane protein | 206 bp |
| YP1-R-m2 | 44 | Yersinia pestis strain CO92 | Putative phage-related membrane protein | 206 bp |
| YP2-R-M3 | 45 | Yersinia pestis strain CO92 | H.P. | 241 bp |
| YP2-F-M2 | 46 | Yersinia pestis strain CO92 | H.P. | 241 bp |
| YPs1-F-M | 47 | Yersinia pseudotuberculosis IP 32953 | H.P. | 348 bp |
| YPs1-R | 48 | Yersinia pseudotuberculosis IP 32953 | H.P. | 348 bp |
| YPs2-R | 49 | Yersinia pseudotuberculosis IP 32953 | H.P. | 288 bp |
| YPs2-F | 50 | Yersinia pseudotuberculosis IP 32953 | H.P. | 288 bp |
| wzzR | 51 | Yersinia pseudotuberculosis IP 32953 | rfe | 211 bp |
| wzzF | 52 | Yersinia pseudotuberculosis IP 32953 | rfe | 211 bp |

Hereinafter, the various primers above may be individually referred to by the full name in Table 2 above, or may be generally referred to with its paired primer by a truncated name. For example, if Applicant hereafter refers to "primer VC2" or "primer pair VC2," that reference means primer VC2-B-tox-R (SEQ. ID NO. 35) and primer VC2-B-tox-F (SEQ. ID NO. 36).

In particular, after comparative genome analysis, genes rhsA and ipaH were identified for hypothetical proteins for the specific identification of Shigella sonnei (herein abbreviated "S. sonnei"), and primers were thereafter synthesized in conventional manner and tested for these genes. These primers designed by and confirmed as being useful by Applicants in embodiments of the present inventions for detecting S.

*sonnei* include the paired primers rhsA-y-Sonnei-F (depicted by SEQ. ID NO. 19) and rhsA-y-Sonnei-R (depicted by SEQ. ID NO. 20) and the paired primers ipaH-F (depicted by SEQ. ID NO. 21) and ipaH-R (depicted by SEQ. ID NO. 22). In PCR-based methods of the present invention, it is preferred that primers rhsA-y-Sonnei -F and rhsA-y-Sonnei-R are used for the detection of *S. sonnei*.

Similarly, *Salmonella enterica* ssp. enterica serovar Typhimurium (herein abbreviated as "S. Typhimurium") was identifiable by targets in the genes for putative proteins invC and IMP and the putative DNA repair ATPase. Primers according to the invention for detecting S. Typhimurium include the paired primers Inv-F (depicted by SEQ. ID NO. 23) and Inv-R (depicted by SEQ. ID NO. 24), the paired primers STM1-F-M (depicted by SEQ. ID NO. 27) and SMT1-R-M (depicted by SEQ. ID NO. 28), and the paired primers STM2-R-M (depicted by SEQ. ID NO. 29) and STM2-F-M (depicted by SEQ. ID NO. 30). In PCR-based detection and identification method embodiments of the present invention, it is preferred that primers STM2-R-M and STM2-F-M are used for the detection of S. Typhimurium.

On the other hand, while Applicants found that *Vibrio parahaemolyticus* (herein abbreviated as "*V. parahaemolyticus*") was identifiable using the hemolysin gene VP1729 and gene thrA, *Vibrio cholerae* (herein abbreviated as "*V. cholerae*") was identifiable using the gene for phosphotyrosine protein phosphatase VC0916 and the gene for enterotoxin subunit B as putative targets. The two *Vibrio* species thus could be distinguished in this manner.

In this regard, as listed in Table 2 below, primers according to the invention for detecting *V. parahaemolyticus* include the paired primers VpH1-F (depicted by SEQ. ID NO. 37) and VpH1-R (depicted by SEQ. ID NO. 38) and the paired primers VpH2-F (depicted by SEQ. ID NO. 39) and VpH2-R (depicted by SEQ. ID NO. 40), while it is preferred that primers VpH1-F and VpH1-R be used for the detection of *V. parahaemolyticus* in embodiments of the present inventions.

Likewise, primers according to the invention for detecting *V. cholerae* include the paired primers VC1-pho-F (depicted by SEQ. ID NO. 33) and VC1-pho-R (depicted by SEQ. ID NO. 34) and the paired primers VC2-B-tox-R (depicted by SEQ. ID NO. 35) and VC2-B-tox-F (depicted by SEQ. ID NO. 36), while it is preferred that primers VC1-pho-F and VC1-pho-R be used for the detection of *V. cholerae* in embodiments of the present inventions.

As such, primers according to the invention for detecting *F. tularensis* ssp. tularensis include the paired primers FT1-F (depicted by SEQ. ID NO. 7) and FT1-R (depicted by SEQ. ID NO. 8) for gene target PdpD2 and the paired primers FT2-mR (depicted by SEQ. ID NO. 9) and FT2-mF (depicted by SEQ. ID NO. 10) for gene target HP, while it is preferred that primers FT1-F and FT1-R be used for the detection of *F. tularensis* ssp. tularensis in embodiments of the present inventions. Likewise, primers according to the invention for detecting *F. tularensis* ssp. novicida include the paired primers FN2-F-m (depicted by SEQ. ID NO. 11) and FM2-R-m (depicted by SEQ. ID NO. 12).

Applicant also discovered primers based on the genes for putative phage-related membrane protein (YP02127) and the hypothetical protein YpAngola A2197 that are able to detect all *Yersinia pestis* (herein abbreviated as "*Y. pestis*") strains except the biovar Microtus strain 91001. However, although primers as discovered by Applicant's lack the ability to identify this organism, such is not envisioned as being a significant drawback as there is no evidence that human plague can arise from Microtus strains (Zhou et al., 2004). Furthermore subcutaneous inoculation of strains from serovar Microtus does not demonstrate virulence (Song et al., 2004).

Primers according to the invention for detecting *Y. pestis* strains other than Microtus 91001 include the paired primers YP1-F-m2 (depicted by SEQ. ID NO. 43) and YP1-R-m2 (depicted by SEQ. ID NO. 44) for target YP02127 and the paired primers YP2-R-M3 (depicted by SEQ. ID NO. 45) and YP2-F-M2 (depicted by SEQ. ID NO. 46) for target YpAngola A2197, while it is preferred that primers YP1-F-m2 and YP1-R-m2 be used for the detection of *Y. pestis* in embodiments of the present inventions.

Applicant also utilized genes for hypothetical proteins to serve as specific targets for the creation of primers for the identification of *Yersinia pseudotuberculosis* (herein abbreviated as "*Y. pseudotuberculosis*") isolates. While the targeting of hypothetical proteins for detection of the bacteria may not directly correlate with currently known pathogenicity or virulence of the organisms, genetic studies could be used to reveal the significance of these gene products in bacterial biology or host interaction, or even pathogenicity. The identification of these genomic regions as specific to the particular species or subspecies, as was done by Applicants here in the case of *Y. pseudotuberculosis*, allows known molecular pathogen detection techniques to be used by providing additional targets for amplification.

Primers according to the invention for detecting *Y. pseudotuberculosis* include the paired primers YPs1-F-M (depicted by SEQ. ID NO. 47) and YPs1-R (depicted by SEQ. ID NO. 48), the paired primers YPs2-R (depicted by SEQ. ID NO. 49) and YPs2-F (depicted by SEQ. ID NO. 50), and the paired primers wzzR (depicted by SEQ. ID NO. 51) and wzzF (depicted by SEQ. ID NO. 52). It is preferred that primers YPs1-F-M and YPs1-R be used for the detection of *Y. pseudotuberculosis* in embodiments of the present inventions.

Other preferred primers, and preferred uses of the primers in combination with other primers, are identified in the various experimental examples that follow.

EXAMPLE 1

The following experiment was performed to confirm the specificity of Applicants' designed primer pairs to detect by conventional PCR and gel electrophoresis only their intended food-borne pathogens and threat agents. For each of the primer pairs identified in Table 2, single target PCR was performed against the intended target and against one or more other closely related organisms. Additionally, this single target PCR experiment was repeated for the same group of organisms using a primer known to detect all of the organisms (e.g., a "genus-inclusive primer"), such as primers All-Vibrio or All-F in Table 2, or other genus-inclusive primers already known to those of ordinary skill in the art. In this manner, each of Applicants' designed primers was tested against its respective template DNA and DNA from the maximum number of closely related species.

PCR was conducted using a 25 µl final volume containing 0.2 µM of forward and reverse primers, 12.5 µl of Pwo Master mix containing 1.25 U of Pwo enzyme, 2 mM $MgCl_2$ and 0.2 mM dNTPs (Roche Diagnostics, Mannheim Germany). The PCR amplification profile for these assays consisted of 10 min at 95° C., followed by 30 cycles of 15 seconds at 95° C., 15 seconds at 60° C., and 15 seconds at 72° C. using Master cycler pro (Eppendorf, Humburg, Germany). Each primer pair was validated by confirming the presence of the expected single band in gel electrophoresis. PCR products were resolved on 1.5 agarose gels, and the gels were stained with GelRed (obtained from Biotium, of Hayward, Calif.) and photographed using AlphaImager (obtained from Cell Biosciences, of Santa Clara, Calif.). As exemplified in FIG. 2A through FIG. 2F, Applicants' new species-specific primers gave a very specific detection that discriminated each of the target species, whereas the genus-inclusive primers distinctively identified other members of the genus simultaneously with the target. Therefore, these conventional PCR data provided strong evidence that the primers were very specific under the experimental conditions employed.

In particular, FIG. 2A through FIG. F depict representative photographs for various ones of such gels obtained during this validation experiment using conventional PCR and gel electrophoresis. In FIG. 2A, the top photograph shows an exemplary gel for the detection of *E. coli* O157:H7 using the primers EC2-SLT-R-m and EC2-SLT-F-m, which is shown in comparison with the bottom photograph of the same organism being detected by a genus-inclusive primer. Only a minor cross reactivity of the *E. coli* genus specific primers with *Vibrio cholerae* was noticed in the assay using the genus-inclusive primer (see the weak band in column 14 of the bottom photo). However, the size of the product was larger than expected and also the intensity of the band was weak. In FIG. 2B, the top photograph shows an exemplary gel for gels run against both *F. tularensis* ssp. tularensis and ssp. novicida using the ssp. tularensis targeted primers FT2, and the bottom photograph for purposes of comparison shows a gel that utilized a genus-inclusive primer against these same *Francisella tularensis* subspecies. The photographs of FIG. 2C show in the top photograph a representative gel used to assay against the various *Shigella* species/strains of Table 1 using *S. dysenteriae* primers ShD1-F and SHD1-R, and in the bottom photograph a representative gel against the same species/strains using a genus-inclusive *Shigella* primer. As can be seen, the gel in the top photos of FIG. 2A and FIG. 2C have a single band visible while the bottom photos show two bands, indicating that, as intended, primers FT2-mR and FT2-mF detected ssp. tularensis and not ssp. novicida and that primers ShD1-F and SHD1-R detected *S. dysenteriae* but not *S. sonnei*. FIG. 2D shows two photographs each of representative gels, with the top photograph depicting a gel using primers STM2-R-M and STM2-F-M against *S. enterica* ssp. enterica serovars Typhi, Typhimurium, Saintpaul, and Braenderup while the bottom photograph shows a representative gel using a genus-inclusive primers for those serovars. Again, notably the top gel of FIG. 2D exhibits only a single bar (evidencing the detection of only the Typhi serovar as intended), in contrast to the four bars of the gel using the genus-inclusive primer. FIG. 2E provides a similar pair of representative gel photographs, with the top photograph showing a gel run against DNA for the various *Vibrio* species of Table 1 using *V. cholerae* targeted primers VC1-pho-F and VC1-pho-R, and the bottom photograph showing detection of the same DNA sample using a *Vibrio* genus-inclusive primer capable of detecting *V. cholerae, V. parahaemolyticus*, and *V. vulnificus*. Again, a similar result was obtained, with Applicants' primer resulting in only a single bar (see the top photograph of FIG. 2E) while the bottom photograph confirms with the presence of three bars (see bottom photograph of FIG. 2E at gel columns 14-16) that three *Vibrio* species were present in the sample. Finally, FIG. 2F provides a pair of representative gel photographs for the detection of *Yersinia* validating Applicants' primers YP1-F-m2 and YP1-R-m2. The top photograph of FIG. 2F shows these primers in gel run against a sample containing DNA for the three strains of *Y. pestis* listed in Table 1 (i.e., forming three bars, one each in columns 17-19), while the bottom photograph of FIG. 2F, for a gel run using a genus-inclusive primers detects not only the three different *Y. pestis* strains (the bars in columns 17-19 of the bottom photo) but also two strains of *Y. pseudotuberculosis* (at columns 14-15 of the bottom photo) and *Y. enterocolitica* (column 16 of the bottom photo).

Similar tests were run for each of Applicants' new primers identified in Table 2 to validate the specificity of these primers to their respective intended major food borne pathogens. In each case, the primers were able to detect the intended pathogen without triggering false positives for other non-virulent strains, serovars, and/or subspecies, as appropriate. In this manner, all of Applicants' primer pairs reported in Table 2 were validated as having sufficient sensitivity and specificity under the same amplification profile.

As shown in in the various photographs of FIG. 2A through 2F, the various species-specific primers identified in Table 2 were validated as having a very specific detection profile capable of discriminating each of the target species. In contrast, the genus-inclusive primers tested in parallel distinctively identified other members of the genus simultaneously with the target, serving as a control for the specificity of the new species-specific primers. Therefore, this experiment led Applicants to conclude that the new primers were very specific under the experimental conditions employed.

EXAMPLE 2

Conventional PCR is time consuming and labor intensive, and therefore not practical for use in the detection of pathogens in a high throughput platform. After conventional PCR methods were employed as described above to visualize the PCR products and determine the ability of each primer in Table 2 to identify their respective targets with specificity, Applicants performed the following experiments to determine the suitability of the primers for the detection of foodborne bacterial pathogens by real-time PCR. Again, these experiments were performed against DNA from the various 23 foodborne pathogens and related bacterial species listed in Table 1 as appropriate for the primers being tested.

PCR conditions were setup so that a species-specific primer was used to detect DNA from target and other bacteria arrayed on 96-well plates. On the array, one well was designated for DNA from one bacterial species or strain. While DNA was added to the designated wells, a primer solution was aliquoted to all the wells on the array. A positive curve was expected to be generated only from the wells containing primers and the target DNA in the same well. In a parallel array, to serve as a control for comparison, the same genus-inclusive primers as used in example 1 above were also aliquoted to all the wells containing DNA from the target species as well as other bacteria, including members of the genus. Positive curves were anticipated only from wells designated to the members of the same genus.

Real time PCR assay was performed using Brilliant III Ultra-Fast SYBR Green QPCR Master Mix (obtained from Agilent Technologies) for final validation & verification. A specific amplification was obtained with all the primers used to amplify the respective organisms. A reaction volume of 20 μl containing 500 nM of forward and reverse primers, 10 μl of 2× Brilliant III Ultra-Fast SYBER Green master mix, 0.3 μl ROX reference dye, 1 μl of DNA template, nuclease free $H_2O$ added to the final volume was used for the real-time PCR. The initial average amount of DNA used per well was 2 ng/μl. Cycling conditions were consisted of one cycle of segment 1, 2 minute at 95° C.; followed by 27 cycles of segment 2, 10 seconds at 95° C., 30 seconds at 60° C.; completed by one melting curve cycle of 1 minute at 95° C., 30 seconds at 65° C., and 30 seconds at 95° C.

Figure 3A:
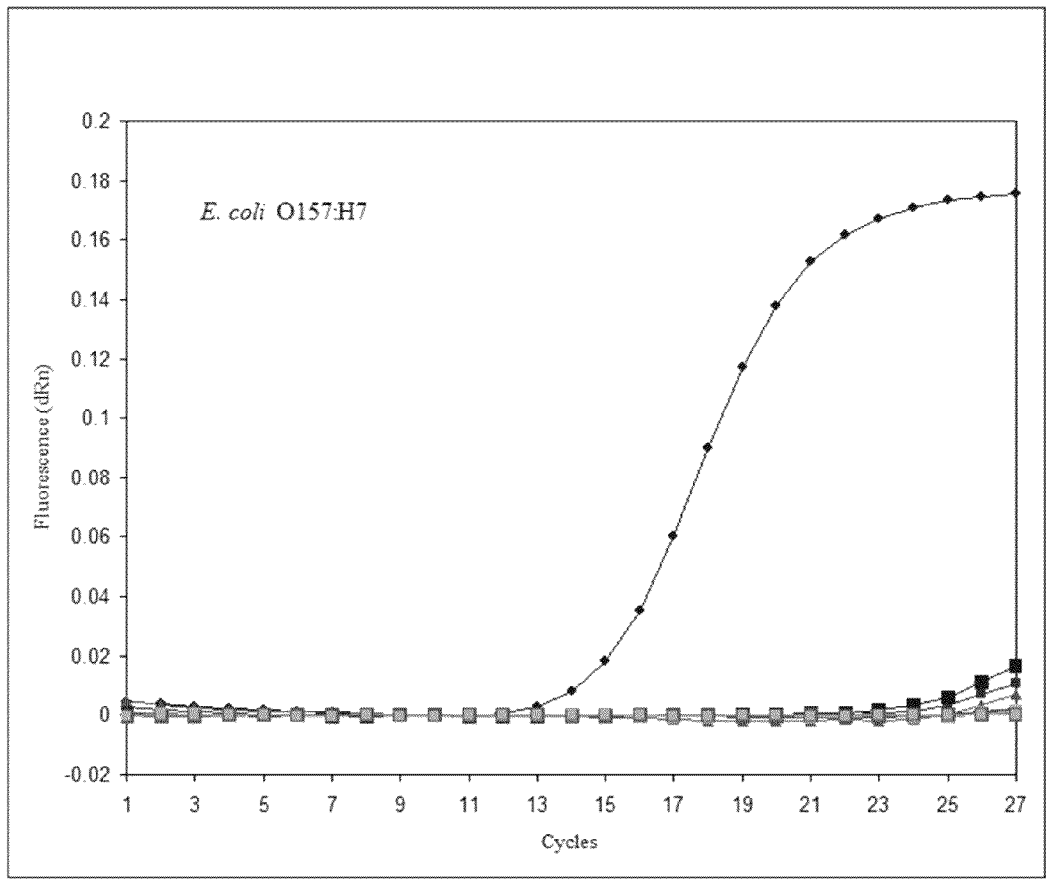
FIG. 3A through FIG. 3R depict real-time PCR amplification plots produced testing the selectivity of various primers according to embodiments of the present invention against genus-inclusive primers for various different target organisms.
Figure 3B:
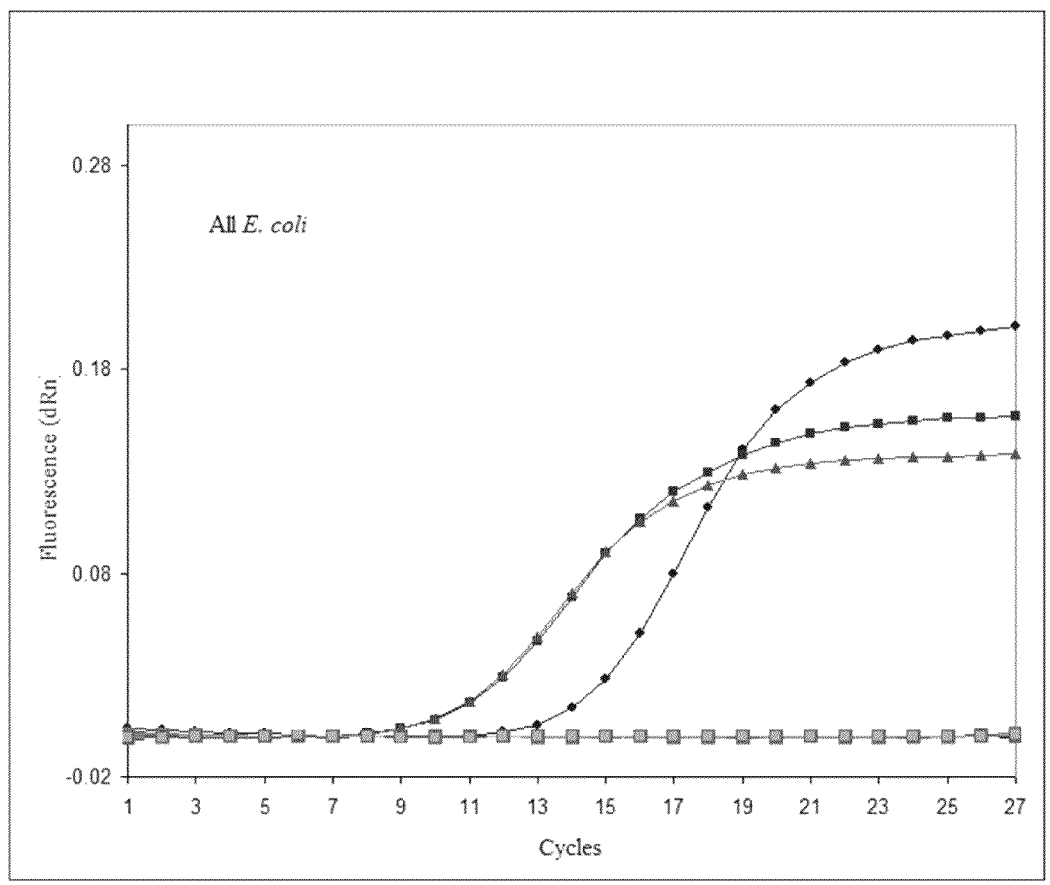
Figure 3C:
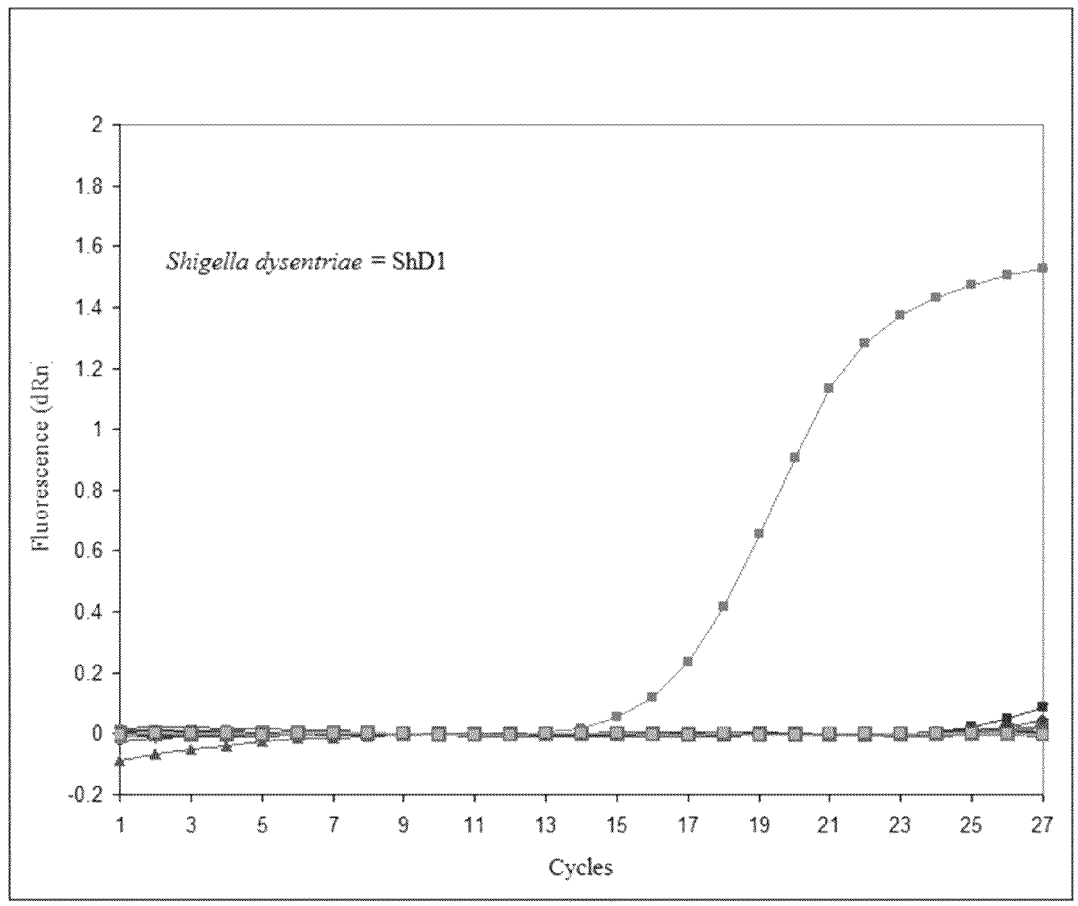
Figure 3D:
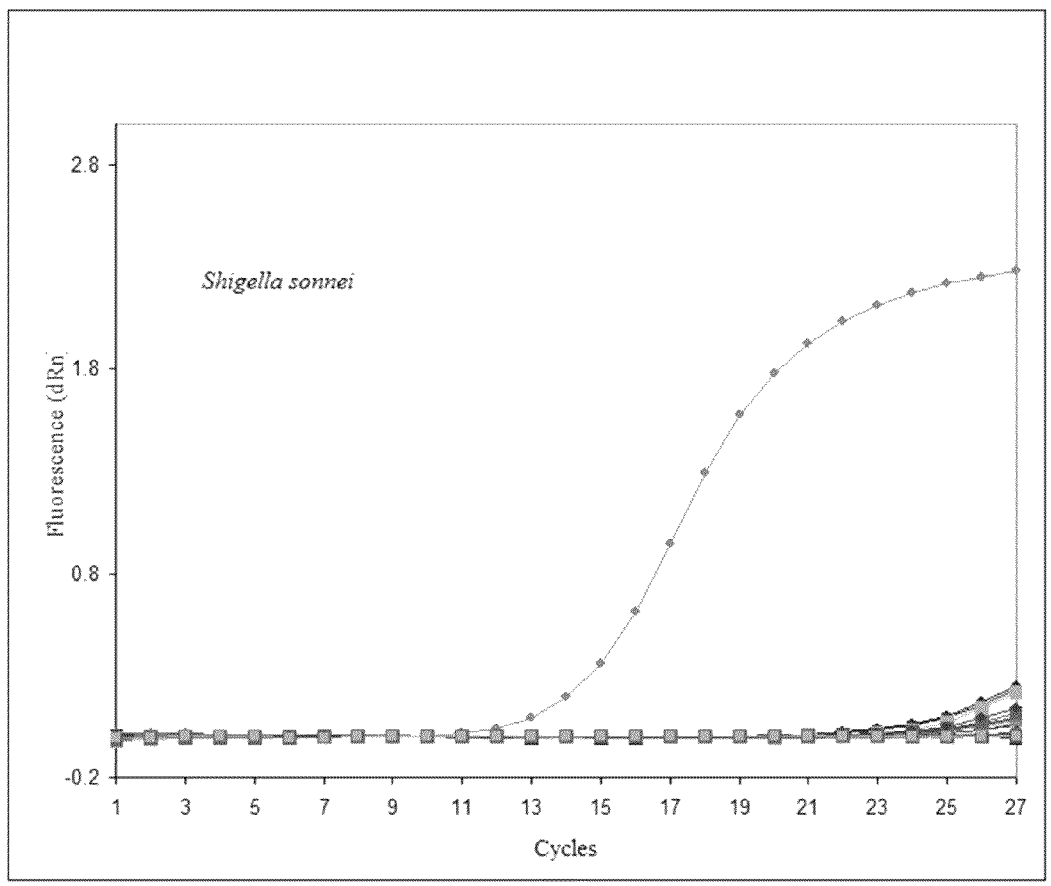
Figure 3E:
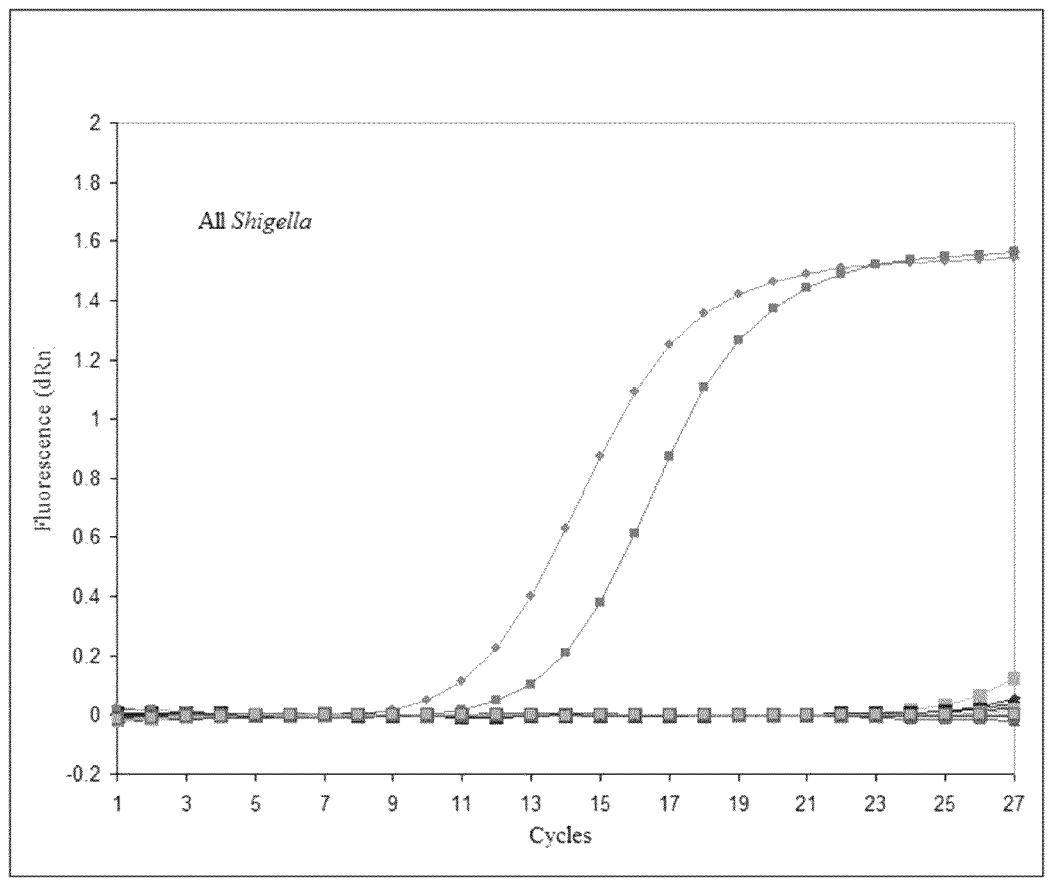
Figure 3F:
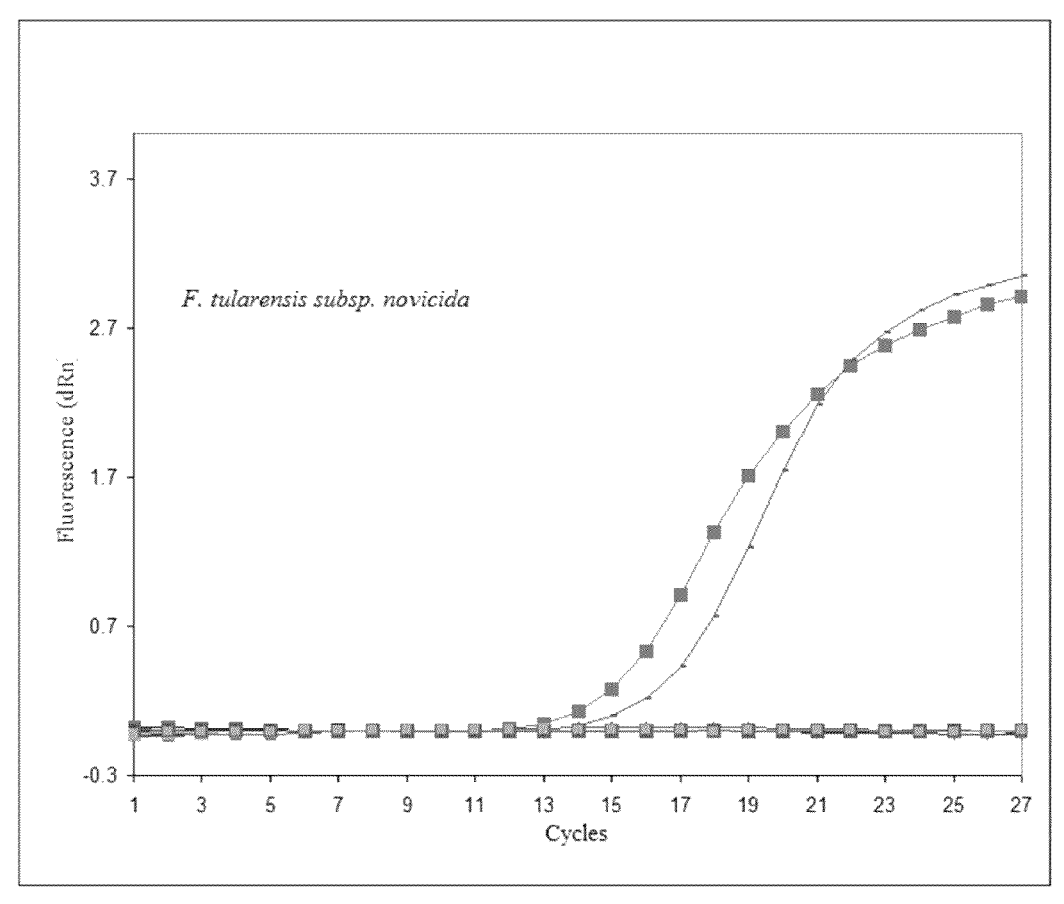
Figure 3G:
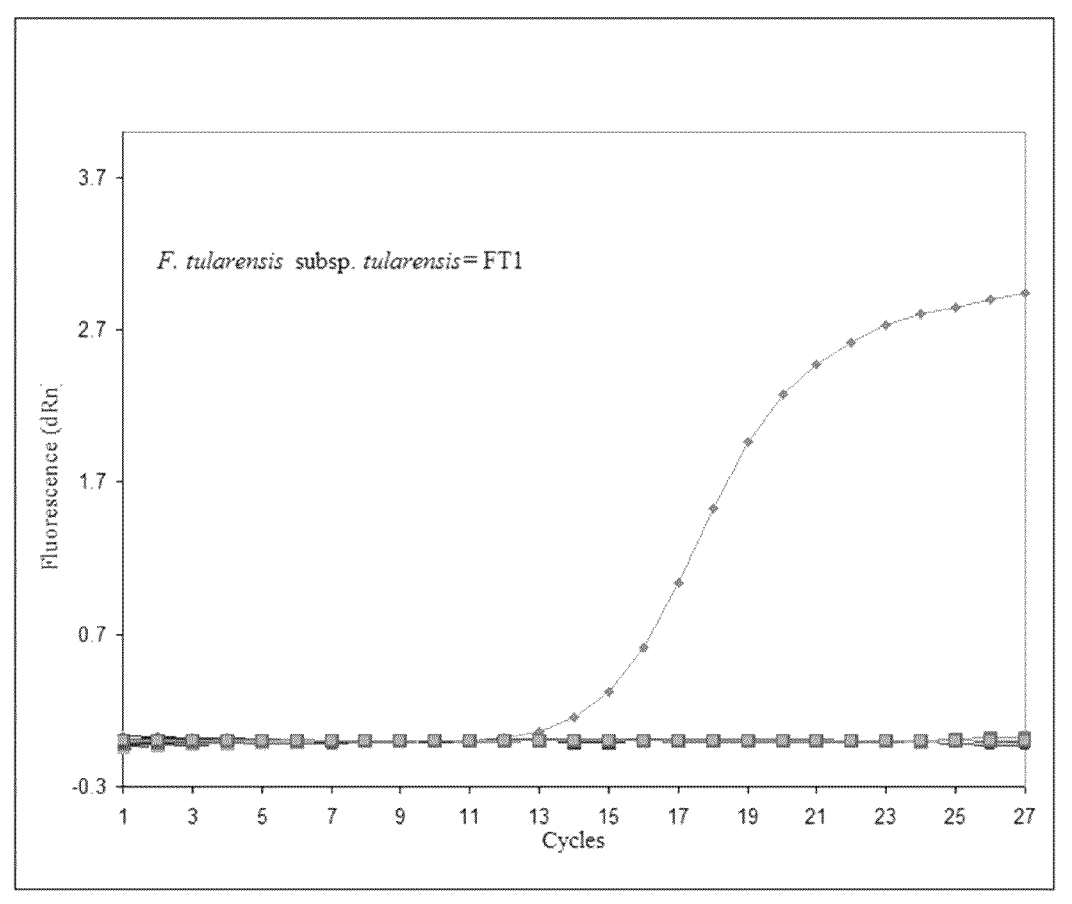
Figure 3H:
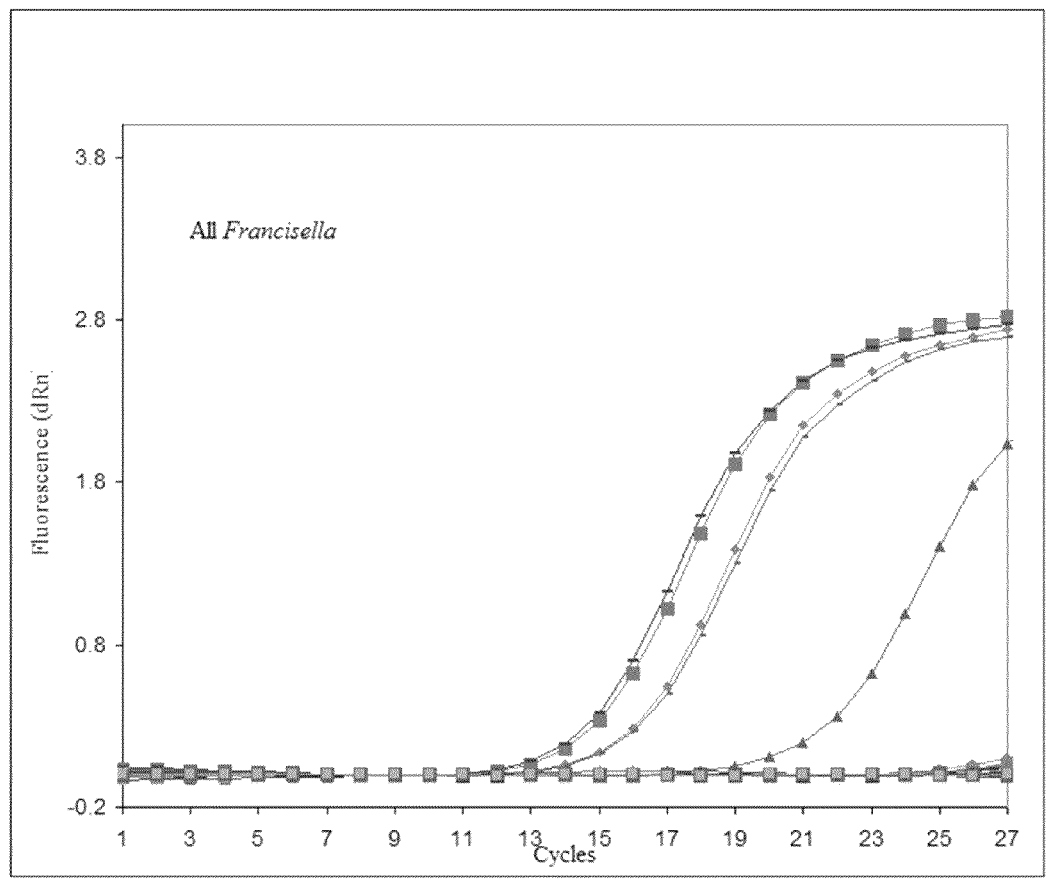
Figure 3I:
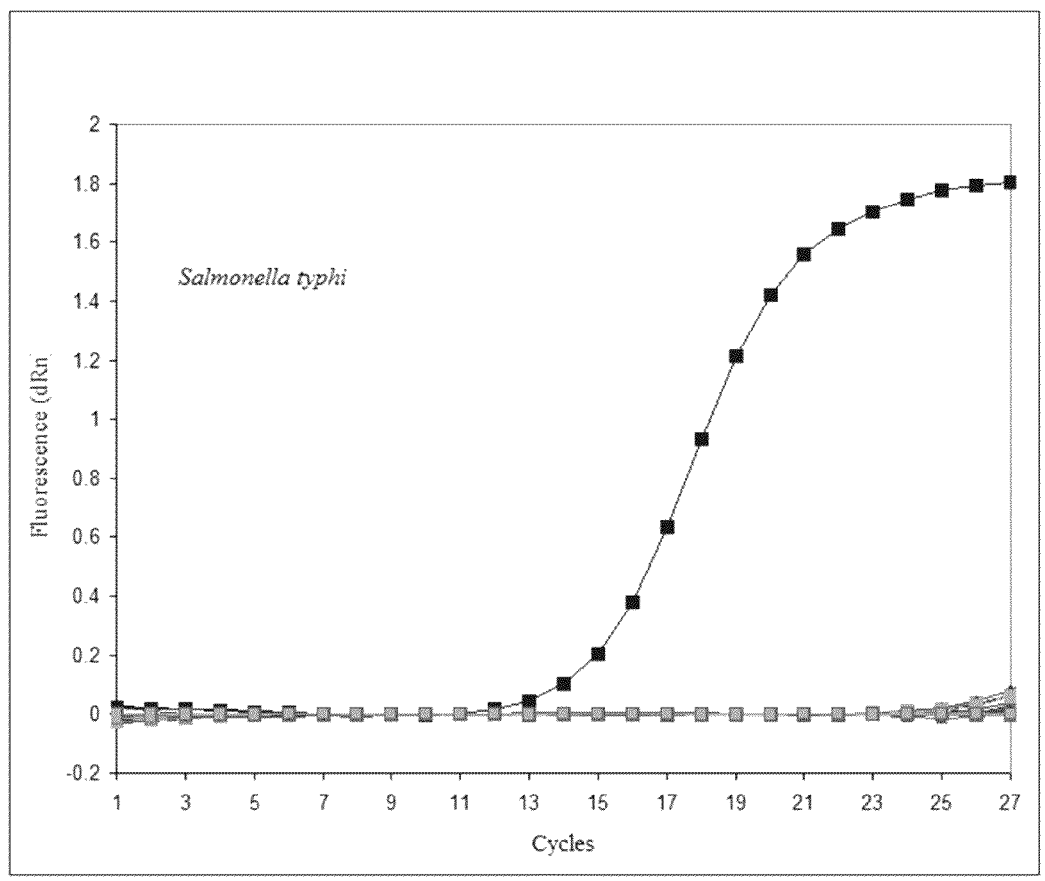
Figure 3J:
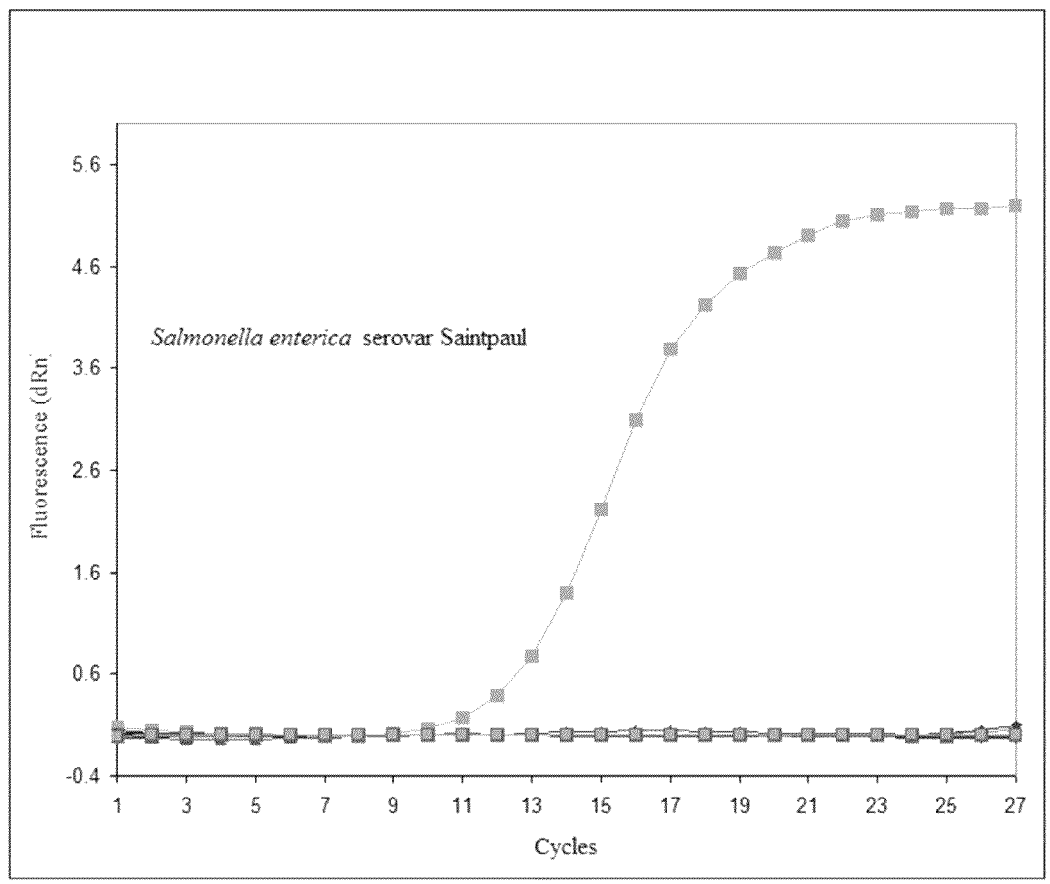
Figure 3K:
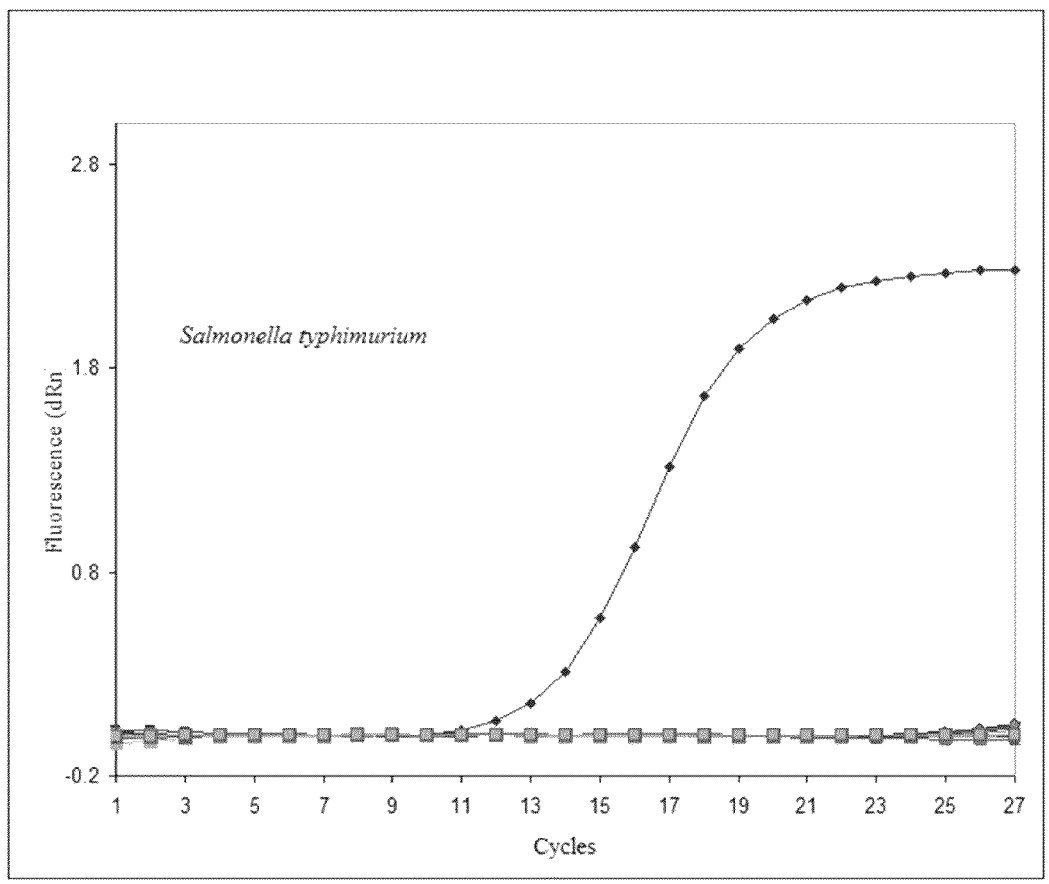
Figure 3L:
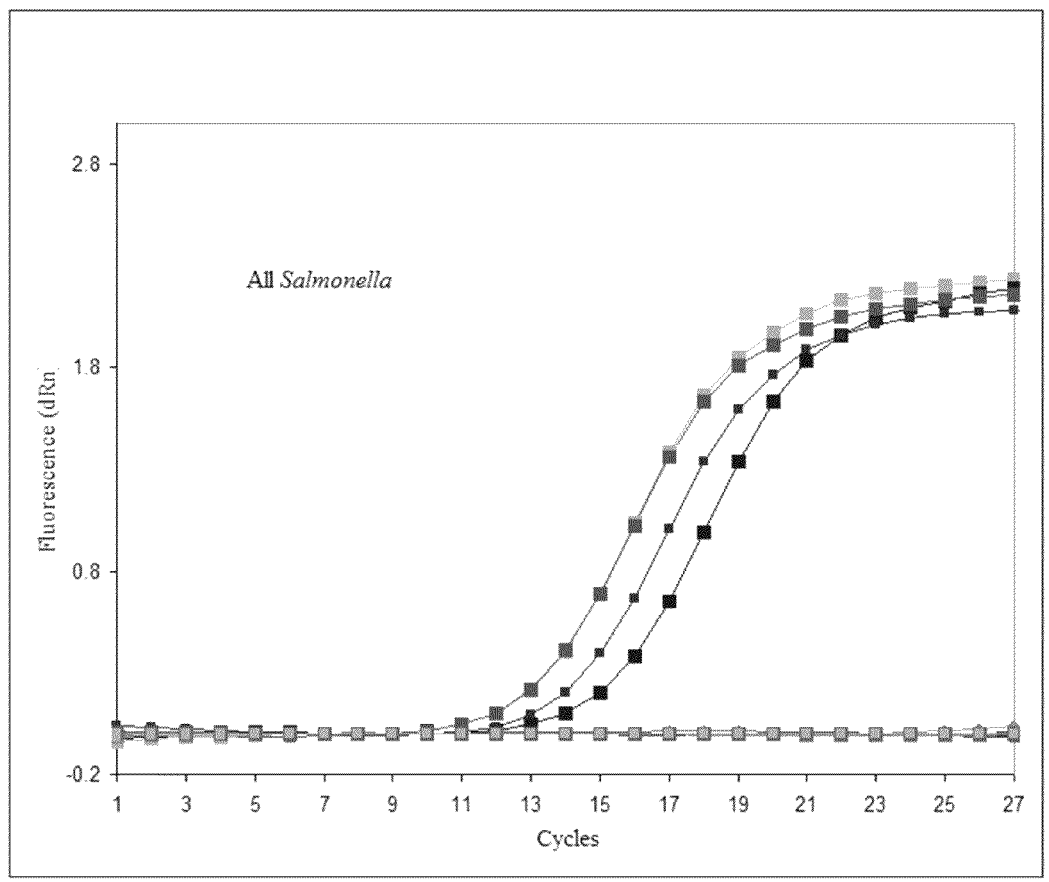
Figure 3M:
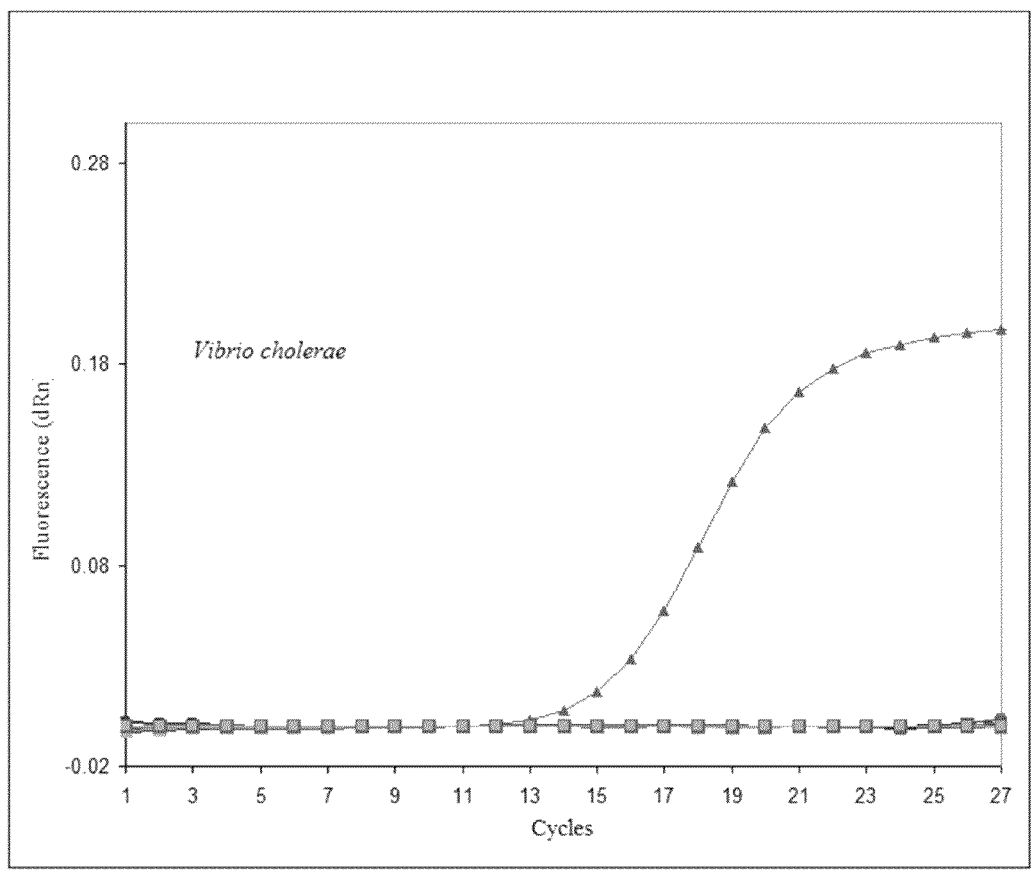
Figure 3N:
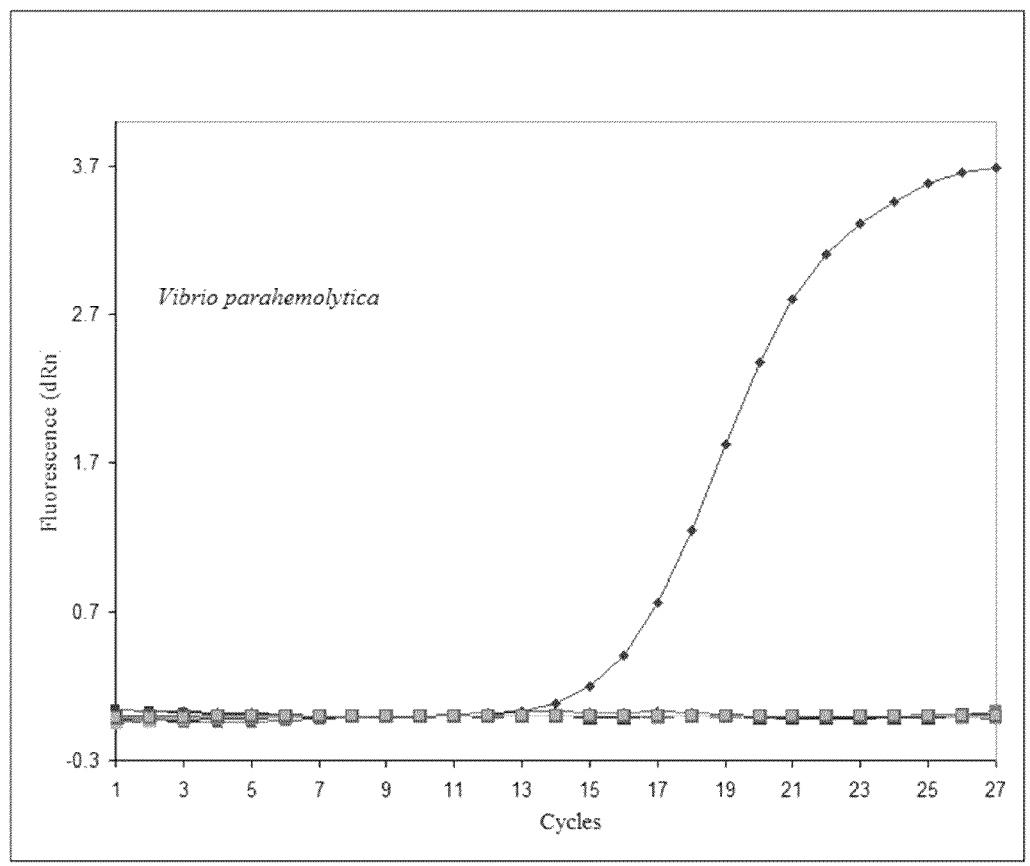
Figure 30:
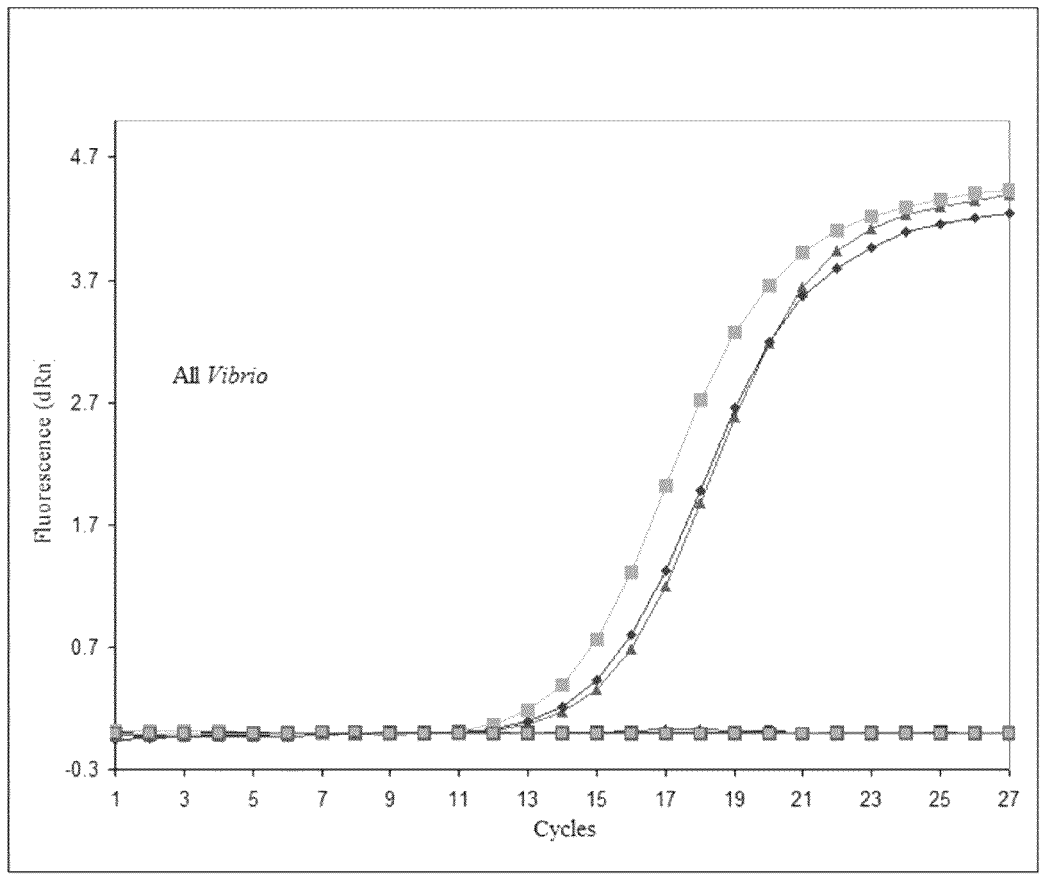
Figure 3P:
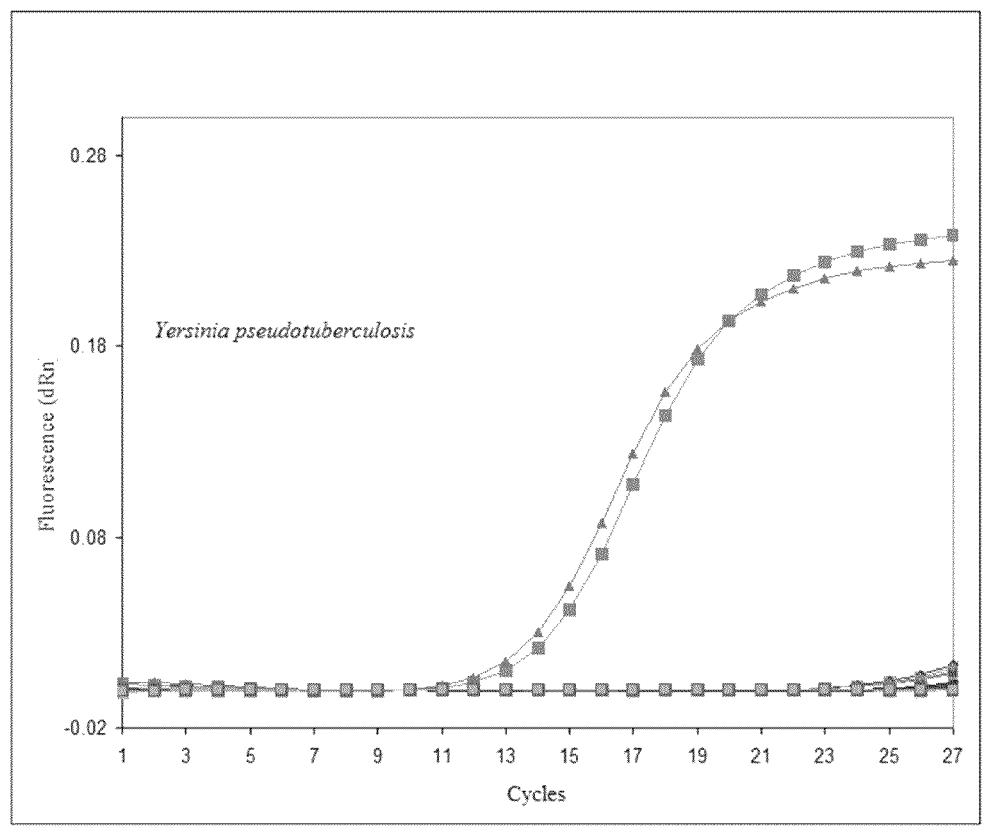
Figure 3Q:
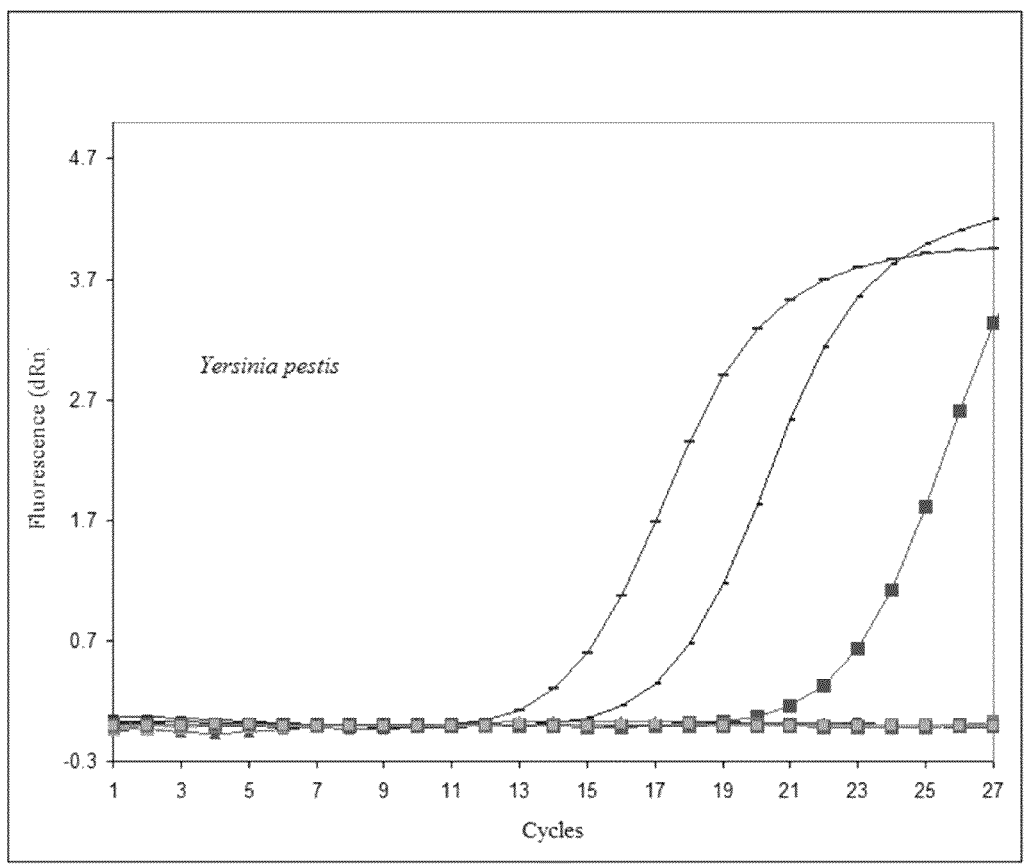
Figure 3R:
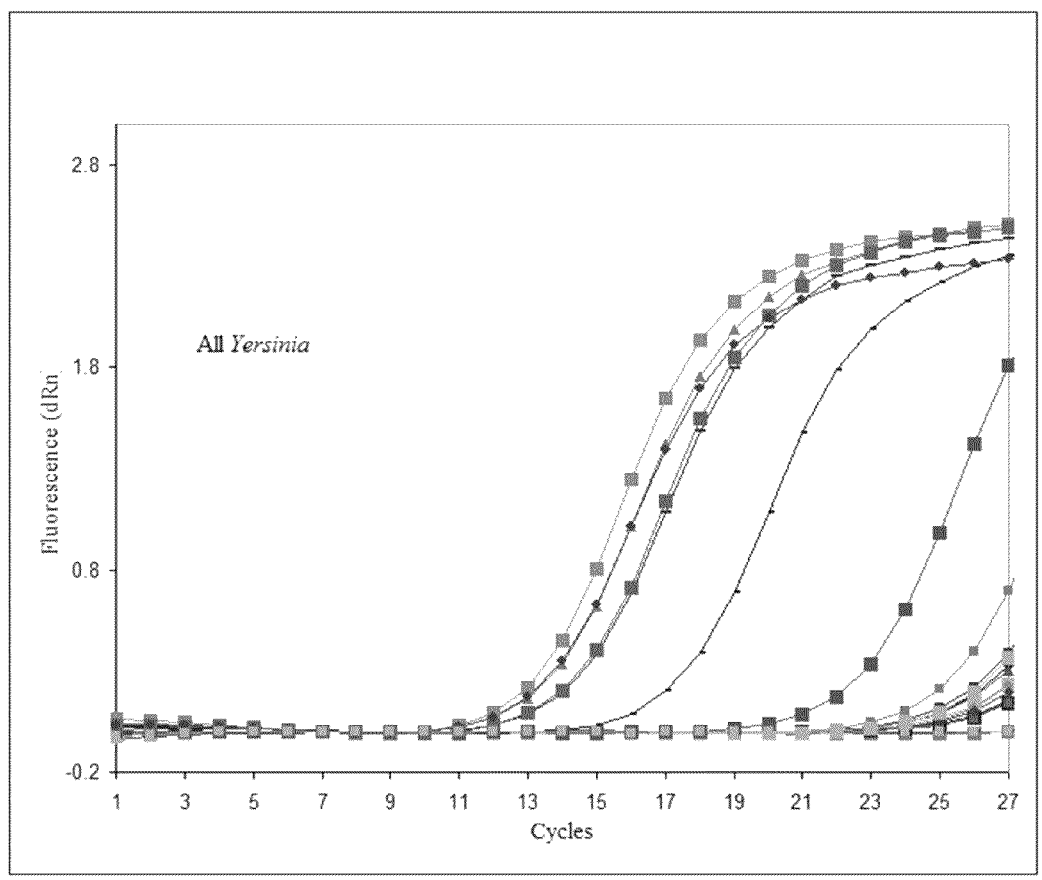

As exemplified by the real-time PCR plots of FIG. 3A through FIG. 3R, single curves were generated with all of the primers tested. The highest number of cycles for all the plots is 27. Since the PCR was not multiplexed for this experiment, the multiple curves shown in these figures were generated by merging data from the corresponding single curves originating from parallel simultaneous detection assays. In particular, FIG. 3A shows an amplification plot reporting exemplary results of three parallel real-time PCR runs for the detection of DNA from three distinct *E. coli* strains, namely strains O157:H7, HB101, and ATCC 1175 using Applicants' primer pair EC2-SLR-R-M and EC2-SLR-F-M. As can be seen in FIG. 3A, a single amplification curve (in light blue diamonds) is visible, representing the detection of strain O157:H7, while the curves for strains HB101 (red squares) and ATCC 1175 (green triangles) are essentially flat. FIG. 3B shows a similar amplification plot, but this time reporting exemplary results of three parallel real-time PCR runs for the detection of DNA from the same *E. coli* strains but using the genus-inclusive primer for *E. coli*. In FIG. 3B, it is clear that all three strains are amplified, thus showing the both the specificity of primers EC2-SLR-R-M and EC2-SLR-F-M for *E. coli* O157:H7 and its suitability for use in real-time PCR. A similar experiment was performed for each of Applicants' primers of Table 2 with similar results.

FIG. 3C through FIG. 3R each are amplification plots which, similar in fashion to FIG. 3A and FIG. 3B, in pairs show exemplary data of comparisons between certain other ones of Applicants' primers of Table 2 versus genus-inclusive primers. FIG. 3C through FIG. 3E shows results for real-time PCR against a mixture of the *Shigella* organisms in Table 1 using Applicants' *S. dysenteriae* targeted primers ShD1-F/R (FIG. 3C), Applicants' *S. sonnei* targeted primers rhysA-y-sonnei-FIR (FIG. 3D), and a genus-inclusive primer for *Shigella* (FIG. 3E). Again, both of Applicant's primer pairs produced a single, real-time amplification curve even though more than one *Shigella* species was present.

FIG. 3F through FIG. 3H shows amplification plots for real-time PCR batches performed against one strain of *Francisella tularensis* ssp. tularensis, and two strains of *F. tularensis* ssp. novicida. FIG. 3F, generated using Applicants' primers FN2-mR/F, produced two amplification curves, indicating that those primers detected both strains of novicida while FIG. 3G, generated using Applicants' primers FT1-F/R, produced only a single curve, indicating detection of only the tularensis subspecies. The plot of FIG. 3H was generated using the genus-inclusive primer for *Francisella*, and thus confirmed the presence of DNA for all three subspecies/strains in the common test sample.

FIG. 3I through FIG. 3L shows single amplification plots for real-time PCR batches performed against three serovars of *S. enterica* ssp. enterica, namely *serovars Typhi* (herein abbreviated as "*S. Typhi*"), Saintpaul (herein abbreviated as "S. Saintpaul"), and Typhimurium. The plot of FIG. 3I was generated using Applicants' paired primers ST1-F-m-2 and ST1-R-m2 and produced only a single amplification curve, corresponding to the single S. Typhi serovar in the test sample. FIG. 3J, generated using Applicants' primers SS2-F-n and SS2-R-n, likewise produced only a single curve for the single S. Saintpaul serovar. Similarly, Applicants' primers ST1-F-M and ST1-R-M produced only a single curve for the S. Typhimurium serovar, as shown in FIG. 3K. Presence of DNA from all three organisms in the test sample was confirmed using a *S. enterica* inclusive primer, as shown by the plot of FIG. 3L.

FIG. 3M through FIG. 3O show real-time PCR amplification plots using test samples containing DNA from the three *Vibrio* species identified in Table 1. The plot of FIG. 3M shows the specific detection of *V. cholerae* in this test sample using Applicants' primers VC1-pho-R/F, while FIG. 3N shows the detection of *V. parahaemolyticus* in this same test sample using primers VpH1-F/R. FIG. 3O again confirms, using a genus-inclusive primer, that the test sample contained two different *Vibrio* organisms.

Finally, FIG. 3P through FIG. 3R show real-time PCR amplification plots using test samples containing DNA from the seven *Yersinia* species and strains identified in Table 1. In FIG. 3P, the amplification plot for primers YPs1-F-M and YPs1-R two curves corresponding to the two *Y. pseudotuberculosis* strains in the test sample. Primers YP1-F-m2 and YP1-R-m2 were used for the real-time PCR batches reflected in FIG. 3Q, and those primers effectively detected the three *Y. pestis* strains in the test sample. Finally, FIG. 3R confirms with a genus-inclusive primer that the test sample contained seven different *Yersinia* organisms.

Similar experimental results were obtained for each of Applicants' primers listed in Table 2. In this manner, the various species-specific primers identified in Table 2 were validated as having high specificity when used in real-time PCR.

EXAMPLE 3

The following experiment was conducted to test the sensitivity of each of the primers identified in Table 2. Sensitivity in a real-time PCR assay was determined by five-fold serial dilution of several target DNA samples in nuclease-free double distilled $H_2O$ from each of the bacterial species. Initial DNA concentrations were 2.5 ng/μl for *E. coli* O157:H7 strain EDL933, 2 ng/μl for *Francisella tularensis* ssp. tularensis, 2.6 ng/μl for *Shigella dysenteriae*, 3.7 ng/μl for *S. Typhi*, 3 ng/μl *Vibrio cholerae* and 3.8 ng/μl for *Yersinia pestis*. One microliter of each of the DNA dilutions were used in a 20 μl total reaction volume and real-time PCR was run for 27 amplification cycles (under similar conditions to the example described above). At the end of the run, 4 μl aliquots from each of the wells were resolved on a 2% agarose gel and visualized by GelRed staining (Biotium®, Hayward, Calif.).

FIG. 4A through FIG. 4F are amplification plots for real-time PCR performed on the various serially-diluted test samples. As shown in these figures, the sensitivity of the assay was variable between the organisms used. FIG. 4A constitutes a plot for *E. coli* using the primer pair EC2-SLT-R-m and EC2-SLT-F-m, and the upward curves from left to right represent the amplification of increasingly diluted samples of 2.5 ng/μl, 0.5 ng/μl, 0.1 ng/μl, 20 pg/μl, 4 pg/μl, and 800 fg/μl of target *E. coli* DNA FIG. 4B constitutes a plot for *F. tularensis* ssp. tularensis using the primer pair FT2-mR/F, and the upward curves from left to right represent the amplification of increasingly diluted samples of 2 ng/μl, 400 pg/μl, 80 pg/μl, 16 pg/μl, 3.2 pg/μl, and 640 fg/μl of DNA. FIG. 4C constitutes a plot for *Y. pestis* using the primer pair YP1-F-m2 and YP1-R-m2, and the upward curves from left to right represent the amplification of increasingly diluted samples of 3.8 ng/μl, 760 pg/μl, 152 pg/μl, 30 pg/μl, 6 pg/μl, 1.2 pg/μl and 234 fg/μl. FIG. 4D constitutes a plot for *V. cholerae* using the primer pair VC1-pho-F/R, and the upward curves from left to right represent the amplification of increasingly diluted samples of 3 ng/μl, 600 pg/μl, 120 pg/μl, 24 pg/μl, 4.8 pg/μl, and 0.96 pg/μl.

Figure 4A:
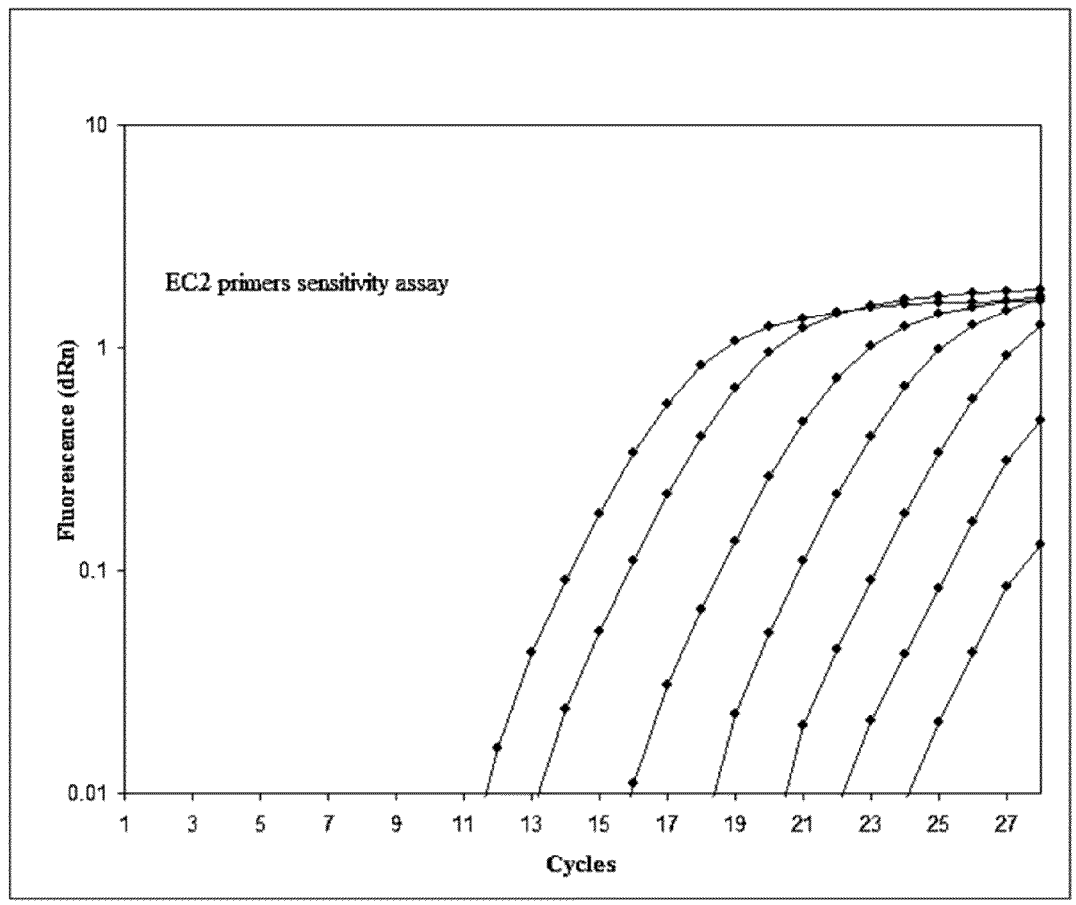
FIG. 4A through FIG. 4F are color drawings of amplification plots for real-time PCR performed on the various serially-diluted test samples to test the sensitivity of various primers according to embodiments of the present invention.
Figure 4B:
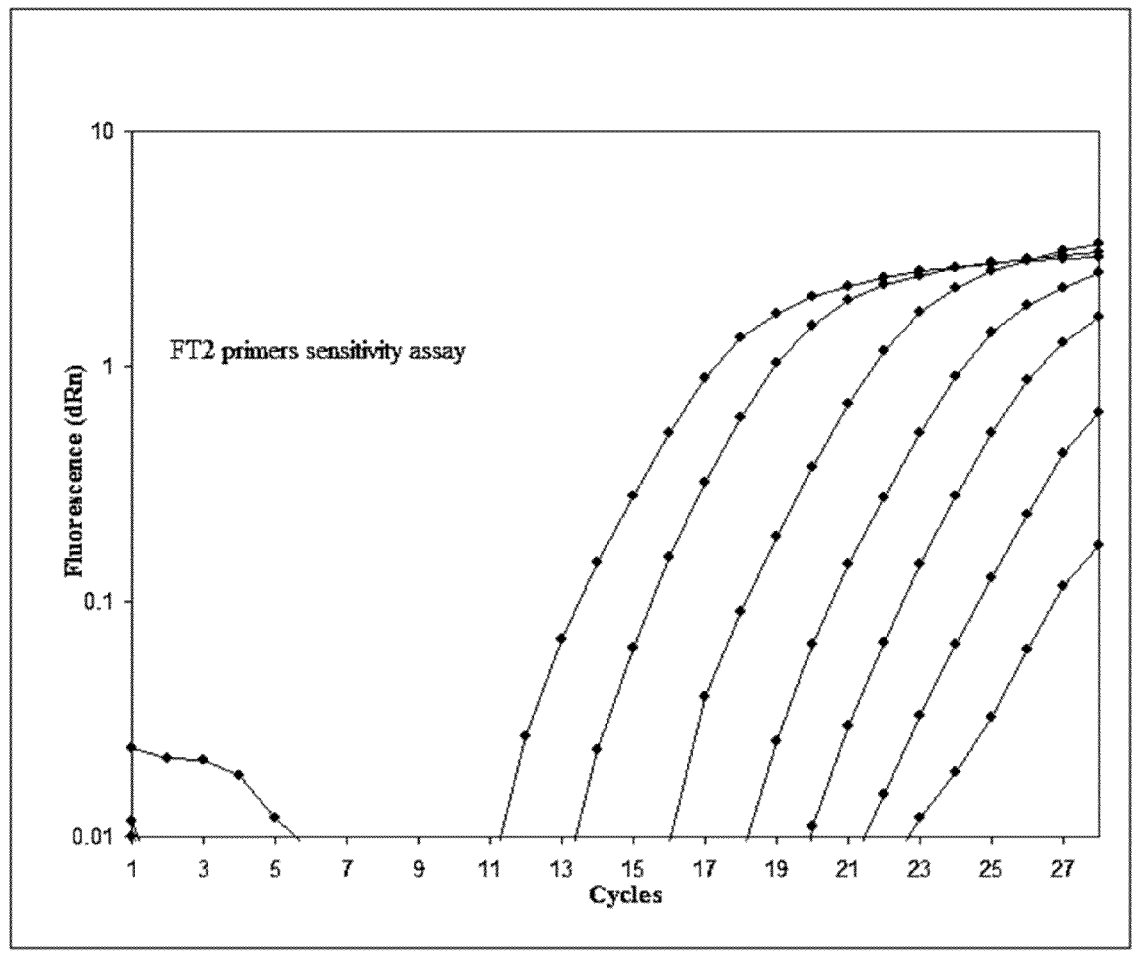
Figure 4C:
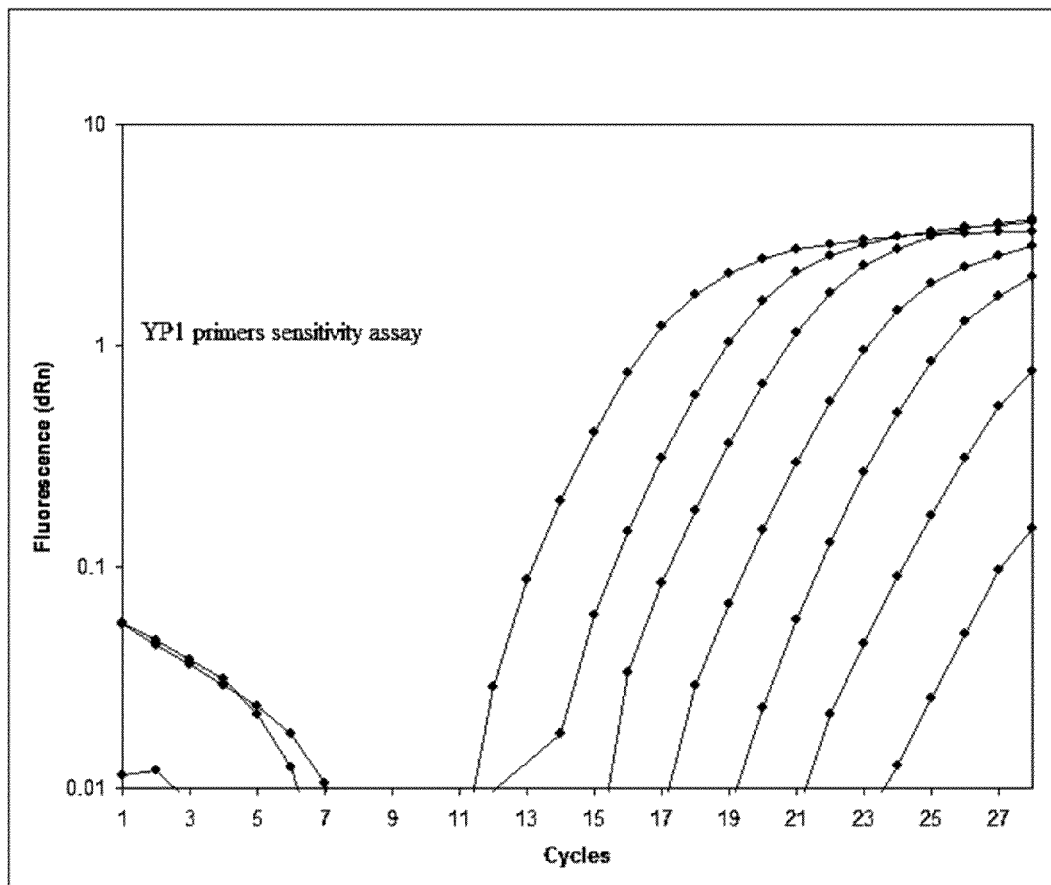
Figure 4D:
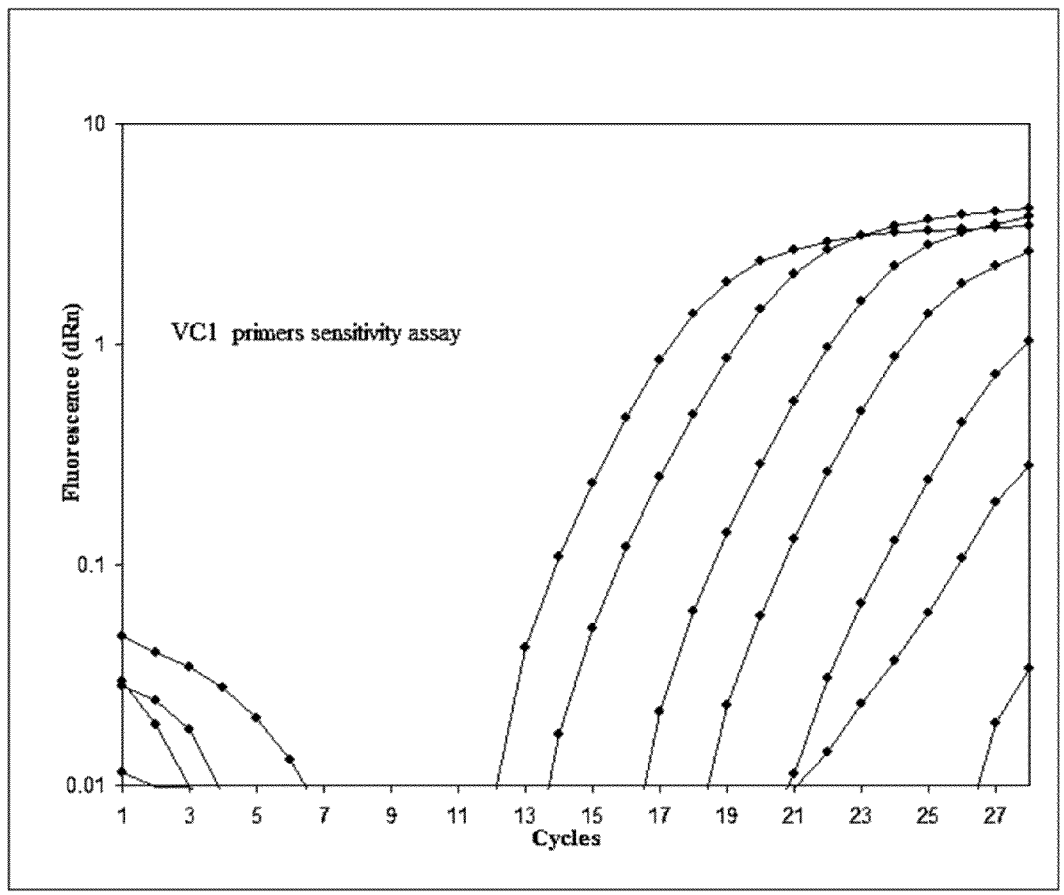
Figure 4E:
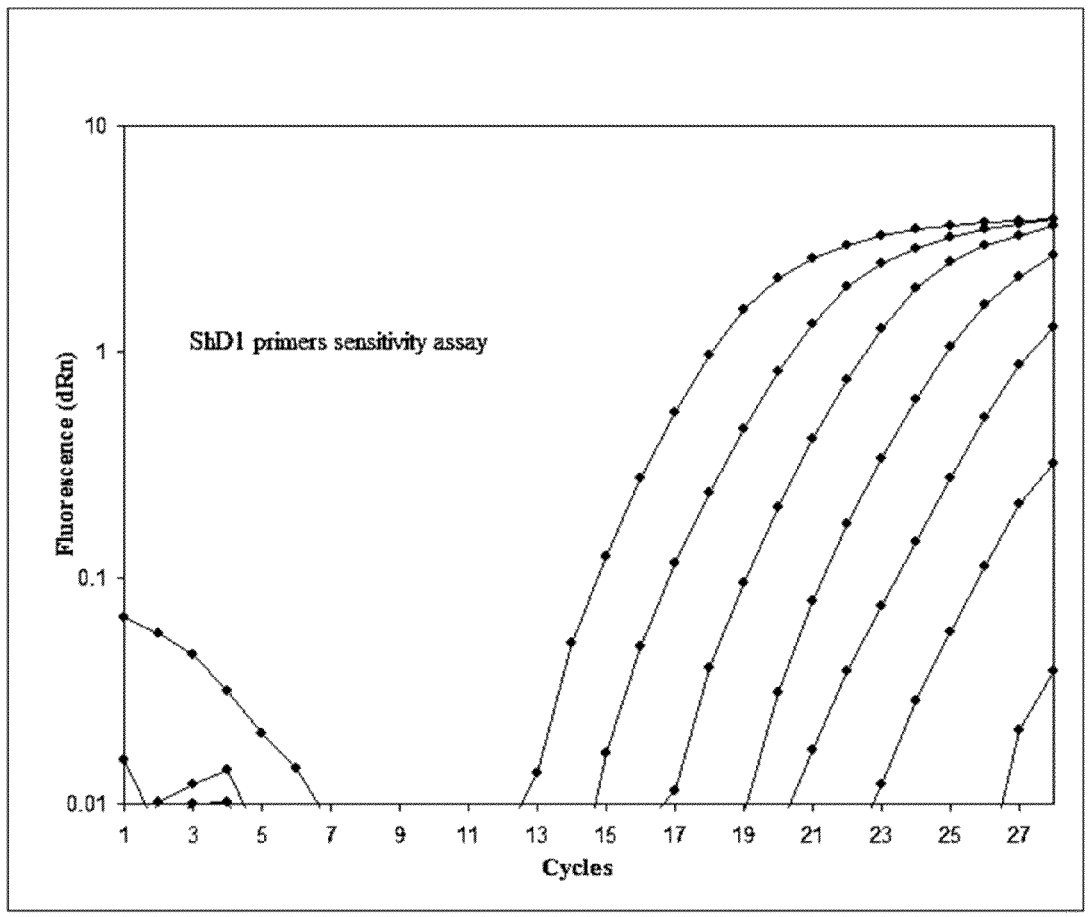
Figure 4F:
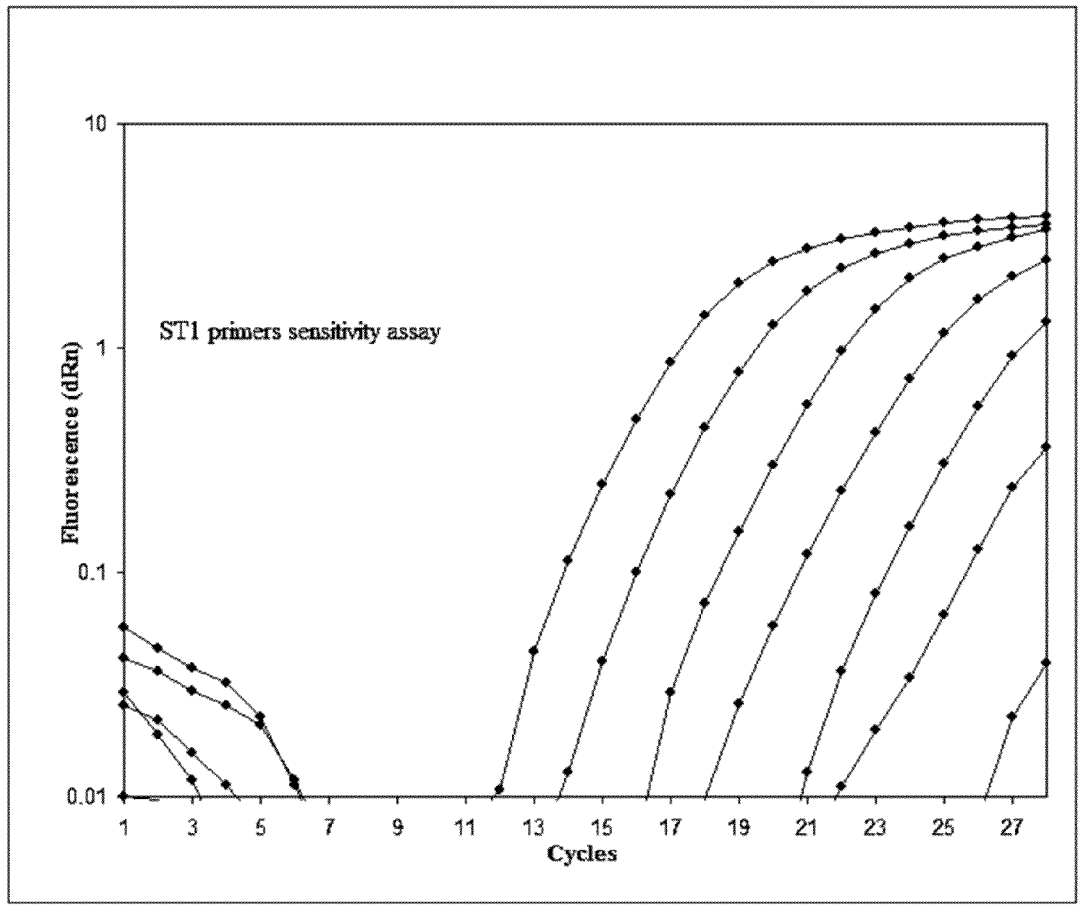
Figure 5A:
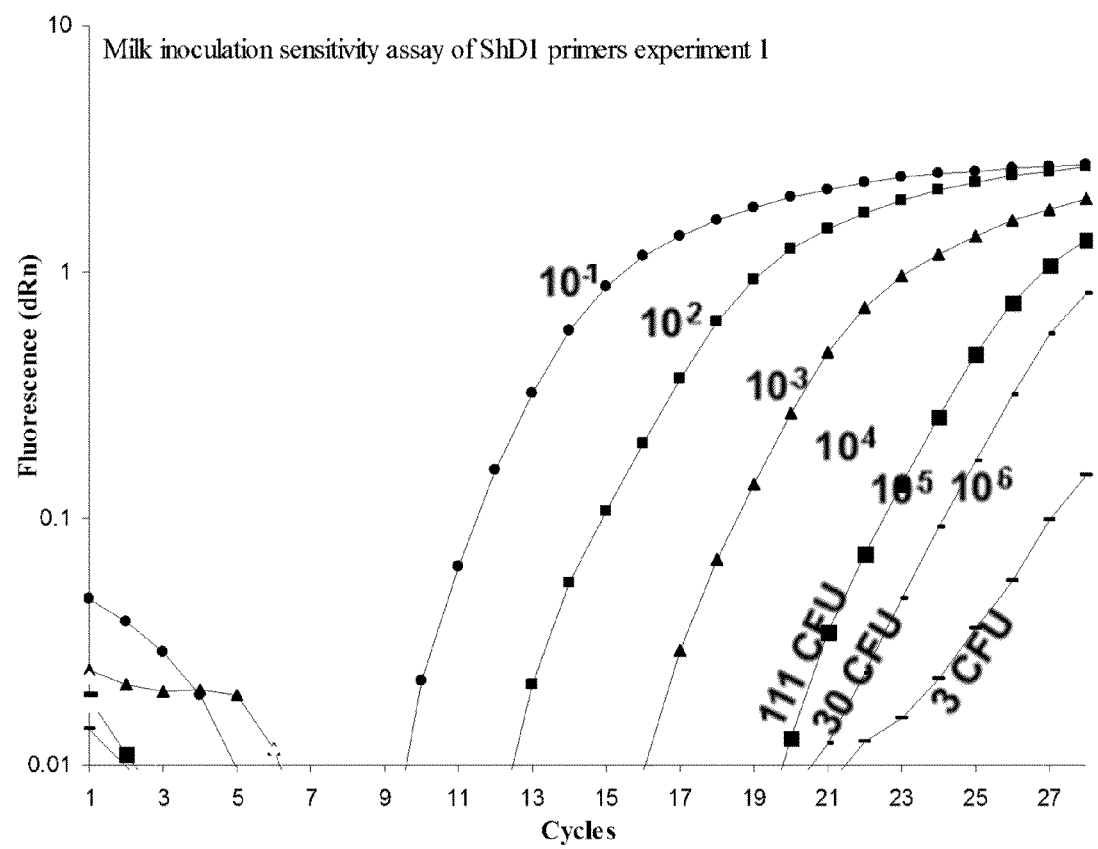
FIG. 5A through FIG. 5C depict amplification plots from three independent trials repeated for a food matrix sensitivity assay.
Figure 5B:
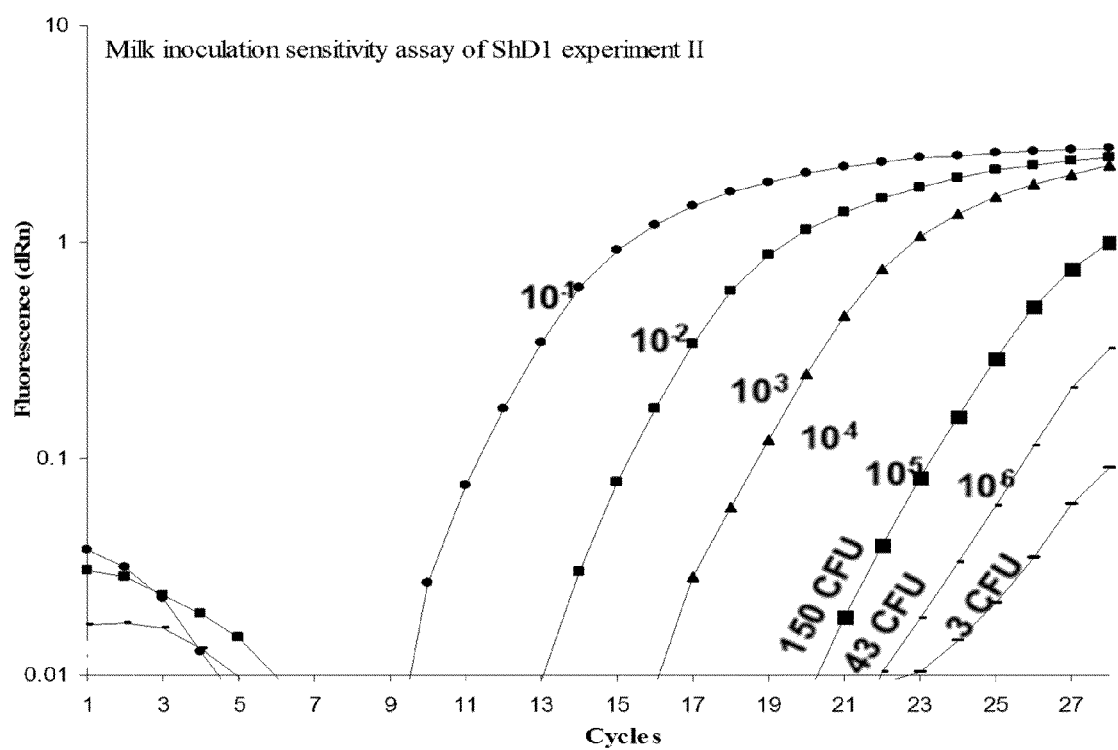
Figure 5C:
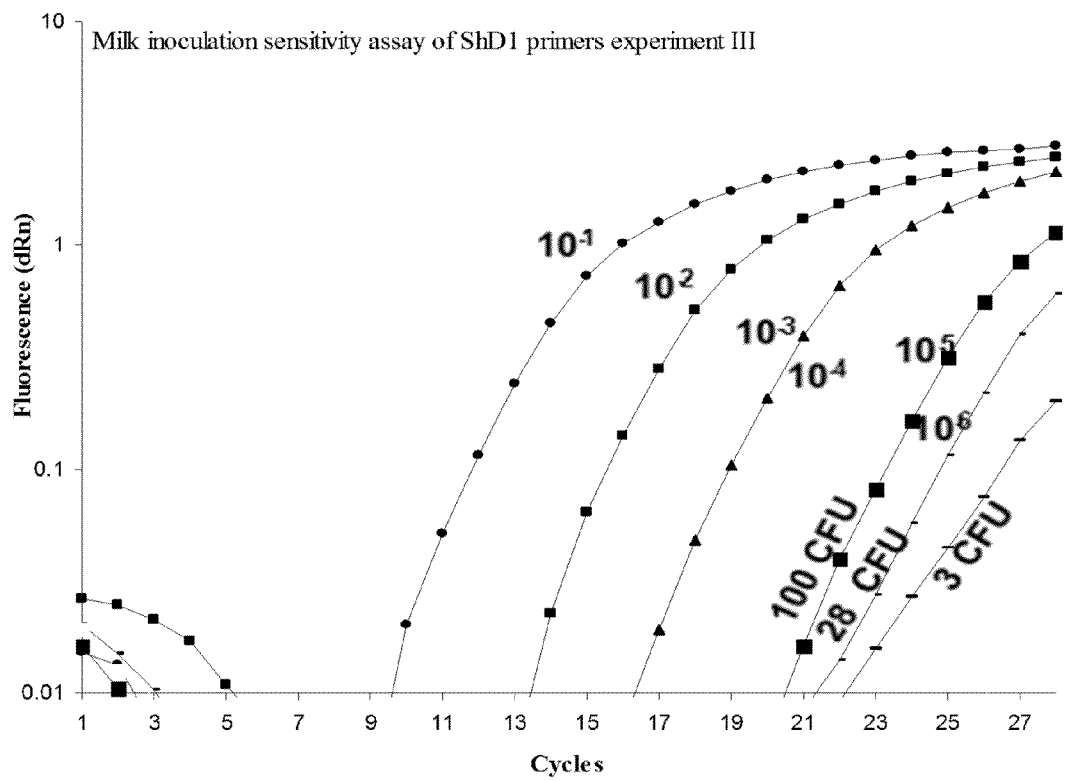

FIG. 4E constitutes a plot for *S. dysenteriae* using the primer pair ShD1-F/R, and the upward curves from left to right represent the amplification of increasingly diluted samples of 2.6 ng/μl, 520 pg/μl, 104 pg/μl, 20.8 pg/μl, 4.16 pg/μl, and 832 fg/μl. Finally, FIG. 4F constitutes a plot for *S. Typhi* using the primer pair ST1-F-m-2 and ST1-R-m2, and the upward curves from left to right represent the amplification of increasingly diluted samples of 3.7 ng/μl, 740 pg/μl, 148 pg/μl, 29.6 pg/μl, 5.92 pg/μl, and 1.18 pg/μl. Thus, starting at 3.8 μg/μl DNA concentration, a 230 fg/μl dilution was detectable for *Y. pestis* DNA while 640 fg/μl of diluted *F. tularensis* genomic DNA was reliably detected for both species both under threshold cycle of 27. The overall detection range varied between 234 fg/pμl (*Y. pestis*) and 1.18 pg/μl (for *S. Typhi*) of genomic DNA. The gel electrophoregrams obtained in this experiment also showed generation of bands of the correct size as well as visible limits of the serial dilution under these experiment conditions.

Therefore, under these conditions, Applicants found that these six primers were able to achieve a high sensitivity of detection combined with the high specificity as described above. Similar sensitivity assays of various other primers achieved results confirming them as having suitable sensitivities for use.

EXAMPLE 4

Food matrices provide a critical challenge in amplification-based pathogen detection approaches because, among other things, pre-analytical sample processing techniques must be streamlined to reduce the time needed to arrive at diagnosis and decision-making. In this experiment, Applicants performed a preliminary experiment to evaluate the real time detection of *S. dysenteriae* spiked in milk to evaluate whether real-time detection as described herein would be compatible with DNA isolated from bacteria in food matrix.

In the experiment, skim milk (450 μl) was inoculated with $7.5\times10^{8}$ CFU of *S. dysenteriae* (attenuated strain obtained from ATCC) culture suspension and diluted serially in a total of 500 μl suspension volumes up to $10^{-8}$. After the dilution, bacteria in each aliquot were immediately concentrated by centrifugation at 12000 RPM for 2 minutes, and whole genome DNA was extracted from all of the serially diluted tubes according to the procedure described by PrepMan Ultra Sample Preparation (Applied Biosystems, CA). Parallel cultures were also initiated from each of the dilutions to count colony forming units ("CFUs").

FIG. 5A through FIG. 5C depict amplification plots from three independent trials repeated for the procedure described above. As shown in these figures, with three independent experiments, we were able to detect DNA isolated from milk spiked with *Shigella* organisms with an approximate detection limit of 6-60 colony forming units per ml of milk, and this detection is obtainable within 1 hr of detection time.

EXAMPLE 5

A second experiment was performed to investigate the limit of detection ("LOD") for *S. enterica* in different food matrices for Applicants' real-time assays and primers. Cultures of *S. enterica* ser. Typhimurium and ser. Saintpaul were grown overnight in tryptic soy broth at 37° C., and then both cultures were separately 1:10 serially diluted to form eight sample solutions. Dilution was achieved by mixing 100 μl of the grown broth culture in 1 ml of new broth to form a first, "$10^{-1}$," sample solution, thereafter taking 100 μl from that first sample solution and adding it to a second vial containing 1 ml of new broth to form a second, "$10^{-2}$," sample vial, and so forth until an eighth, "$10^{-8}$," sample solution was obtained for each of the S. Typhimurium and S. Saintpaul cultures.

Different samples from three food matrices, beef hotdog, skim milk, and 1% fat milk, were then spiked with the sixteen sample solutions. Sixteen contaminated beef hotdog samples were each prepared by placing 1 g of minced hotdog meat in 2.7 ml of PBS and then adding into each mixture a 300 μl aliquot from a different one of the sample vials (i.e., forming eight different hot dog samples having different concentrations of S. Typhimurium and eight having different concentrations of S. Saintpaul). Sixteen contaminated milk samples were prepared for each of the two different milk types by adding a 100 μl aliquot from a different one of the sample vials into 1 ml of skim milk or 1% milk. As in the experiment of Example 4, parallel cultures were also initiated in this experiment to count colony forming units.

After the contaminated food matrix samples were prepared, the bacteria in each contaminated sample were extracted as described above in Example 4. Real-time PCR was then performed on each sample using Applicants' primer pairs STM1, STM2, and SS2. The LOD for S. Typhimurium was >700 CFU/ml at a dilution of $10^{-4}$ for both S. Typhimurium primers, and a similar result was obtained for S. Saintpaul.

The analysis was repeated again for each of the contaminated samples, but this time using a QIAamp DNA mini kit extraction per manufacturer's instructions (available from Qiagen, Inc. of Germantown, Md.). This time, Applicants found the lowest LOD for S. Typhimurium in beef hotdog using primers STM1, where concentrations of 9 CFU/ml were detectable at cycle thresholds of approximately 29.1. The LOD for skim milk and 1% milk contaminated with S. Typhimurium was 78 CFU/ml with primers STM1 at cycle thresholds of approximately 28. The LOD for all three food matrices for S. Typhimurium using primers STM2-F/R-m was 86 CFU/ml, with cycle thresholds ranging from about 26.0-32.5. Thus, Applicants have confirmed that the primers and methods of embodiments of the present invention may be used to detect relatively low contaminations present in complex food matrices, but that sensitivity can be maximized by adopting better pathogen extraction and concentration methods.

EXAMPLE 6

To test the potential suitability of the primers of various embodiments of the present invention for use in a one-tube multiplex PCR assay, Applicants ran experiments to determine if the dissociation curves from the real-time PCR could be used to identify different multiple pathogens included in a multiplex assay. For this experiment, an test sample was produced containing roughly equal concentrations of DNA from *E. Coli* O157:H7, *F. tularensis, S. Typhi, S. dysenteriae, Y. pseudotuberculosis*, and *V. cholerae*. Although good results were obtained with conventional PCR assay of six selective agents, obtaining distinct real-time PCR dissociation curves for multiple organisms becomes more difficult as the number of simultaneously-assayed organisms increases.

FIG. 6A is a black and white photograph of a gel comparing multiplex PCR for conventional single-target PCR using primers according to embodiments of the invention. The columns from left to right in the gel of FIG. 6A are labeled EC1 (containing primers EC1-R/Fm), FT1 (containing primers FT1-R/F), ST (containing primers ST1), ShD (containing primers ShD1), YP (containing primers YP2), VC (containing primers VC1), and Multiplex (containing all six primer pairs).

Single bands are clearly visible in the first six columns of the gel, while individual bands in the seventh "Multiplex" column are not as easily distinguished.

Figure 6A:
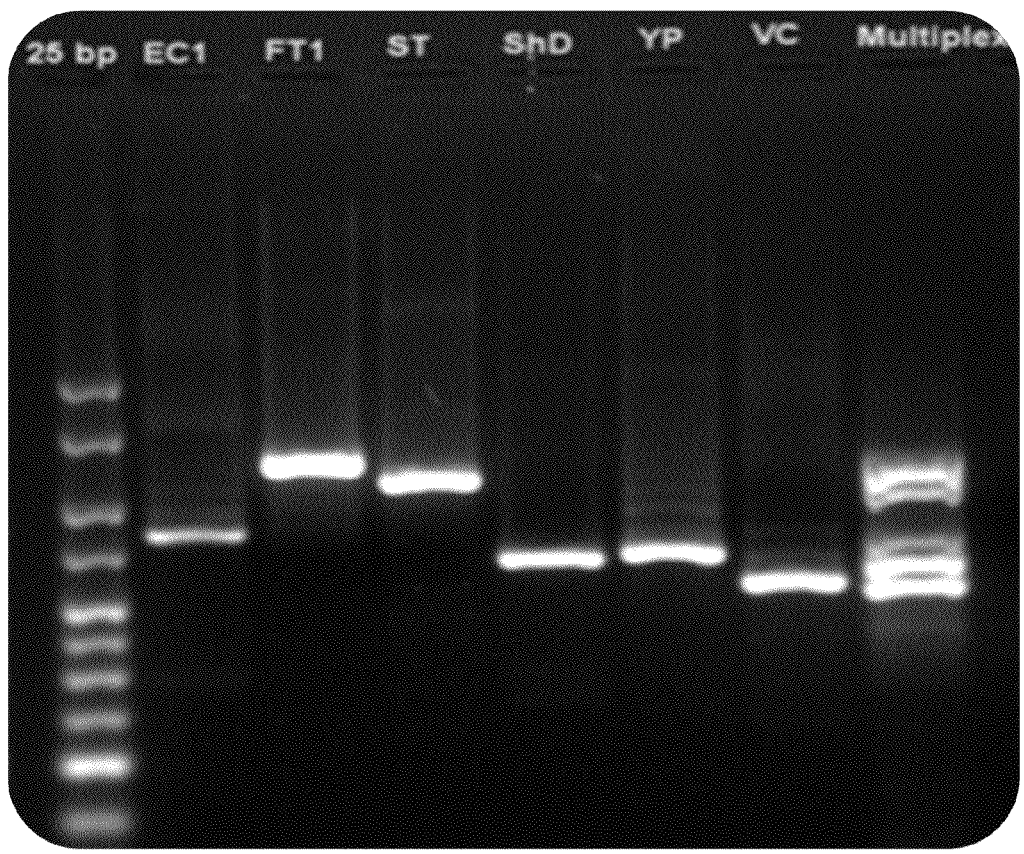
FIG. 6A is a black and white photograph of a gel comparing multiplex PCR to conventional single-target PCR using primers according to embodiments of the invention.
Figure 6B:
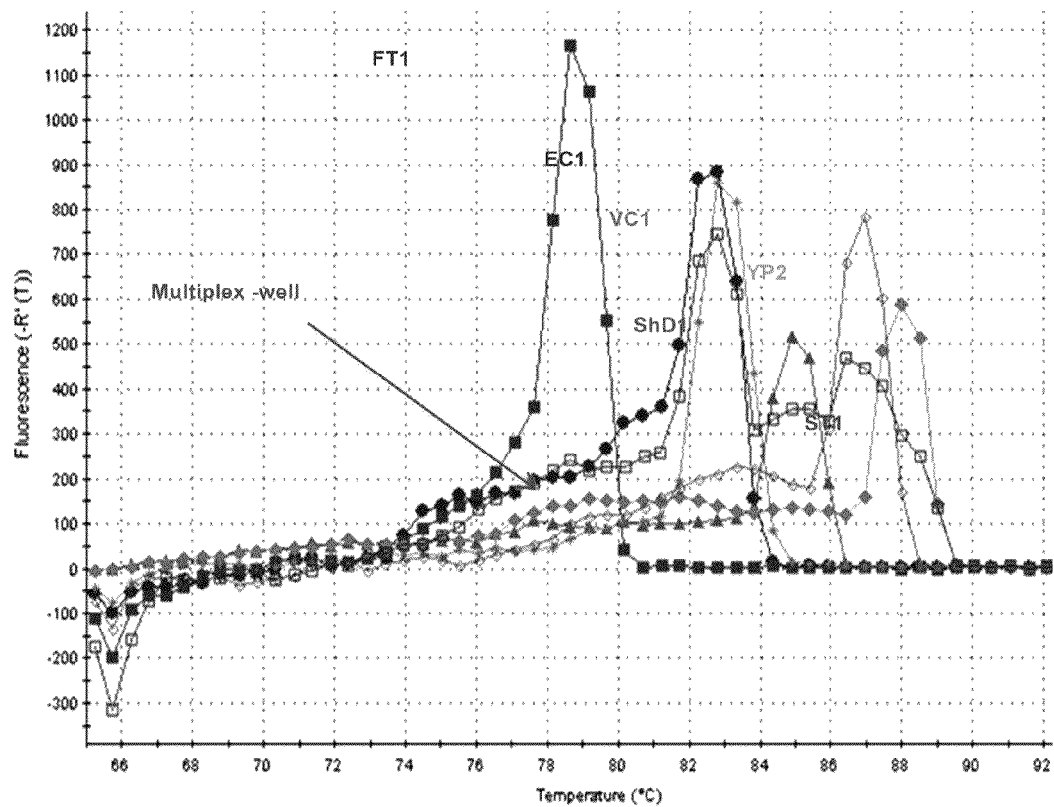
FIG. 6B is color drawing of an amplification plot for real-time multiplex PCR, corresponding to the gel of FIG. 6A.

FIG. 6B is color drawing of an amplification plot for real-time multiplex PCR, corresponding to the gel of FIG. 6A. The purple curve in FIG. 6A indicates dissociation from the multiplex well. The six different organisms' curves overlapped significantly in this experiment.

EXAMPLE 7

Figure 7:
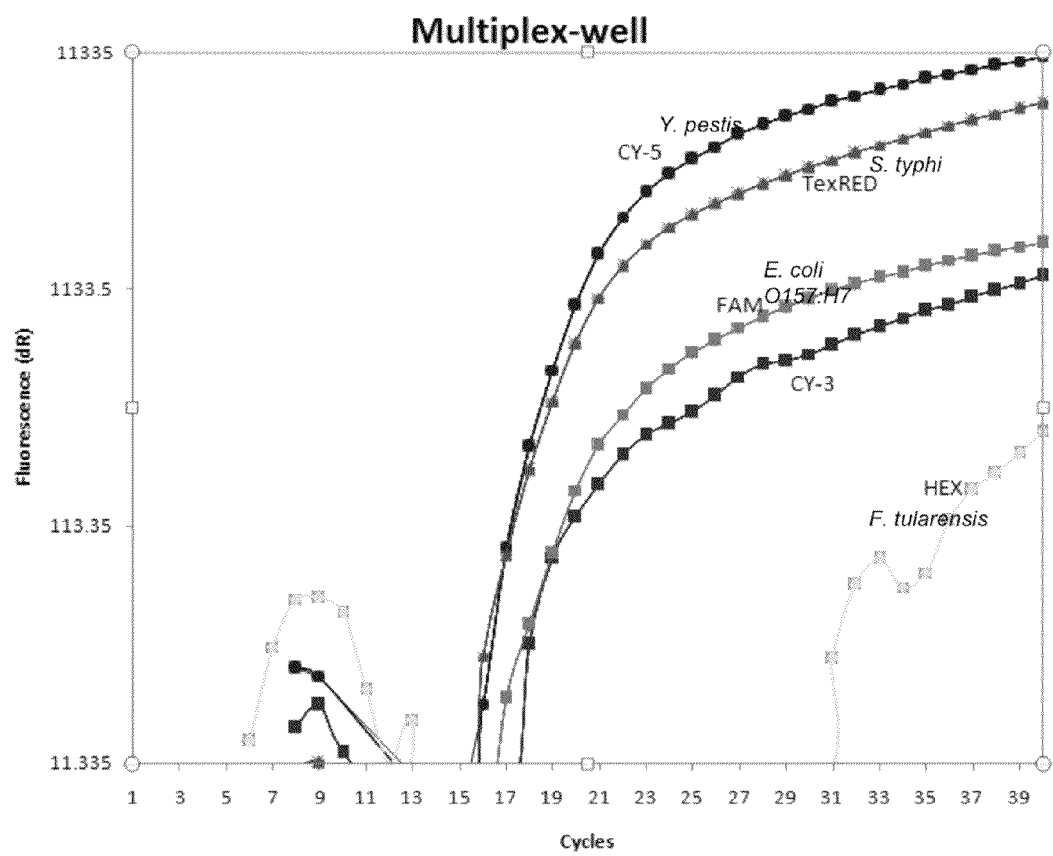
FIG. 7 is color drawing of an amplification plot for a real-time multiplex well PCR experiment.

To overcome the difficulty noted above in the experiment of Example 6 in developing a one-tube multiplex PCR assay capable of detecting 5-6 food threat agents, Applicants designed six specific TaqMan probes within their specific primer regions of the six select agents. These six probes were chosen based on six different reporter dyes with a wide range of emission capabilities, and included FAM, HEX, TAMRA, TEXRED, CY3 and CY5, used to label probes for *E. coli* O157:H7, *F. tularensis* ssp. tularensis, *Y. pestis, S. Typhi, S. dysenteriae* and *V. cholerae*, respectively. FIG. 7 is a color amplification graph showing how the different TaqMan probes help distinguish the various amplification curves for the different agents. Thus, resolution of detection can be improved using such probes for multiplex identification of the pathogens in one tube.

EXAMPLE 7

Another way in which the various primers of embodiments of the present invention may be used to detect individual agents in a multiplex sample is via simultaneous parallel real-time PCR. In this regard, Applicants designed several custom multi-well plates containing an array of primers according to the present invention.

Figure 8B:
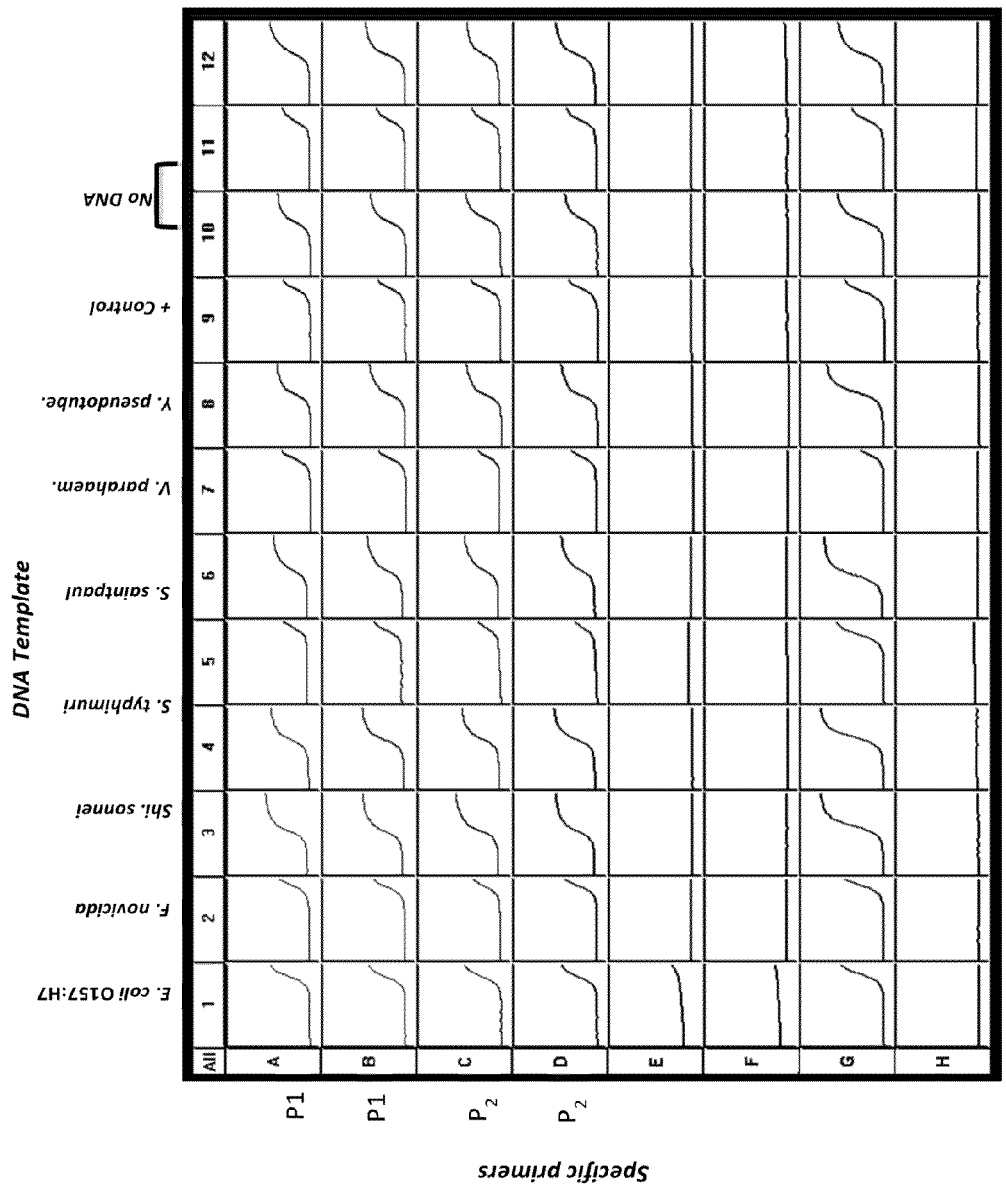
FIG. 8B is an image of the real-time PCR amplification plots for each well of FIG. 8A obtained in one experiment described herein.
Figure 9A:
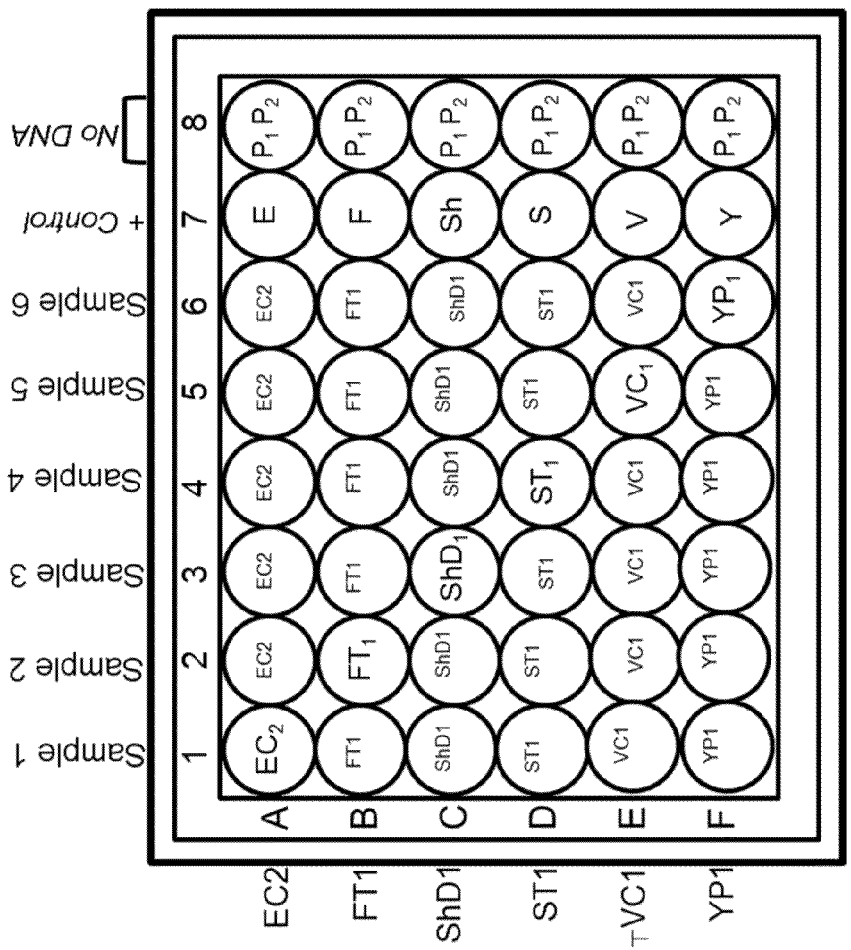
Figure 10A:
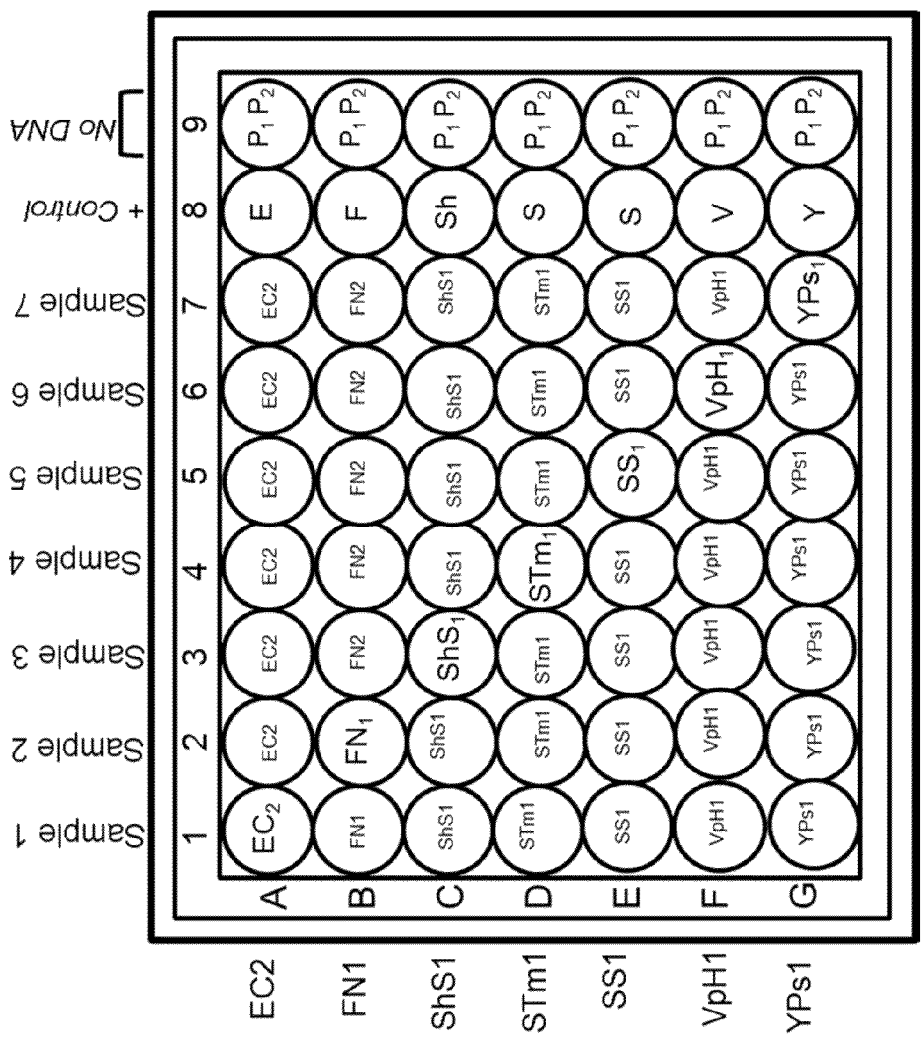

As shown in FIG. 8A, FIG. 9A, and FIG. 10A, three embodiments of such plates were prepared by Applicants using a base 96-well platform, with the array plate in FIG. 8A comprising a full standard 12×8 array plate using all 96 wells (the wells being represented as circles arranged in rows and columns in the figures) while the arrays in FIG. 9A and FIG. 10A used only part of the 12×8 array plate. The 12×8 array depicted in FIG. 8A is adapted to scan for 12 food-threat agents and related pathogens, with each column, as labeled, being assigned to a different organism. To ascertain the fidelity of the primers and the PCR reaction conditions, the primer pairs were spotted in duplicates in the 96-well plate, with two primer pairs (directed at different genes) being included for each target organism. Specifically, rows A and B comprise duplicate wells for a first given primer targeted at a first specific gene, and rows C and D comprise duplicate wells for a second given primer targeted at a second specific gene (if available). The primers placed in each of the wells in rows A through D in the 96-well plate embodiment depicted in FIG. 8A is indicated by that primer's abbreviated name being written in each respective circular well. For example, the two circular wells in the two top rows (rows A and B) and leftmost column (corresponding to *E. coli* O157:H7) in the array of FIG. 8A are each labeled "EC1," meaning that those particular well contain Applicants' primers EC1-Rm and EC1-Fm, while the two wells in the leftmost column and in rows C and D are each labeled "EC2," indicating that they contain Applicants' primers EC2-SLT-T-m and EC2-SLT-F-m. Use of two primers in this manner for each agent, when available, is preferred as it increases the chances that the primers will detect related pathogen strains. Notably, column 3 (corresponding to S. Saintpaul) and column 8 (corresponding to *F. tularensis* ssp. novicida) show only a single primer pair being used in all four corresponding wells in rows A through D as Table 2 lists only one primer for each of those specific organisms. Alternatively, instead of four wells repeating the same primers, one or ordinary skill in the art will appreciate that other organism-specific primers which operate at similar PCR conditions could be substituted in rows C and D to obtain dual detection capability for columns 3 and 8.

Rows E through H comprise various controls, as indicated in the drawing. Specificity was controlled by inclusion of two rows (rows E and F in the schematic of FIG. 8A) of DNA from closely phylogenetically-related bacterial species for the primer pairs used for each intersecting column Row E represents amplification using the first primer pair from related bacterium, and row F represents amplification using the second primer pair of the same related bacterium. Thus, for example, the two primers used to amplify *E. coli* O157:H7 (i.e., EC1) found in column 1 of the array depicted in FIG. 8A, will be tested in rows E and F against *E. coli.* that is not of strain O157:H7. Genus-inclusive specific PCR was included in row G in order to control false negatives. A standard RT-qPCR data analysis method was used to interpret the results. The PCR-Macroarray platform was custom manufactured at Integrated DNA technologies (IDT). Row G represents control positive amplification of the genus of the corresponding food threat agent or food borne pathogen. Finally row H represents assay control without DNA. FIG. 6*b* shows the amplification plots from an actual experiment performed based on the design on FIG. 6*a*, using a custom designed 96-well plate.

FIG. 8A shows that the layout and distribution of wells is adapted for targeted identification of the following food safety threat agents, which comprises 6 select agents and 6 closely related species: *E. coli* O157:H7 (column 1), *S. Typhi* (column 2), S. Saintpaul (column 3), S. Typhimurium (column 4), *S. dysenteriae* (column 5), *S. sonnei* (column 6), *F. tularensis* ssp. tularensis (column 7), *F. tularensis* ssp. *novicida* (column 8), *V. cholerae* (column 9), *V. parahaemolyticus* (column 10), *Y. pestis* (column 11), *Y. pseudotuberculosis* (column 12).

The array of FIG. 8A was constructed and tested under similar conditions to those described above for real-time PCR. The various synthesized primers were deposited in the appropriate wells by IDT (Integrated DNA Technologies), and then pathogen DNA samples were added to wells of rows A through D and G. FIG. 8B is a schematic representation of real-time PCR amplification plots for the array of FIG. 8A obtained in one representative experiment run against a multiplex sample containing each of the 12 pathogens (each grid point representing the individual real-time PCR amplification plot obtained for the primer/DNA placed in the corresponding well. As can be seen, the 12 pathogen array was able to detect each of the pathogens, showing that Applicants' assay has the possibility of detecting twelve major pathogens in a single run.

Since smaller, and more targeted macroarrays, can be useful, Applicants developed and tested the macroarray plates depicted in FIG. 9A and FIG. 10A. FIG. 9A depicts an 8×6 array of 48 total wells (six agents and two control columns—positive and negative), while FIG. 10A comprises a 9×7 array of 63 total wells (seven agents and two control columns) The primers for the 48 well and 63 well plate setup were selected from the primers of Table 2 so that the PCR parameters could be maintained similar across the entire plate, and customized to amplify all the foodthreat agents and foodborne pathogens.

The 48-well array is intended to be food-threat agent inclusive while the 63-well array is intended to be foodborne pathogen inclusive.

The 48-well array of FIG. 9A was developed for *E. coli* O157:H7, *F. tularensis* ssp. tularensis, *S. Typhi*, *S. dysenteriae*, *Y. pestis*, and *V. cholerae*, and this array could be employed, for example, when there is a suspected case of any of these six major food-threat agents (i.e., minimizing the cost of testing for the related agents in a 96-well format). Further or alternatively, this array could also be used as a confirmatory tool for the 96-well PCR assay above. This preferred embodiment of a 48-well array according to the present invention has organism-specific primers in rows A-F. Again, the actual primer placed in each well is indicated in FIG. 9A by the abbreviated primer name indicated within each respective circle in the array schematic. Unlike the embodiment of FIG. 8A, this embodiment did not use redundant cells for each primer, nor multiple primers for each target. Only one primer pair was spotted per row. Columns 1-8 are adapted to receive DNA samples to be tested for the six specific food-threat agents; a given sample should have an equal amount aliquoted into each well in the same column to see whether it contains DNA from one or more of the six organisms. If a sample contained only *Y. pestis* and *V. cholerae* and was placed into the wells of column 1, then the column 1 wells in rows E and F would show positive real-time PCR results while rows A-D would show a negative result. In this manner, the microplate array of FIG. 9A can receive up to six different test samples (each of which containing DNA from any number of organisms) simultaneously. In practice, the columns of the array in FIG. 9A can each receive any DNA sample (even two or more receiving the same sample to provide redundancy).

Columns 7 and 8 of the array of FIG. 9A serve as positive and negative controls respectively, as explained above. The various wells in column 7 are coated with genus specific primers providing the assay with a positive control, and wells in column 8 are coated with primers of the respective select agents and serve as a non-template control.

Figure 9B:
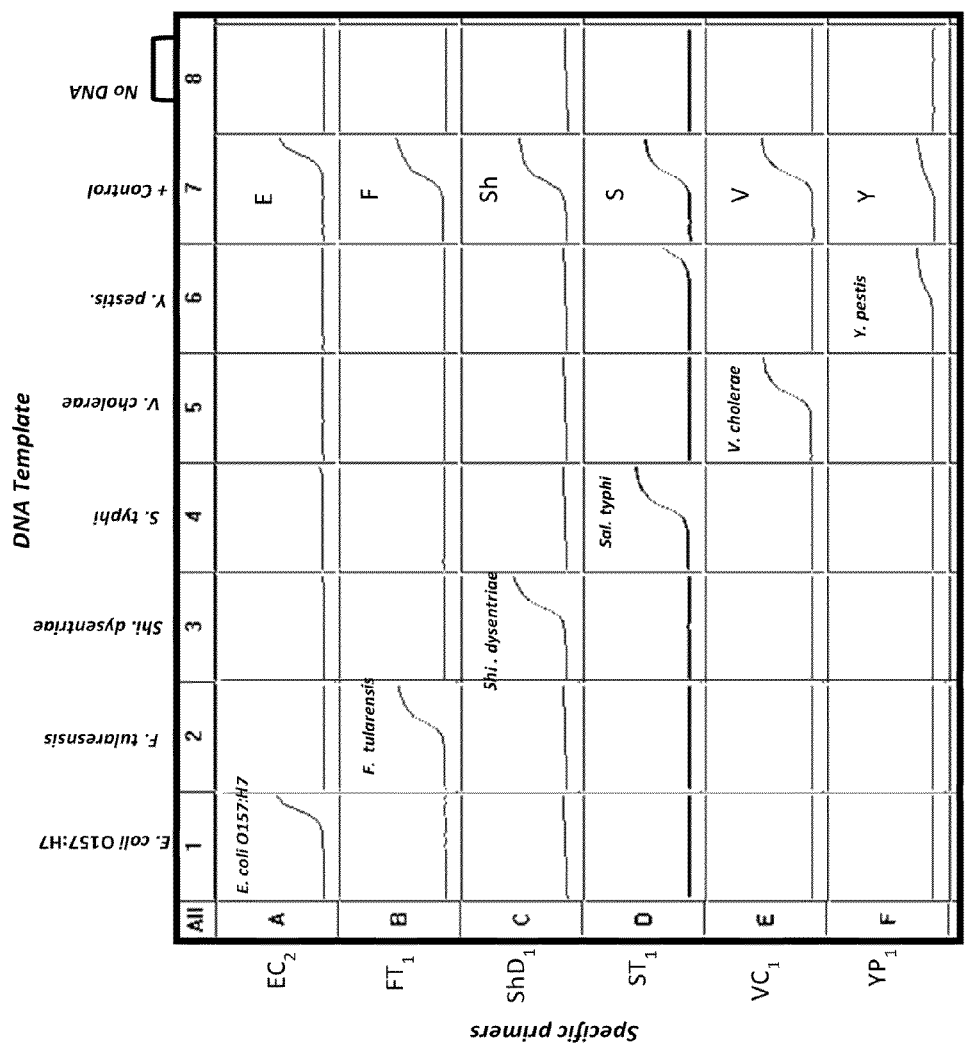
FIG. 9B is an image of the real-time PCR amplification plots for each well of FIG. 9A obtained in one experiment described herein.

FIG. 9B is a graphical depiction of a grid of real-time PCR amplification plots from an actual experiment performed on a 48-well array constructed as depicted in FIG. 9A. This 48-well array of FIG. 9A was created by IDT and tested by Applicants by aliquoting approximately equal amounts of DNA samples as follows: *E. coli* O157:H7 (column 1), *F. tularensis* ssp. tularensis (column 2), *S. Typhi* (column 3), *S. dysenteriae* (column 4), *Y. pestis* (column 5), and *V. cholerae* (column 6). The plate was thereafter run under real-time PCR conditions as described above for the 12×8 array and the compiled amplification plot represented in FIG. 9B was produced. As shown in that figure, amplification plots were produced only where the test sample contained the specific target agent for the primer.

FIG. 10A is a schematic diagram of a separate array that was designed by Applicants for the bacteria closely related to the threat agents and considered most commonly encountered food borne pathogens. Similar to FIG. 9A, primers were spotted in rows (a single row per primer pair), and in use DNA samples would be spotted down columns.

The particular macroarray depicted in FIG. 10A was developed by Applicants for *E. coli* O157:H7, *F. tularensis* ssp. novidica, *S. sonnei*, Typhimurium, S. Saintpaul, *V. parahaemolyticus*, and *Y. pseudotuberculosis*, and this array could be employed, for example, when there is a suspected case of any of these seven food-borne pathogens or as a confirmatory tool. This preferred embodiment of a 63-well array according to the present invention has organism-specific primers in rows A-G, and the actual primer placed in each well according to this preferred embodiment is indicated in FIG. 10A by the abbreviated primer name indicated within each respective circle representing each well. Like the 48-well array embodiment, this embodiment also does not use redundant cells for each primer, nor multiple primers for each target. Columns 1-9 are adapted to receive DNA samples to be tested for the six specific food-threat agents; a given sample should have an equal amount aliquoted into each well in the same column to see whether it contains DNA from one or more of the six organisms.

Figure 10B:
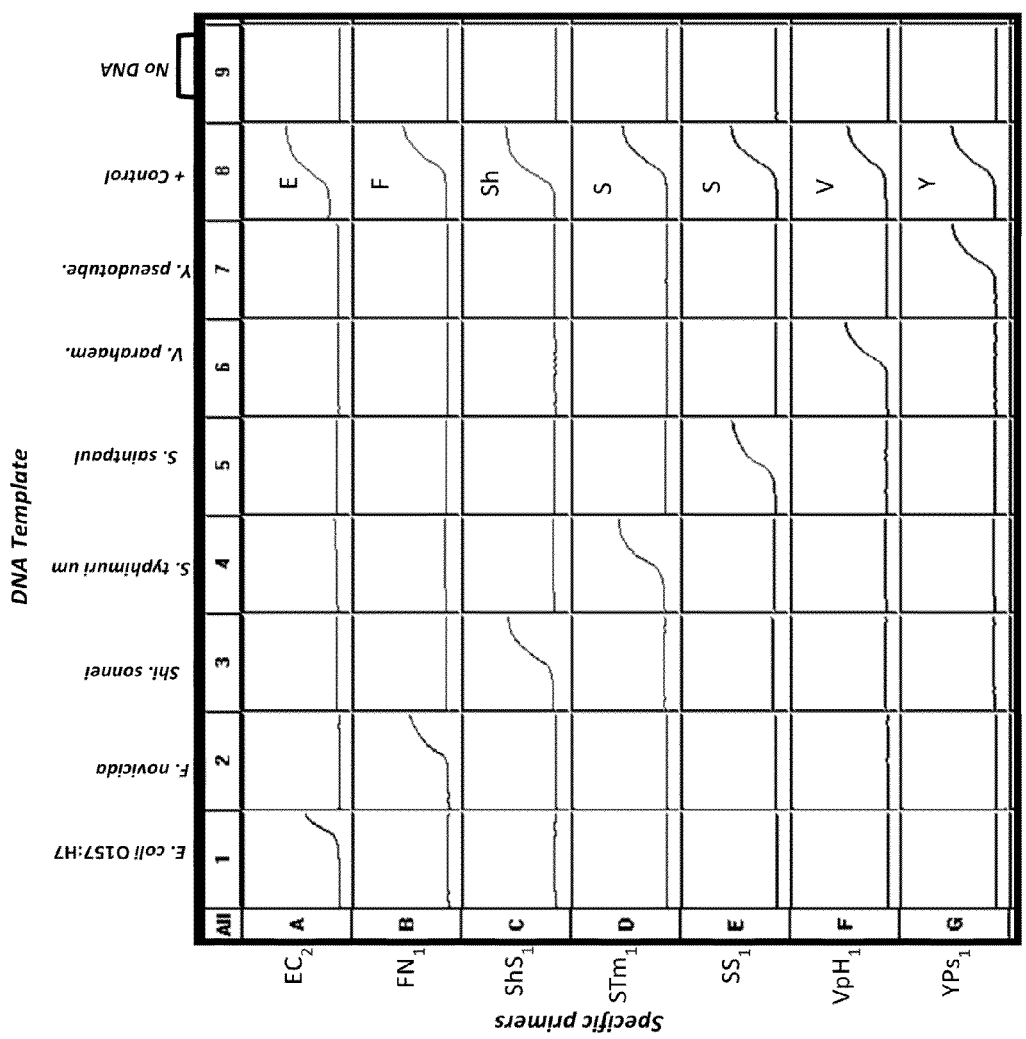
FIG. 10B is an image of the real-time PCR amplification plots for each well of FIG. 10A obtained in one experiment described herein.

FIG. 10B is an image depicting the labeled output from real-time PCR showing amplification plots for each well of FIG. 10A obtained in a test experiment run by Applicants. The PCR-microplate array was made by IDT at Applicants request, and then Applicants tested the microplate array with seven test samples, each containing a different one of the seven food-borne pathogens for which the plate tests. As shown in FIG. 10B, Applicants in conducting real-time PCR detected, as expected, selective amplification of the food-borne pathogens *E. coli* O157:H7 in well A1, *F. tularensis* ssp. novicida in well B2, *S. sonnei* in well C3, *S. enterica* ssp. enterica serovar Typhimurium in well D4, *S. enterica* ssp. enterica serovar Saintpaul in well E5, *V. parahaemolyticus* well F6, and *Y. pseudotuberculosis* in well G7. Wells in column 8 were coated with genus specific primers providing the assay with a positive control, and wells in column 9 were coated with primers of the respective select agents and serve as a non-template control.

In this manner, the experiments described herein in Example 7 demonstrate the suitability of the various primers discovered by Applicants for combined simultaneous use in real-time PCR screens for detecting and identifying food threat agents and food-borne pathogens with levels of specificity and sensitivity not previously obtained by others in the art.

Having described preferred embodiments of the invention, it will now become apparent to those of ordinary skill in the art that other embodiments incorporating these concepts may be used. Accordingly, it is submitted that that the invention should not be limited to the described embodiments but rather should be limited only by the spirit and scope of the appended claims.

Thus, although the invention has been described and illustrated with a certain degree of particularity, it is understood that the present disclosure has been made only by way of example, and that numerous changes in the combination and arrangement of steps, ingredients, or processes can be resorted to by those skilled in the art without departing from the spirit and scope of the invention, as will be claimed hereafter.

REFERENCE

Benoit, P. W., Donahue, D. W., 2003, Methods for rapid separation and concentration of bacteria in food that bypass time-consuming cultural enrichment. J Food Prot 66, 1935-1948.

Dwivedi, H. P., Jaykus, L. A., 2011, Detection of pathogens in foods: the current state-of-the-art and future directions. Crit. Rev Microbiol 37, 40-63.

Edwards, M. C., Gibbs, R. A., 1994, Multiplex PCR: Advantages, Development, and Applications. Genome Research 3, S65-S75.

Fukushima, H., Kawase, J., Etoh, Y., Sugama, K., Yashiro, S., Lida, N., Yamaguchi, K., 2010, Simultaneous Screening of 24 Target Genes of Foodborne Pathogens in 35 Foodborne Outbreaks Using Multiplex Real-Time SYBR Green PCR Analysis. Int J Microbiol 2010.

Jin, Q., Yuan, Z., Xu, J., Wang, Y., Shen, Y., Lu, W., Wang, J., Liu, H., Yang, J., Yang, F., Zhang, X., Zhang, J., Yang, G., Wu, H., Qu, D., Dong, J., Sun, L., Xue, Y., Zhao, A., Gao, Y., Zhu, J., Kan, B., Ding, K., Chen, S., Cheng, H., Yao, Z., He, B., Chen, R., Ma, D., Qiang, B., Wen, Y., Hou, Y., Yu, J., 2002, Genome sequence of *Shigella flexneri* 2a: insights into pathogenicity through comparison with genomes of *Escherichia coli* K12 and O157. Nucleic Acids Res 30, 4432-4441.

Jothikumar, N., Griffiths, M. W., 2002, Rapid detection of *Escherichia coli* O157:H7 with multiplex real-time PCR assays. Appl Environ Microbiol 68, 3169-3171.

Pupo, G. M., Lan, R., Reeves, P. R., 2000, Multiple independent origins of *Shigella* clones of *Escherichia coli* and convergent evolution of many of their characteristics. Proc Natl Acad Sci USA 97, 10567-10572.

Skottman, T., Piiparinen, H., Hyytiäinen, H., Myllys, V., Skurnik, M., Nikkari, S., 2007, Simultaneous real-time PCR detection of *Bacillus anthracis, Francisella tularensis* and *Yersinia pestis*. Eur J Clin Microbiol Infect Dis 26, 207-211.

Song, Y., Tong, Z., Wang, J., Wang, L., Guo, Z., Han, Y., Zhang, J., Pei, D., Zhou, D., Qin, H., Pang, X., Zhai, J., Li, M., Cui, B., Qi, Z., Jin, L., Dai, R., Chen, F., Li, S., Ye, C., Du, Z., Lin, W., Yu, J., Yang, H., Huang, P., Yang, R., 2004, Complete genome sequence of *Yersinia pestis* strain 91001, an isolate avirulent to humans. DNA Res 11, 179-197.

Wilson, W. J., Erler, A. M., Nasarabadi, S. L., Skowronski, E. W., Imbro, P. M., 2005, A multiplexed PCR-coupled liquid bead array for the simultaneous detection of four biothreat agents. Mol Cell Probes 19, 137-144.

Zhou, D., Tong, Z., Song, Y., Han, Y., Pei, D., Pang, X., Zhai, J., Li, M., Cui, B., Qi, Z., Jin, L., Dai, R., Du, Z., Wang, J., Guo, Z., Huang, P., Yang, R., 2004, Genetics of metabolic variations between *Yersinia pestis* biovars and the proposal of a new biovar, microtus. J Bacteriol 186, 5147-5152.

BIOSEQUENCES

SEQ. ID NO. 1
cagacgaaga tggtcaaaac gcg

SEQ. ID NO. 2
agtttacgat agacttttcg accc

SEQ. ID NO. 3
tctggttgac tctcttcatt cacgg

SEQ. ID NO. 4
tacagagaga atttcgtcag gcactg

SEQ. ID NO. 5
gcacttcaaa ctgctggta ata

SEQ. ID NO. 6
tgcacctacg atgtttttga cc

SEQ. ID NO. 7
gaaggtcttc tagaaaattc tgctc

SEQ. ID NO. 8
ttgctggtaa ttcgtagata atatc

SEQ. ID NO. 9
ggaagcatag ctattagcat attctgg

SEQ. ID NO. 10
ttgtctaaag caaatattga gtggg

SEQ. ID NO. 11
atgcaaaaga taaggctaac tctt

SEQ. ID NO. 12
gaatcaatat tcgttaggtc ttca

SEQ. ID NO. 13
ggaacaccgt arttgttagc ttgg

SEQ. ID NO. 14
attggtatct gtgctcacgt tgatg

SEQ. ID NO. 15
atggtgtcgt cgataatatc ggcc

SEQ. ID NO. 16
aagagcgtat ctggagtatt tcacc

SEQ. ID NO. 17
gtgatggttt gttagattct accaa

SEQ. ID NO. 18
atgcaattgc caatagacaa cca

SEQ. ID NO. 19
tattgctgcg gtcatacact gcc

SEQ. ID NO. 20
ctgatcgaac ttcgatgcca atcc

SEQ. ID NO. 21
cacagtgcct ctgcggagct tcg

SEQ. ID NO. 22
gagagttctg actttatccc g

SEQ. ID NO. 23
tcaagaatag agcgaatttc atcc

SEQ. ID NO. 24
tgctttttat cgattccatg accc

SEQ. ID NO. 25
atgacctttg cagctatcga gtaa

SEQ. ID NO. 26
aacgagagga cgtaatcgcg aa

SEQ. ID NO. 27
cagattcatc catcaaaaaa atggg

SEQ. ID NO. 28
gctaatgcgg ctctgaacct gtg

SEQ. ID NO. 29
gacattctac gtaaccagct tgct

SEQ. ID NO. 30
tgagcgttca cccatggcta actgtt

SEQ. ID NO. 31
gggagtggtt aaagcaaccg tgtca

SEQ. ID NO. 32
tcacagactc ttcggtccat tcctt

SEQ. ID NO. 33
aaggtttatc agtattagtc gtgtg

SEQ. ID NO. 34
ttgctggact gggttgacca taggg

SEQ. ID NO. 35
cctcagggta tccttcatcc tttc

SEQ. ID NO. 36
cttcagcata tgcacatgga acacc

SEQ. ID NO. 37
ggcgtcgtct tctaaatact gttc

| BIOSEQUENCES |
|---|
| SEQ. ID NO. 38<br>atgaaacacc atgcacaaac ttct |
| SEQ. ID NO. 39<br>cttttttaaga gcggcagata tca |
| SEQ. ID NO. 40<br>atgactgcga ctaacttatt cgtc |
| SEQ. ID NO. 41<br>tggacattcc atacctgcta tcg |
| SEQ. ID NO. 42<br>accacggatt tgacattctt ta |
| SEQ. ID NO. 43<br>cagtgtttgc atttaatggc tt |
| SEQ. ID NO. 44<br>ccagctatta tagcaaatag taaggg |
| SEQ. ID NO. 45<br>ggcaatcaac aatacagccg tt |
| SEQ. ID NO. 46<br>attgccgttc gggtctttcc |
| SEQ. ID NO. 47<br>agcaatgtgt ctgaactttc ttca |
| SEQ. ID NO. 48<br>catattgccg tcaccgacta cacc |
| SEQ. ID NO. 49<br>caggcaacgc tgagtattag gt |
| SEQ. ID NO. 50<br>ctgctgatgt tgccattagt atgg |
| SEQ. ID NO. 51<br>tcatctaaag caccaacgaa yacc |
| SEQ. ID NO. 52<br>tatttgttgc tcgcaaagtt gcc |

The invention claimed is:

1. A microplate array for testing a sample simultaneously for a plurality of microorganisms that are foodborne pathogens or food threat agents, said array comprising:

two or more primer pairs placed in a plurality of locations on a microplate for receiving test samples, said two or more primer pairs being adapted to detect and distinguish with specificity DNA from at least two different microorganisms that are foodborne pathogens or food threat agents, wherein all said primer pairs have similar melting temperatures such that they can be simultaneously run under the same PCR conditions, and said primer pairs comprising at least one primer pair selected from the primer pairs of: SEQ ID NO: 25 and SEQ ID NO: 26; SEQ ID NO: 29 and SEQ ID NO: 30; SEQ ID NO: 31 and SEQ ID NO: 32; SEQ ID NO: 33 and SEQ ID NO: 34; SEQ ID NO: 47 and SEQ ID NO: 48; SEQ ID NO: 19 and SEQ ID NO: 20; and SEQ ID NO: 43 and SEQ ID NO: 44.

2. The array according to claim 1, wherein at least one of said primers has a sequence selected from the group consisting of SEQ ID NO: 25 and SEQ ID NO: 26.

3. array according to claim 1, wherein at least one of said primers has a sequence selected from the group consisting of SEQ ID NO: 29 and SEQ ID NO: 30.

4. The array according to claim 1, wherein at least one of said primers has a sequence selected from the group consisting of SEQ ID NO: 31 and SEQ ID NO: 32.

5. The array according to claim 1, wherein at least one of said primers has a sequence selected from the group consisting of SEQ ID NO: 7 and SEQ ID NO: 8.

6. The array according to claim 1, wherein at least one of said primers has a sequence selected from the group consisting of SEQ ID NO: 33 and SEQ ID NO: 34.

7. The array according to claim 1, wherein at least one of said primers has a sequence selected from the group consisting of SEQ ID NO: 43 and SEQ ID NO: 44.

8. The array according to claim 1, wherein at least one of said primers has a sequence selected from the group consisting of SEQ ID NO: 47 and SEQ ID NO: 48.

9. The array according to claim 1, wherein at least one of said primers has a sequence selected from the group consisting of SEQ ID NO: 19 and SEQ ID NO: 20.

10. The array according to claim 1, wherein at least one of said primers has a sequence selected from the group consisting of SEQ ID NO: 37 and SEQ ID NO: 38.

11. The array according to claim 1, further comprising at least three or more primer pairs, and wherein at least two of said at least three primer pairs are adapted to detect different genes for the same microorganism.

12. A multiplex real-time PCR system for use in simultaneously testing for a plurality of microorganisms that are foodborne pathogens or food threat agents, said system comprising:

a container for receiving test samples, said container containing two or more primer pairs, said two or more primer pairs being adapted to detect and distinguish with specificity DNA from at least two different microorganisms that are foodborne pathogens or food threat agents, wherein all said primer pairs have similar melting temperatures such that they can be simultaneously run under the same PCR conditions, and wherein said primer pairs comprise at least one primer pair selected from the primer pairs of: SEQ ID NO: 25 and SEQ ID NO: 26; SEQ ID NO: 29 and SEQ ID NO: 30; SEQ ID NO: 31 and SEQ ID NO: 32; SEQ ID NO: 33 and SEQ ID NO: 34; SEQ ID NO: 47 and SEQ ID NO: 48; SEQ ID NO: 19 and SEQ ID NO: 20; and SEQ ID NO: 43 and SEQ ID NO: 44.

13. The system according to claim 12, said container further containing a different TaqMan probe for each primer pair, said TaqMan probe each being designed to bind to DNA regions flanked by the primer regions in genomes of the at least two different microorganisms, each said probe serving as a different reporter dye having emission capabilities distinguishable from other ones of said probes.

14. The system according to claim 13, wherein said TaqMan probes include one or more reporter dyes selected from the group consisting of FAM, HEX, TAMRA, TEXRED, CY3 and CY5.

15. The system according to claim 13, wherein said probes are capable of selectively detecting two or more target microorganisms selected from the group consisting of *Escherichia coli, Salmonella enterica* subspecies enterica serovar Typhimurium, *Salmonella enterica* subspecies enterica serovar Saintpaul, *Salmonella enterica* subspecies enterica serovar Typhi, *Shigella sonnei, Shigella dysenteriae, Francisella tularensis* subspecies tularensis, *Francisella tularensis* subspecies novicida, *Y. pestis, Y. pseudotuberculosis, Vibrio parahaemolyticus*, and *Vibrio cholerae*.

* * * * *

SEQUENCE LISTING

```
<160> NUMBER OF SEQ ID NOS: 52

<210> SEQ ID NO 1
<211> LENGTH: 23
<212> TYPE: DNA
<213> ORGANISM: Escherichia coli O157:H7 EDL933

<400> SEQUENCE: 1
cagacgaaga tggtcaaaac gcg                                        23

<210> SEQ ID NO 2
<211> LENGTH: 24
<212> TYPE: DNA
<213> ORGANISM: Escherichia coli O157:H7 EDL933

<400> SEQUENCE: 2
agtttacgat agacttttcg accc                                       24

<210> SEQ ID NO 3
<211> LENGTH: 25
<212> TYPE: DNA
<213> ORGANISM: Escherichia coli O157:H7 str EC4115

<400> SEQUENCE: 3
tctggttgac tctcttcatt cacgg                                      25

<210> SEQ ID NO 4
<211> LENGTH: 26
<212> TYPE: DNA
<213> ORGANISM: Escherichia coli O157:H7 str EC4115

<400> SEQUENCE: 4
tacagagaga atttcgtcag gcactg                                     26

<210> SEQ ID NO 5
<211> LENGTH: 23
<212> TYPE: DNA
<213> ORGANISM: Escherichia coli CFT073

<400> SEQUENCE: 5
```
gcacttcaaa ctggctggta ata                                            23

<210> SEQ ID NO 6
<211> LENGTH: 22
<212> TYPE: DNA
<213> ORGANISM: Escherichia coli CFT073

<400> SEQUENCE: 6
tgcacctacg atgtttttga cc                                             22

<210> SEQ ID NO 7
<211> LENGTH: 25
<212> TYPE: DNA
<213> ORGANISM: Francisella tularensis subsp. tularensis Schu4

<400> SEQUENCE: 7
gaaggtcttc tagaaaattc tgctc                                          25

<210> SEQ ID NO 8
<211> LENGTH: 25
<212> TYPE: DNA
<213> ORGANISM: Francisella tularensis subsp. tularensis Schu4

<400> SEQUENCE: 8
ttgctggtaa ttcgtagata atatc                                          25

<210> SEQ ID NO 9
<211> LENGTH: 27
<212> TYPE: DNA
<213> ORGANISM: Francisella tularensis subsp. tularensis Schu4

<400> SEQUENCE: 9
ggaagcatag ctattagcat attctgg                                        27

<210> SEQ ID NO 10
<211> LENGTH: 25
<212> TYPE: DNA
<213> ORGANISM: Francisella tularensis subsp. tularensis Schu4

<400> SEQUENCE: 10
ttgtctaaag caaatattga gtggg                                          25

<210> SEQ ID NO 11
<211> LENGTH: 24
<212> TYPE: DNA
<213> ORGANISM: Francisella tularensis subsp. novicida U112

<400> SEQUENCE: 11
atgcaaaaga taaggctaac tctt                                           24

<210> SEQ ID NO 12
<211> LENGTH: 24
<212> TYPE: DNA
<213> ORGANISM: Francisella tularensis subsp. novicida U112

<400> SEQUENCE: 12
gaatcaatat tcgttaggtc ttca                                           24

<210> SEQ ID NO 13
<211> LENGTH: 24
<212> TYPE: DNA
<213> ORGANISM: Francisella tularensis subsp. holarctica OSU18

<400> SEQUENCE: 13
ggaacaccgt arttgttagc ttgg                                          24

<210> SEQ ID NO 14
<211> LENGTH: 25
<212> TYPE: DNA
<213> ORGANISM: Francisella tularensis subsp. holarctica OSU18

<400> SEQUENCE: 14
attggtatct gtgctcacgt tgatg                                         25

<210> SEQ ID NO 15
<211> LENGTH: 24
<212> TYPE: DNA
<213> ORGANISM: Shigella dysenteriae Sd197

<400> SEQUENCE: 15
atggtgtcgt cgataatatc ggcc                                          24

<210> SEQ ID NO 16
<211> LENGTH: 25
<212> TYPE: DNA
<213> ORGANISM: Shigella dysenteriae Sd197

<400> SEQUENCE: 16
aagagcgtat ctggagtatt tcacc                                         25

<210> SEQ ID NO 17
<211> LENGTH: 25
<212> TYPE: DNA
<213> ORGANISM: Shigella dysenteriae Sd197

<400> SEQUENCE: 17
gtgatggttt gttagattct accaa                                         25

<210> SEQ ID NO 18
<211> LENGTH: 23
<212> TYPE: DNA
<213> ORGANISM: Shigella dysenteriae Sd197

<400> SEQUENCE: 18
atgcaattgc caatagacaa cca                                           23

<210> SEQ ID NO 19
<211> LENGTH: 23
<212> TYPE: DNA
<213> ORGANISM: Shigella sonnei Ss046

<400> SEQUENCE: 19
tattgctgcg gtcatacact gcc                                           23

<210> SEQ ID NO 20
<211> LENGTH: 24
<212> TYPE: DNA
<213> ORGANISM: Shigella sonnei Ss046

<400> SEQUENCE: 20
ctgatcgaac ttcgatgcca atcc                                          24

<210> SEQ ID NO 21
<211> LENGTH: 23
<212> TYPE: DNA
<213> ORGANISM: Shigella sonnei Ss046

```
<400> SEQUENCE: 21
cacagtgcct ctgcggagct tcg                                               23

<210> SEQ ID NO 22
<211> LENGTH: 21
<212> TYPE: DNA
<213> ORGANISM: Shigella sonnei Ss046

<400> SEQUENCE: 22
gagagttctg actttatccc g                                                 21

<210> SEQ ID NO 23
<211> LENGTH: 24
<212> TYPE: DNA
<213> ORGANISM: Salmonella enterica subsp. enterica serovar Typhimurium
      LT2

<400> SEQUENCE: 23
tcaagaatag agcgaatttc atcc                                              24

<210> SEQ ID NO 24
<211> LENGTH: 24
<212> TYPE: DNA
<213> ORGANISM: Salmonella enterica subsp. enterica serovar Typhimurium
      LT2

<400> SEQUENCE: 24 tgcttttat cgattccatg accc                                               24

<210> SEQ ID NO 25
<211> LENGTH: 24
<212> TYPE: DNA
<213> ORGANISM: Salmonella enterica subsp. enterica serovar Typhi Ty2

<400> SEQUENCE: 25
atgacctttg cagctatcga gtaa                                              24

<210> SEQ ID NO 26
<211> LENGTH: 22
<212> TYPE: DNA
<213> ORGANISM: Salmonella enterica subsp. enterica serovar Typhi Ty2

<400> SEQUENCE: 26
aacgagagga cgtaatcgcg aa                                                22

<210> SEQ ID NO 27
<211> LENGTH: 25
<212> TYPE: DNA
<213> ORGANISM: Salmonella enterica subsp. enterica serovar Typhimurium
      LT2

<400> SEQUENCE: 27
cagattcatc catcaaaaaa atggg                                             25

<210> SEQ ID NO 28
<211> LENGTH: 23
<212> TYPE: DNA
<213> ORGANISM: Salmonella enterica subsp. enterica serovar Typhimurium
      LT2

<400> SEQUENCE: 28
gctaatgcgg ctctgaacct gtg                                               23
```

<210> SEQ ID NO 29
<211> LENGTH: 24
<212> TYPE: DNA
<213> ORGANISM: Salmonella enterica subsp. enterica serovar Typhimurium LT2

<400> SEQUENCE: 29
gacattctac gtaaccagct tgct                                            24

<210> SEQ ID NO 30
<211> LENGTH: 26
<212> TYPE: DNA
<213> ORGANISM: Salmonella enterica subsp. enterica serovar Typhimurium LT2

<400> SEQUENCE: 30
tgagcgttca cccatggcta actgtt                                          26

<210> SEQ ID NO 31
<211> LENGTH: 25
<212> TYPE: DNA
<213> ORGANISM: Salmonella enterica subsp. enterica serovar Saintpaul SARA23

<400> SEQUENCE: 31
gggagtggtt aaagcaaccg tgtca                                           25

<210> SEQ ID NO 32
<211> LENGTH: 25
<212> TYPE: DNA
<213> ORGANISM: Salmonella enterica subsp. enterica serovar Saintpaul SARA23

<400> SEQUENCE: 32
tcacagactc ttcggtccat tcctt                                           25

<210> SEQ ID NO 33
<211> LENGTH: 25
<212> TYPE: DNA
<213> ORGANISM: Vibrio cholerae M66-2 chromosome I

<400> SEQUENCE: 33
aaggtttatc agtattagtc gtgtg                                           25

<210> SEQ ID NO 34
<211> LENGTH: 25
<212> TYPE: DNA
<213> ORGANISM: Vibrio cholerae M66-2 chromosome I

<400> SEQUENCE: 34
ttgctggact gggttgacca taggg                                           25

<210> SEQ ID NO 35
<211> LENGTH: 24
<212> TYPE: DNA
<213> ORGANISM: Vibrio cholerae O1 biovar El Tor str. N16961

<400> SEQUENCE: 35
cctcagggta tccttcatcc tttc                                            24

<210> SEQ ID NO 36
<211> LENGTH: 25
<212> TYPE: DNA
<213> ORGANISM: Vibrio cholerae O1 biovar El Tor str. N16961

-continued

<400> SEQUENCE: 36
cttcagcata tgcacatgga acacc                                          25

<210> SEQ ID NO 37
<211> LENGTH: 24
<212> TYPE: DNA
<213> ORGANISM: Vibrio parahaemolyticus RIMD 2210633

<400> SEQUENCE: 37
ggcgtcgtct tctaaatact gttc                                           24

<210> SEQ ID NO 38
<211> LENGTH: 24
<212> TYPE: DNA
<213> ORGANISM: Vibrio parahaemolyticus RIMD 2210633

<400> SEQUENCE: 38
atgaaacacc atgcacaaac ttct                                           24

<210> SEQ ID NO 39
<211> LENGTH: 23
<212> TYPE: DNA
<213> ORGANISM: Vibrio parahaemolyticus RIMD 2210633

<400> SEQUENCE: 39 cttttttaaga gcggcagata tca                                           23

<210> SEQ ID NO 40
<211> LENGTH: 24
<212> TYPE: DNA
<213> ORGANISM: Vibrio parahaemolyticus RIMD 2210633

<400> SEQUENCE: 40
atgactgcga ctaacttatt cgtc                                           24

<210> SEQ ID NO 41
<211> LENGTH: 23
<212> TYPE: DNA
<213> ORGANISM: Vibrio vulnificus YJ016

<400> SEQUENCE: 41
tggacattcc atacctgcta tcg                                            23

<210> SEQ ID NO 42
<211> LENGTH: 22
<212> TYPE: DNA
<213> ORGANISM: Vibrio vulnificus YJ016

<400> SEQUENCE: 42
accacggatt tgacattctt ta                                             22

<210> SEQ ID NO 43
<211> LENGTH: 22
<212> TYPE: DNA
<213> ORGANISM: Yersinia pestis strain CO92

<400> SEQUENCE: 43
cagtgtttgc atttaatggc tt                                             22

<210> SEQ ID NO 44
<211> LENGTH: 20
<212> TYPE: DNA

<213> ORGANISM: Yersinia pestis strain CO92

<400> SEQUENCE: 44
attgccgttc gggtctttcc                                                  20

<210> SEQ ID NO 45
<211> LENGTH: 26
<212> TYPE: DNA
<213> ORGANISM: Yersinia pestis strain CO92

<400> SEQUENCE: 45
ccagctatta tagcaaatag taaggg 26

<210> SEQ ID NO 46
<211> LENGTH: 22
<212> TYPE: DNA
<213> ORGANISM: Yersinia pestis strain CO92

<400> SEQUENCE: 46
ggcaatcaac aatacagccg tt 22

<210> SEQ ID NO 47
<211> LENGTH: 24
<212> TYPE: DNA
<213> ORGANISM: Yersinia pseudotuberculosis IP 32953

<400> SEQUENCE: 47
agcaatgtgt ctgaactttc ttca 24

<210> SEQ ID NO 48
<211> LENGTH: 24
<212> TYPE: DNA
<213> ORGANISM: Yersinia pseudotuberculosis IP 32953

<400> SEQUENCE: 48
catattgccg tcaccgacta cacc 24

<210> SEQ ID NO 49
<211> LENGTH: 22
<212> TYPE: DNA
<213> ORGANISM: Yersinia pseudotuberculosis IP 32953

<400> SEQUENCE: 49
caggcaacgc tgagtattag gt 22

<210> SEQ ID NO 50
<211> LENGTH: 24
<212> TYPE: DNA
<213> ORGANISM: Yersinia pseudotuberculosis IP 32953

<400> SEQUENCE: 50
ctgctgatgt tgccattagt atgg 24

<210> SEQ ID NO 51
<211> LENGTH: 24
<212> TYPE: DNA
<213> ORGANISM: Yersinia pseudotuberculosis IP 32953

<400> SEQUENCE: 51
tcatctaaag caccaacgaa yacc 24

<210> SEQ ID NO 52
<211> LENGTH: 23

-continued

<212> TYPE: DNA
<213> ORGANISM: Yersinia pseudotuberculosis IP 32953

<400> SEQUENCE: 52
tatttgttgc tcgcaaagtt gcc 23